(12) United States Patent
Milliman

(10) Patent No.: US 8,733,611 B2
(45) Date of Patent: May 27, 2014

(54) RATCHETING MECHANISM FOR SURGICAL STAPLING DEVICE

(75) Inventor: Keith L. Milliman, Bethel, CT (US)

(73) Assignee: Covidien LP, Mansfield, MA (US)

( * ) Notice: Subject to any disclaimer, the term of this patent is extended or adjusted under 35 U.S.C. 154(b) by 284 days.

(21) Appl. No.: 12/397,469

(22) Filed: Mar. 4, 2009

(65) Prior Publication Data

US 2009/0230170 A1 Sep. 17, 2009

Related U.S. Application Data

(60) Provisional application No. 61/035,756, filed on Mar. 12, 2008, provisional application No. 61/044,611, filed on Apr. 14, 2008.

(51) Int. Cl.
*A61B 17/10* (2006.01)
*A61B 17/04* (2006.01)

(52) U.S. Cl.
USPC ............................................ 227/175.2

(58) Field of Classification Search
USPC ................................. 227/175.1–181.1
See application file for complete search history.

(56) References Cited

U.S. PATENT DOCUMENTS

| 3,873,016 A * | 3/1975 | Fishbein ........................ 227/83 |
| 4,196,836 A * | 4/1980 | Becht ............................. 227/110 |
| 4,596,350 A | 6/1986 | Smith et al. |
| 4,796,793 A | 1/1989 | Smith et al. |
| 5,161,725 A * | 11/1992 | Murray et al. ............. 227/182.1 |
| 5,344,061 A | 9/1994 | Crainich |
| 5,431,323 A | 7/1995 | Smith et al. |
| 5,431,668 A | 7/1995 | Burbank, III et al. |
| 5,533,661 A | 7/1996 | Main et al. |
| 5,582,616 A | 12/1996 | Bolduc et al. |
| 5,695,504 A | 12/1997 | Gifford, III et al. |
| 5,762,256 A | 6/1998 | Mastri et al. |
| 5,824,008 A | 10/1998 | Bolduc et al. |
| 5,904,697 A | 5/1999 | Gifford, III et al. |
| 5,937,951 A * | 8/1999 | Izuchukwu et al. ....... 227/176.1 |
| 5,964,772 A | 10/1999 | Bolduc et al. |
| 6,099,537 A | 8/2000 | Sugai et al. |
| 6,280,460 B1 | 8/2001 | Bolduc et al. |
| 6,330,965 B1 | 12/2001 | Milliman et al. |
| 6,383,197 B1 | 5/2002 | Conlon et al. |
| 6,387,105 B1 | 5/2002 | Gifford, III et al. |
| 6,402,780 B2 | 6/2002 | Williamson, IV et al. |

(Continued)

FOREIGN PATENT DOCUMENTS

| EP | 0539762 | 5/1993 |
| EP | 0 541 987 B1 | 7/1996 |

(Continued)

OTHER PUBLICATIONS

European Search Report for corresponding EP 09250688, date of mailing is Aug. 16, 2012 (10 pgs).

*Primary Examiner* — Robert Long

(57) ABSTRACT

A surgical stapling device comprising a housing, an elongated portion, an end effector, and a movable handle disposed in mechanical cooperation with the housing and movable between a first open position and a second approximated position for affecting a function of the end effector. A ratchet mechanism is disposed in mechanical cooperation with the movable handle and is configured to substantially prevent the movable handle from moving towards its first open position until the movable handle reaches a predetermined position.

25 Claims, 54 Drawing Sheets

(56) References Cited

U.S. PATENT DOCUMENTS

| | | | |
|---|---|---|---|
| 6,599,304 B1 | 7/2003 | Selmon et al. | |
| 6,830,174 B2 * | 12/2004 | Hillstead et al. | 227/175.1 |
| 6,905,057 B2 | 6/2005 | Swayze et al. | |
| 6,959,852 B2 | 11/2005 | Shelton, IV et al. | |
| 7,000,819 B2 | 2/2006 | Swayze et al. | |
| 7,048,171 B2 * | 5/2006 | Thornton et al. | 227/176.1 |
| 7,052,504 B2 | 5/2006 | Hughett | |
| 7,059,508 B2 | 6/2006 | Shelton, IV et al. | |
| 7,083,075 B2 | 8/2006 | Swayze et al. | |
| 7,128,254 B2 | 10/2006 | Shelton, IV et al. | |
| 7,140,528 B2 | 11/2006 | Shelton, IV | |
| 7,143,925 B2 | 12/2006 | Shelton, IV et al. | |
| 7,143,926 B2 | 12/2006 | Shelton, IV et al. | |
| 7,147,139 B2 | 12/2006 | Schwemberger et al. | |
| 7,147,140 B2 | 12/2006 | Wukusick et al. | |
| 7,168,604 B2 | 1/2007 | Milliman et al. | |
| 7,211,092 B2 | 5/2007 | Hughett | |
| 7,357,287 B2 * | 4/2008 | Shelton et al. | 227/178.1 |
| 7,364,060 B2 | 4/2008 | Milliman | |
| 7,422,136 B1 * | 9/2008 | Marczyk | 227/175.1 |
| 7,556,186 B2 | 7/2009 | Milliman | |
| 7,637,409 B2 * | 12/2009 | Marczyk | 227/175.1 |
| 7,731,072 B2 * | 6/2010 | Timm et al. | 227/175.1 |
| 7,784,663 B2 | 8/2010 | Shelton, IV | |
| 7,819,296 B2 * | 10/2010 | Hueil et al. | 227/175.2 |
| 7,819,297 B2 * | 10/2010 | Doll et al. | 227/176.1 |
| 7,819,298 B2 * | 10/2010 | Hall et al. | 227/176.1 |
| 7,866,527 B2 * | 1/2011 | Hall et al. | 227/175.2 |
| 7,886,951 B2 | 2/2011 | Hessler | |
| 8,113,410 B2 * | 2/2012 | Hall et al. | 227/180.1 |
| 8,608,045 B2 * | 12/2013 | Smith et al. | 227/175.2 |
| 2002/0151914 A1 | 10/2002 | Gifford, III et al. | |
| 2003/0023251 A1 | 1/2003 | Gifford, III et al. | |
| 2003/0065347 A1 | 4/2003 | Gifford, III et al. | |
| 2003/0176878 A1 | 9/2003 | Bolduc et al. | |
| 2004/0097971 A1 | 5/2004 | Hughett | |
| 2005/0067457 A1 | 3/2005 | Shelton, IV et al. | |
| 2005/0067458 A1 | 3/2005 | Swayze et al. | |
| 2005/0067459 A1 | 3/2005 | Swayze et al. | |
| 2005/0096676 A1 | 5/2005 | Gifford, III et al. | |
| 2005/0107824 A1 * | 5/2005 | Hillstead et al. | 606/205 |
| 2005/0149077 A1 | 7/2005 | Gifford, III et al. | |
| 2005/0178813 A1 | 8/2005 | Swayze et al. | |
| 2006/0000867 A1 | 1/2006 | Shelton, IV et al. | |
| 2006/0000868 A1 | 1/2006 | Shelton, IV et al. | |
| 2006/0022014 A1 | 2/2006 | Shelton, IV et al. | |
| 2006/0022015 A1 | 2/2006 | Shelton, IV et al. | |
| 2006/0049230 A1 | 3/2006 | Shelton, IV et al. | |
| 2006/0060630 A1 | 3/2006 | Shelton, IV et al. | |
| 2006/0097026 A1 | 5/2006 | Shelton, IV | |
| 2006/0175375 A1 | 8/2006 | Shelton, IV et al. | |
| 2006/0235437 A1 | 10/2006 | Vitali et al. | |
| 2006/0235439 A1 | 10/2006 | Molitor et al. | |
| 2006/0235444 A1 | 10/2006 | Huitema et al. | |
| 2007/0068990 A1 * | 3/2007 | Shelton et al. | 227/175.1 |
| 2008/0149685 A1 * | 6/2008 | Smith et al. | 227/181.1 |
| 2008/0223904 A1 * | 9/2008 | Marczyk | 227/176.1 |
| 2008/0277449 A1 * | 11/2008 | Marczyk | 227/176.1 |
| 2008/0314957 A1 * | 12/2008 | Boudreaux | 227/175.2 |
| 2009/0206123 A1 * | 8/2009 | Doll et al. | 227/175.1 |
| 2009/0206124 A1 * | 8/2009 | Hall et al. | 227/175.1 |
| 2009/0206128 A1 * | 8/2009 | Hueil et al. | 227/175.2 |
| 2009/0206129 A1 * | 8/2009 | Doll et al. | 227/175.2 |
| 2009/0206130 A1 * | 8/2009 | Hall et al. | 227/175.2 |
| 2009/0206133 A1 * | 8/2009 | Morgan et al. | 227/176.1 |
| 2009/0230170 A1 * | 9/2009 | Milliman | 227/176.1 |
| 2010/0089972 A1 * | 4/2010 | Marczyk | 227/178.1 |
| 2011/0006099 A1 * | 1/2011 | Hall et al. | 227/175.1 |

FOREIGN PATENT DOCUMENTS

| | | |
|---|---|---|
| EP | 1 769 755 A2 | 4/2007 |
| EP | 2160984 | 3/2010 |
| GB | 2141066 | 12/1984 |
| WO | WO 98/11814 A2 | 3/1998 |
| WO | 2004032766 | 4/2004 |
| WO | WO 2005/037084 A2 | 4/2005 |

* cited by examiner

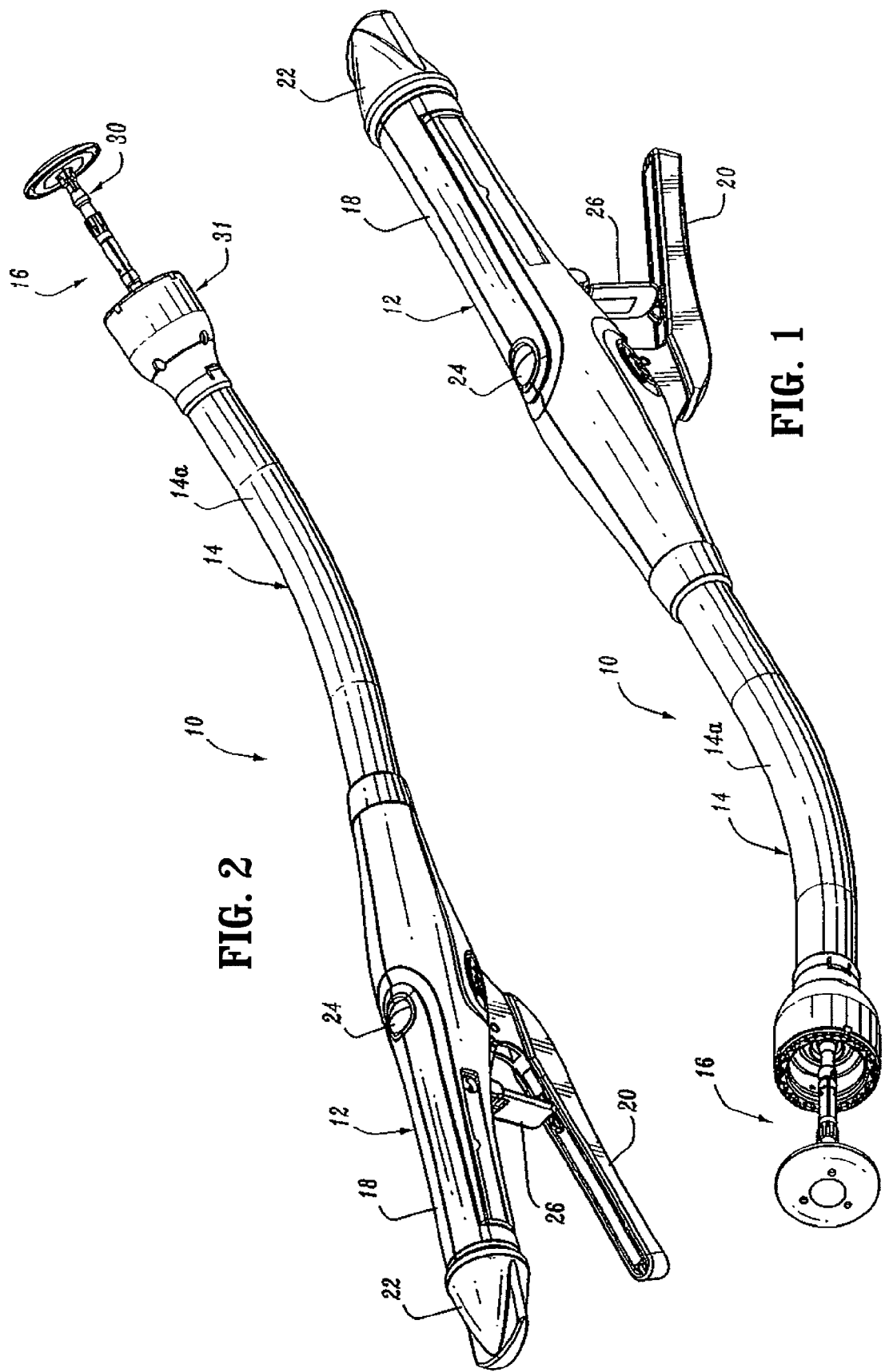

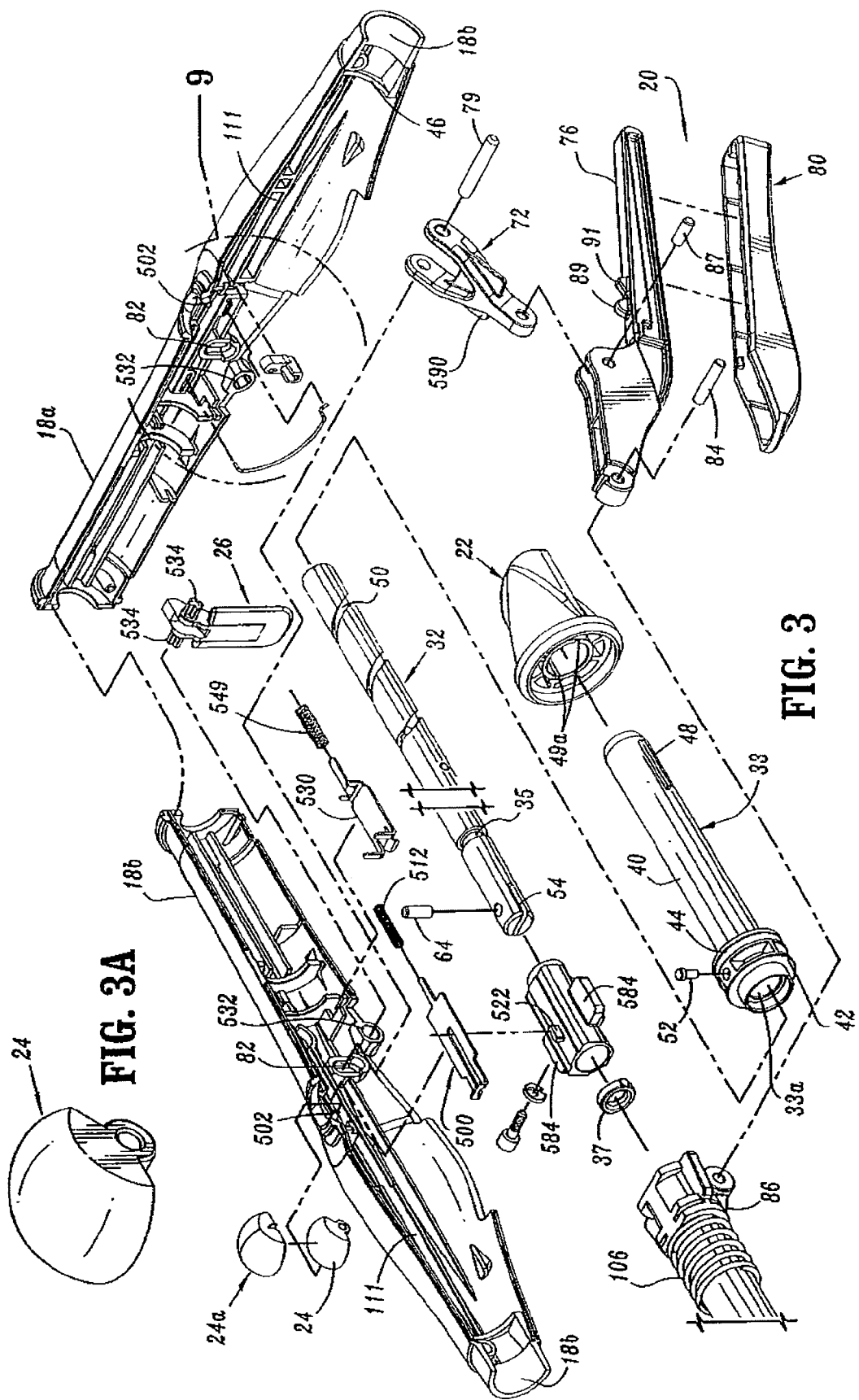

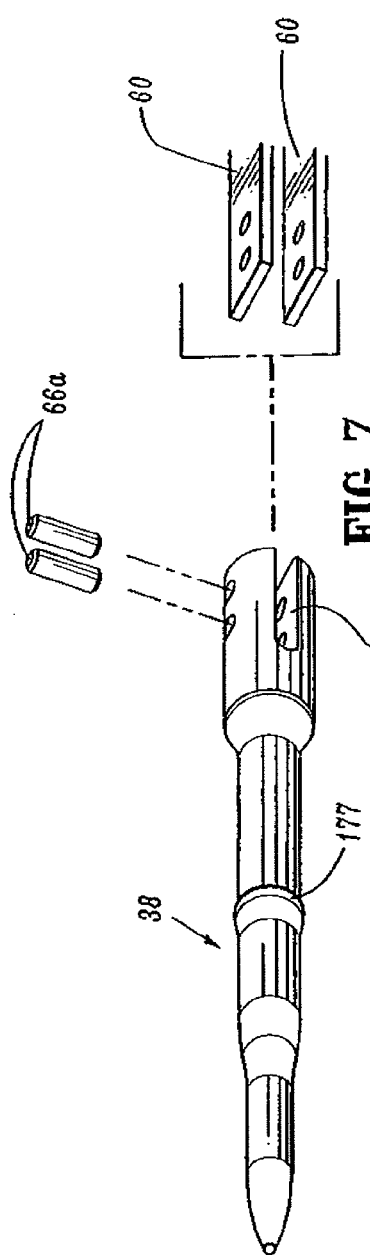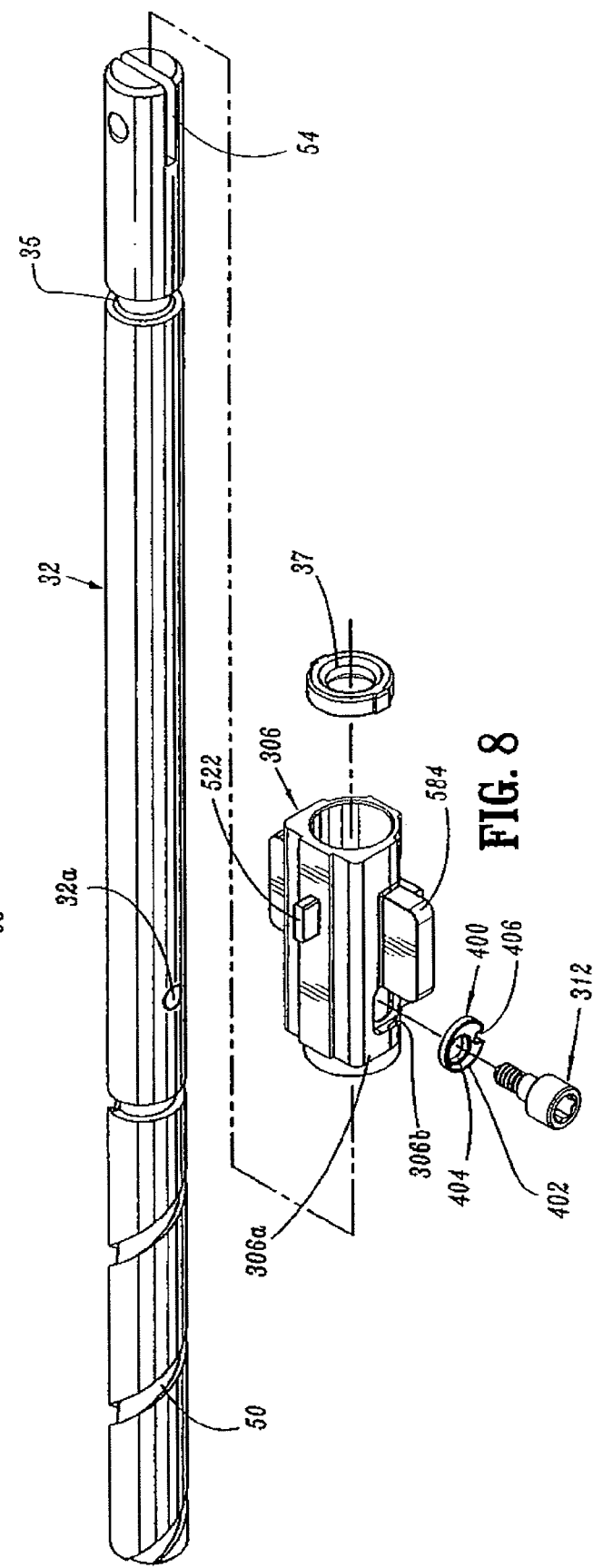

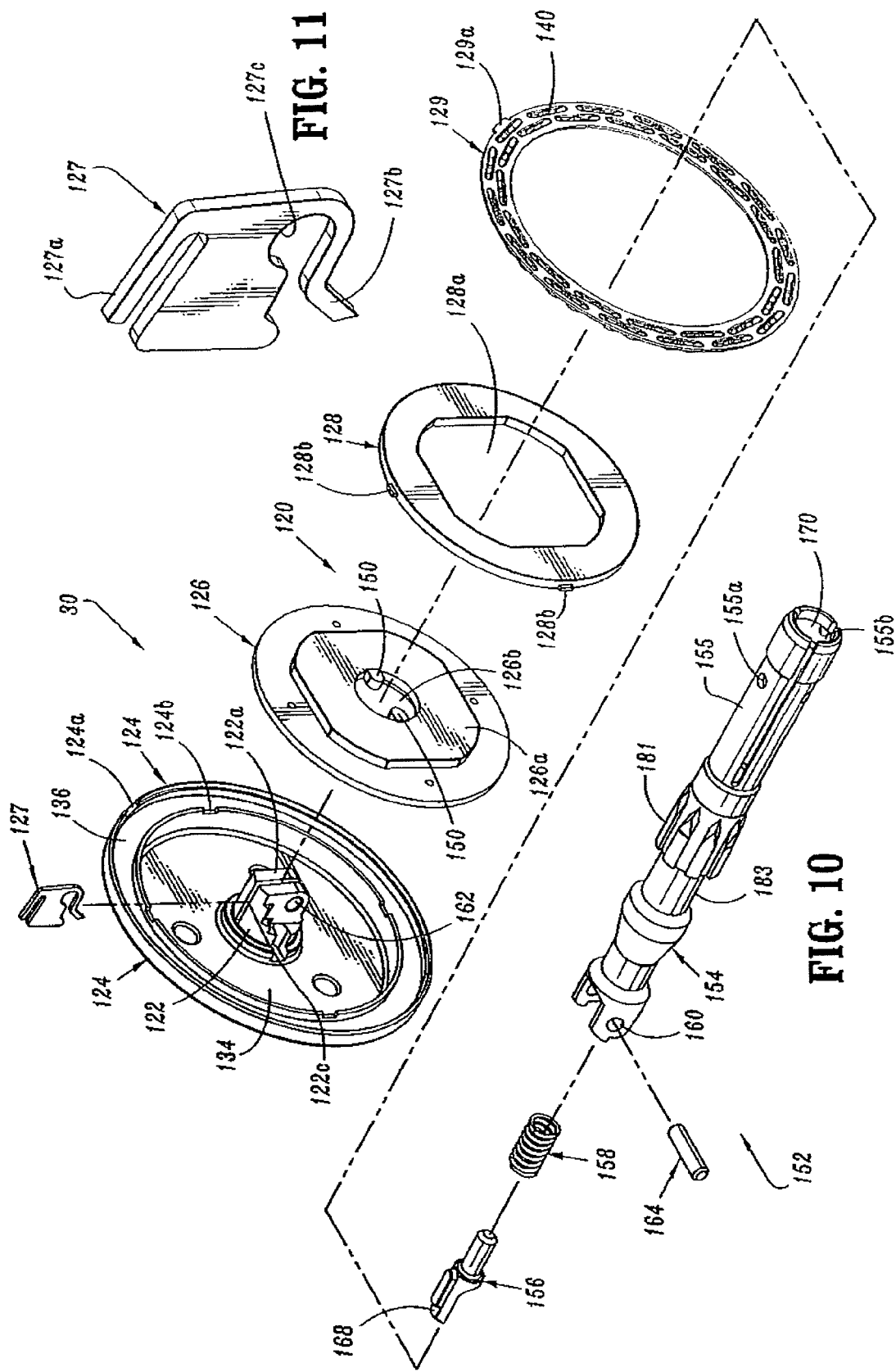

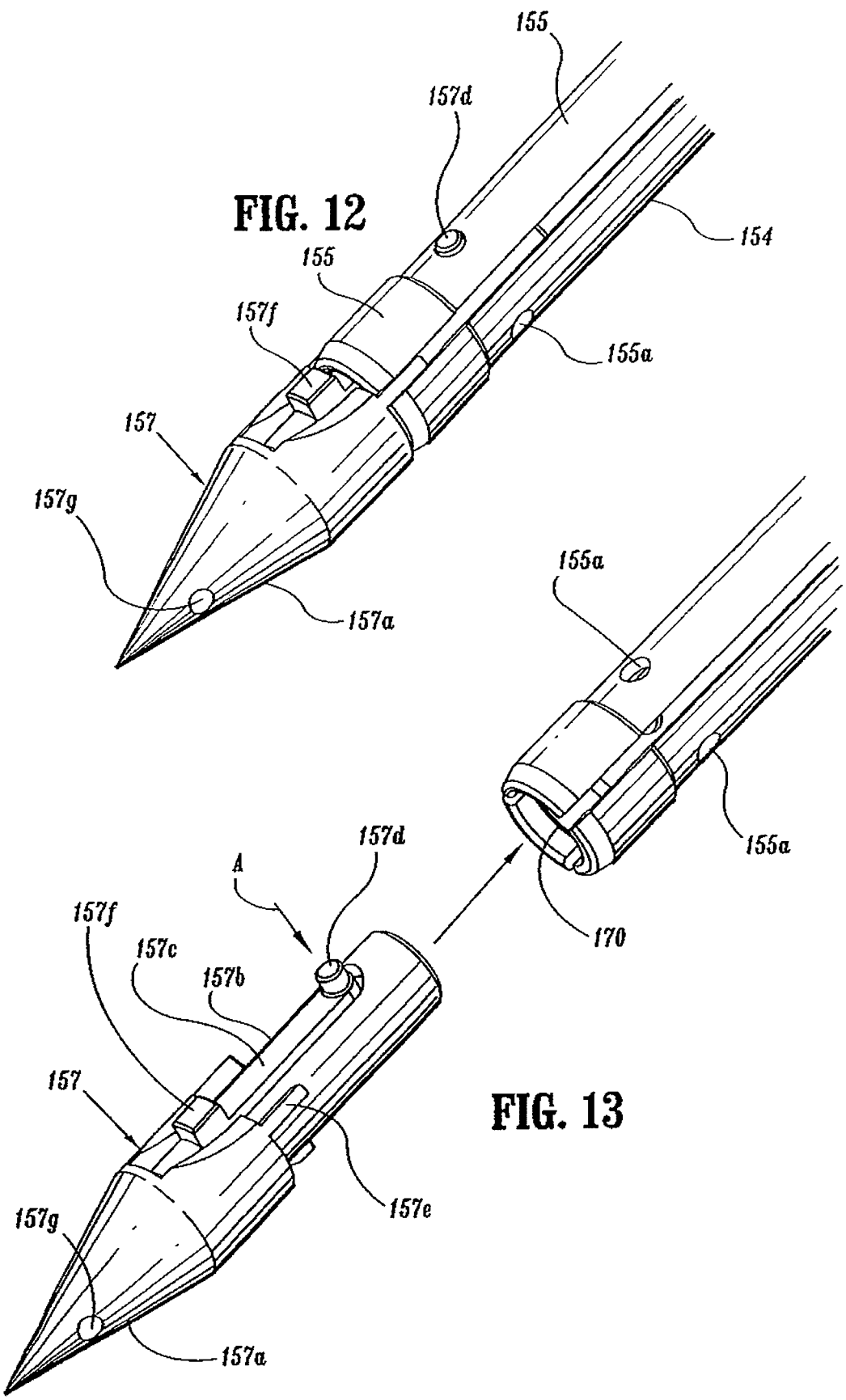

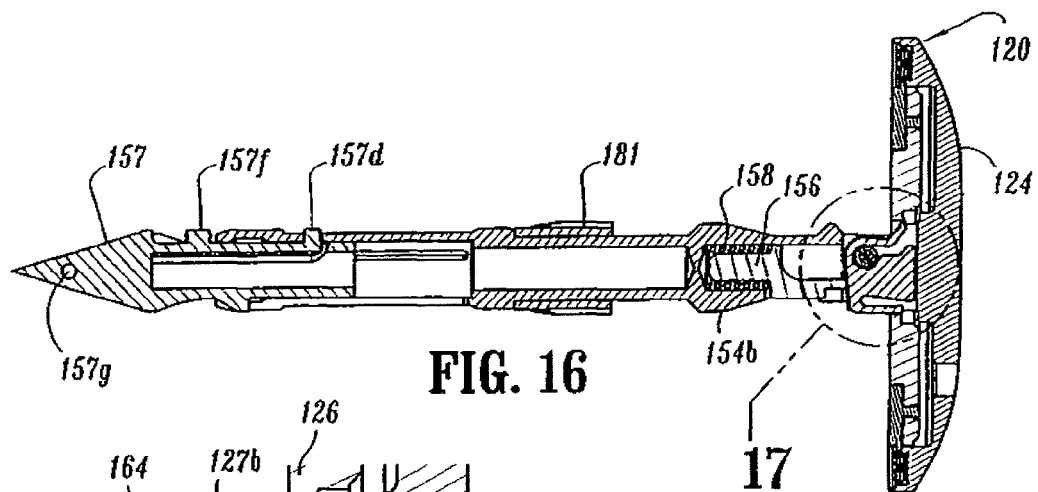
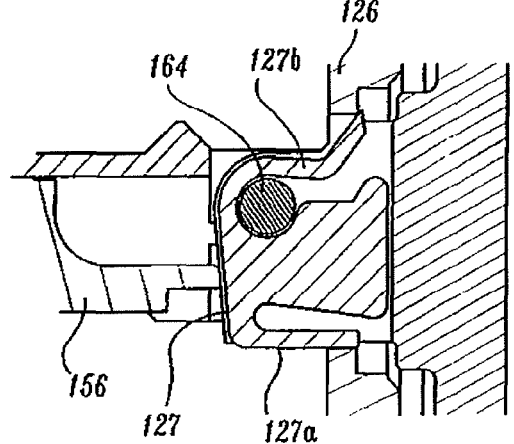
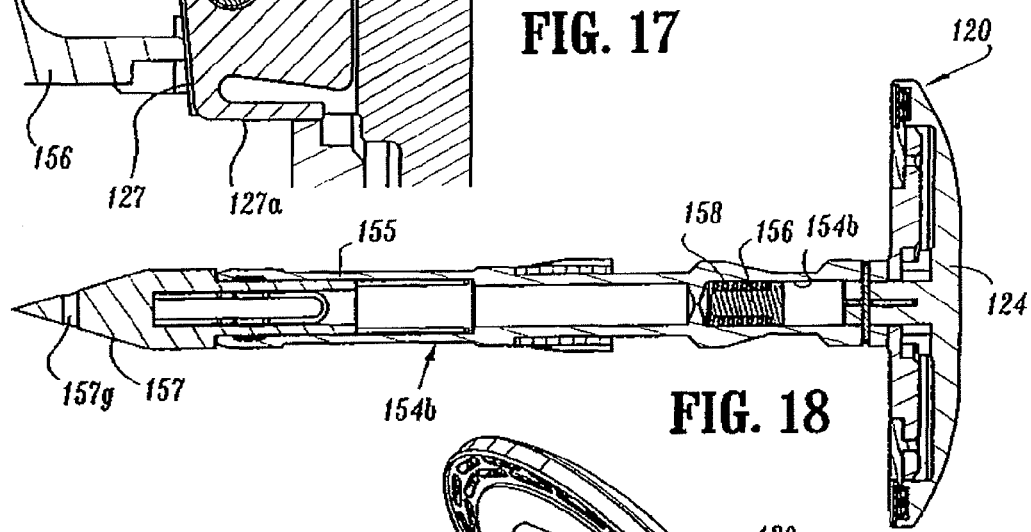
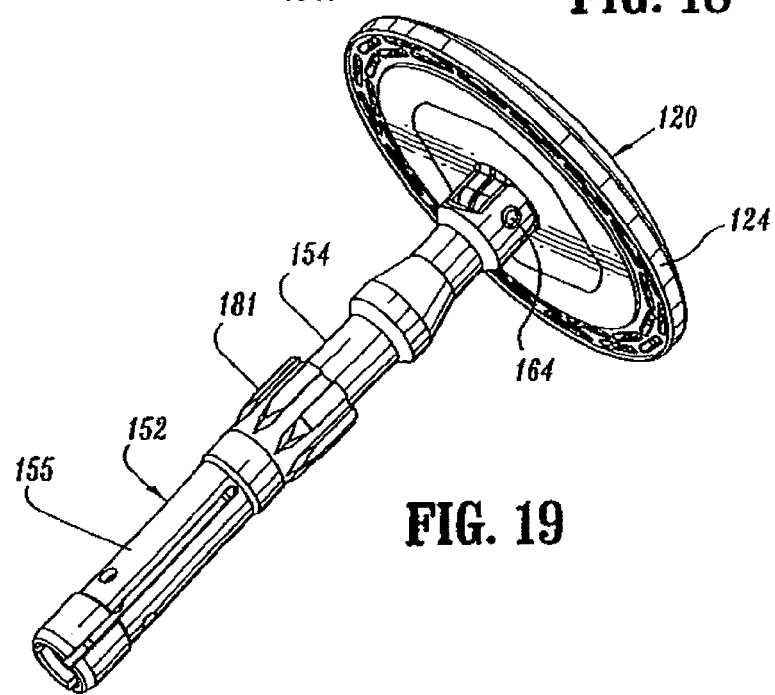

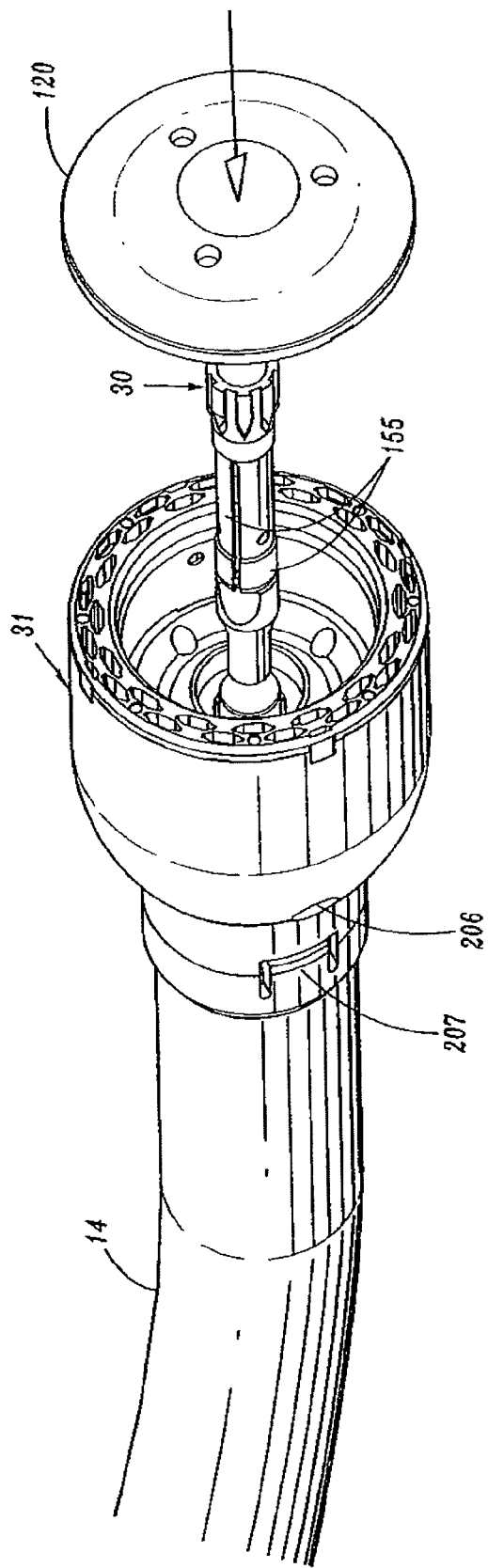
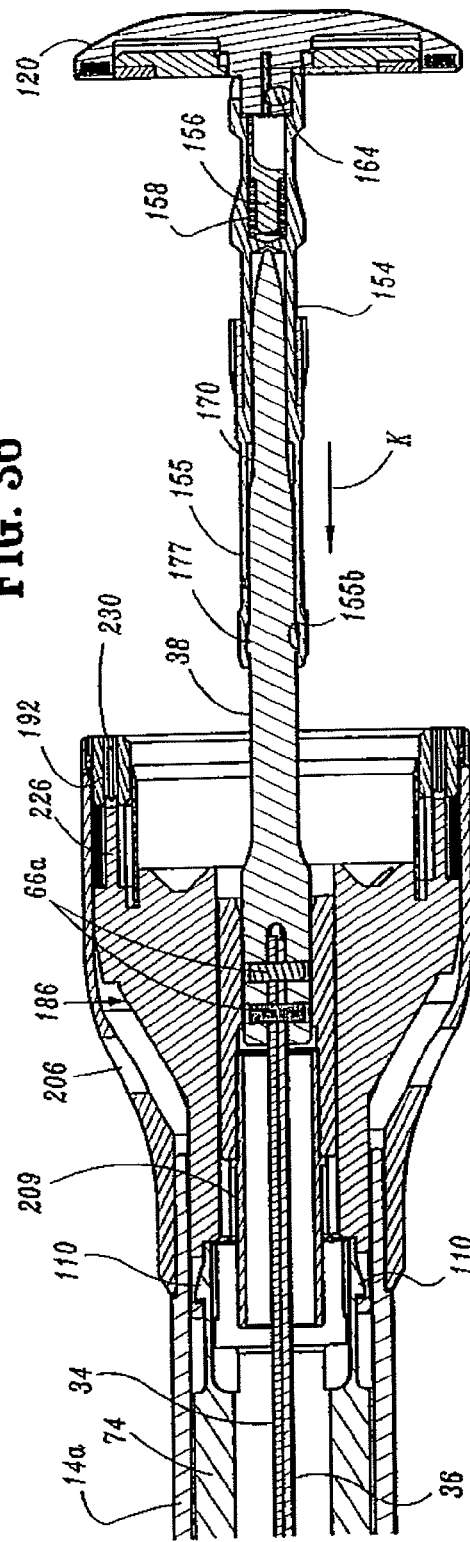
FIG. 36
FIG. 37

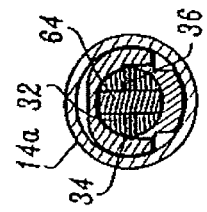
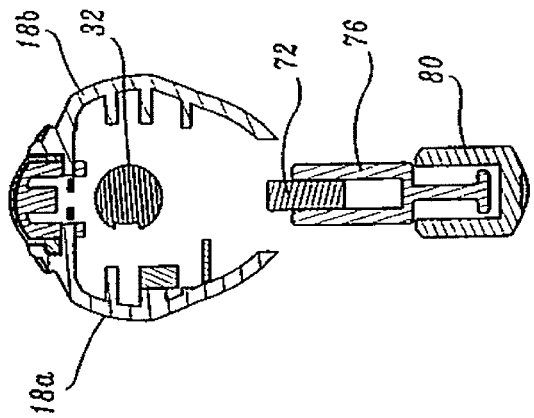
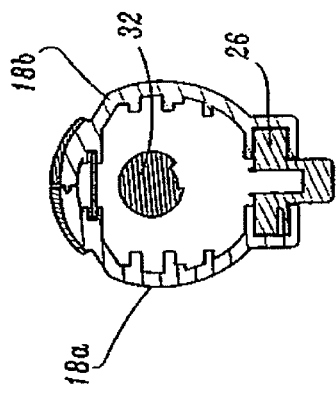
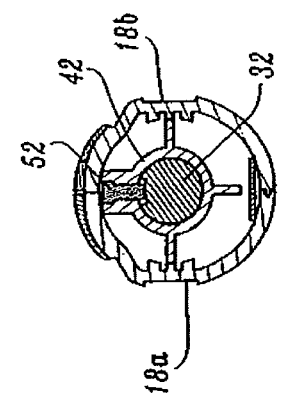
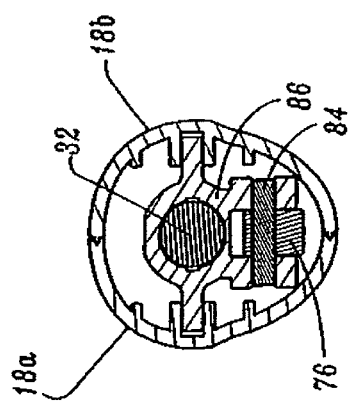
FIG. 39  FIG. 40  FIG. 41  FIG. 42  FIG. 43  FIG. 44

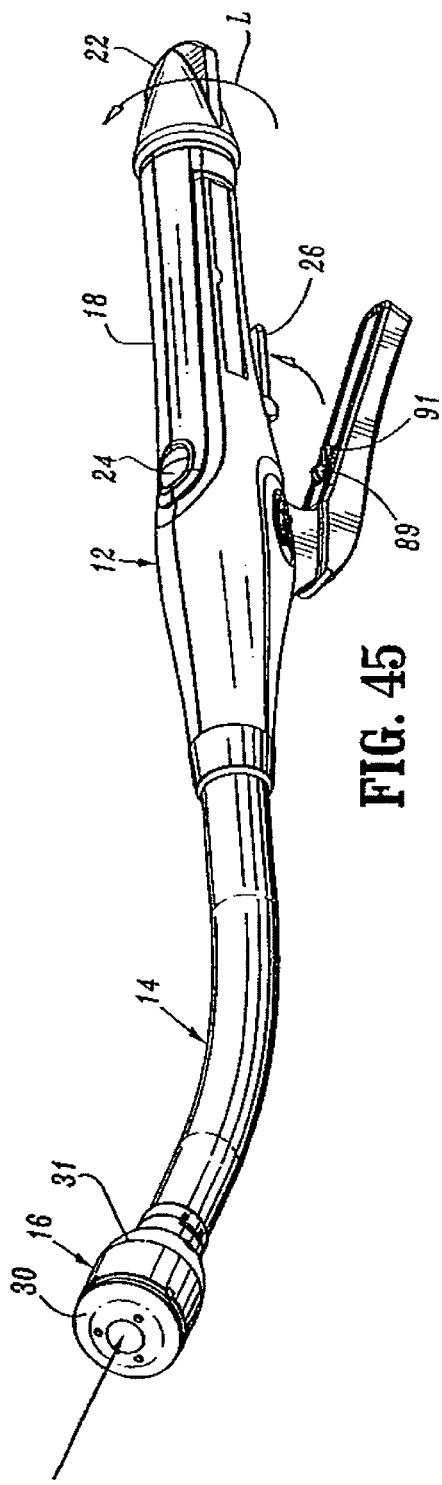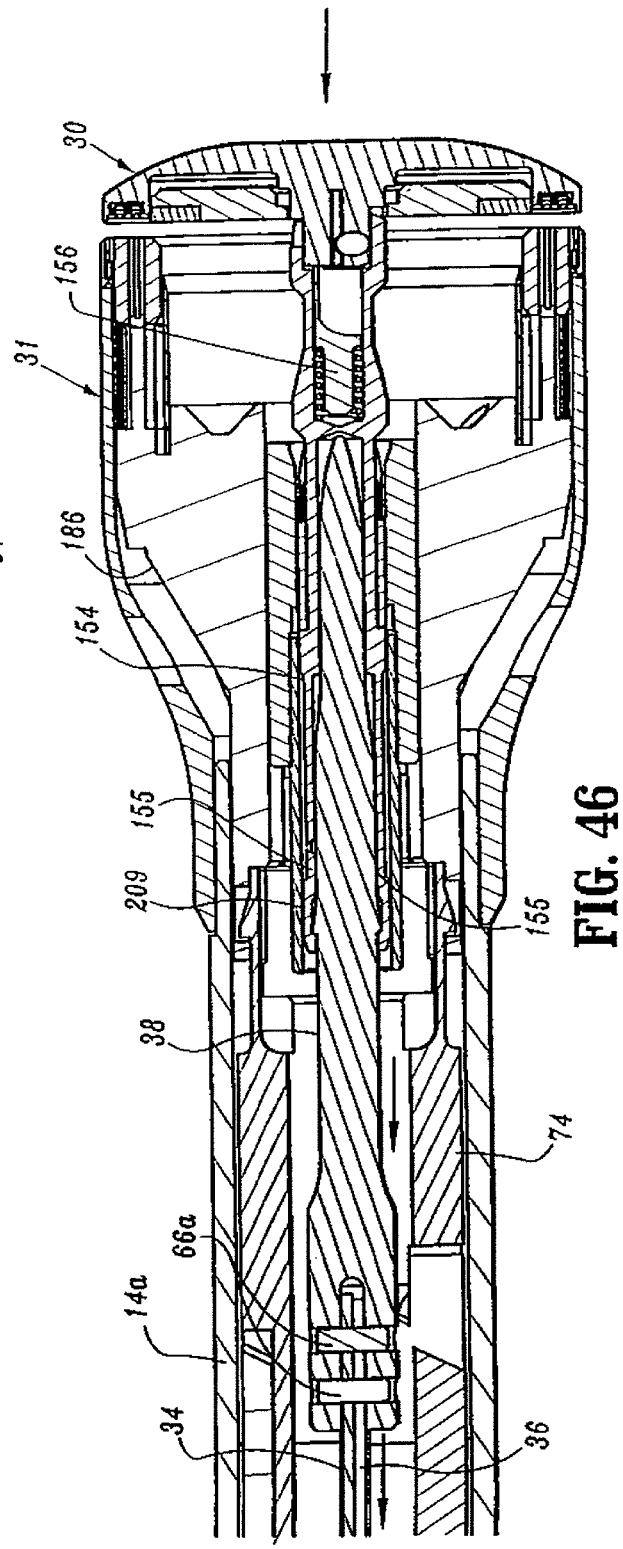
FIG. 45
FIG. 46

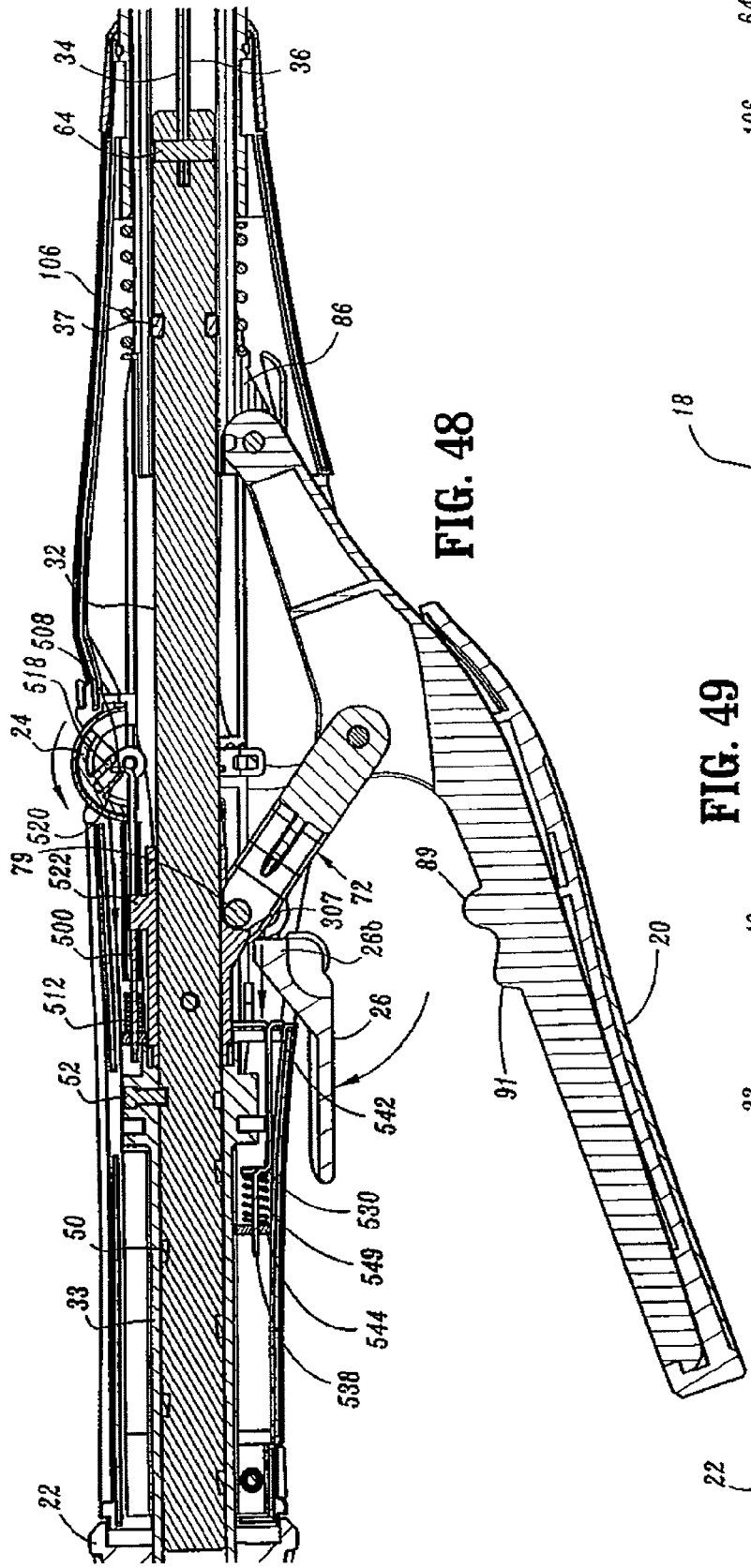
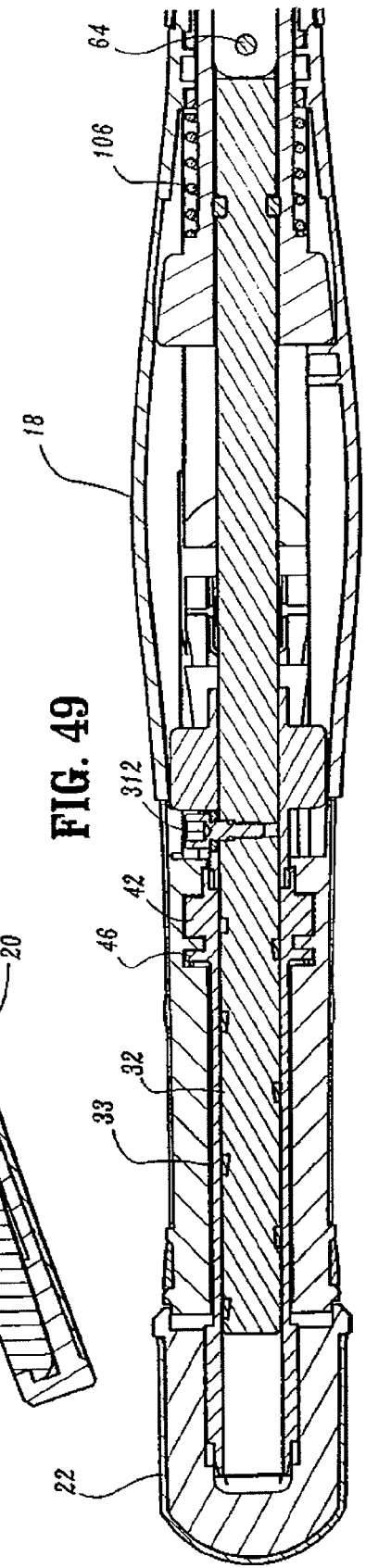
FIG. 48
FIG. 49

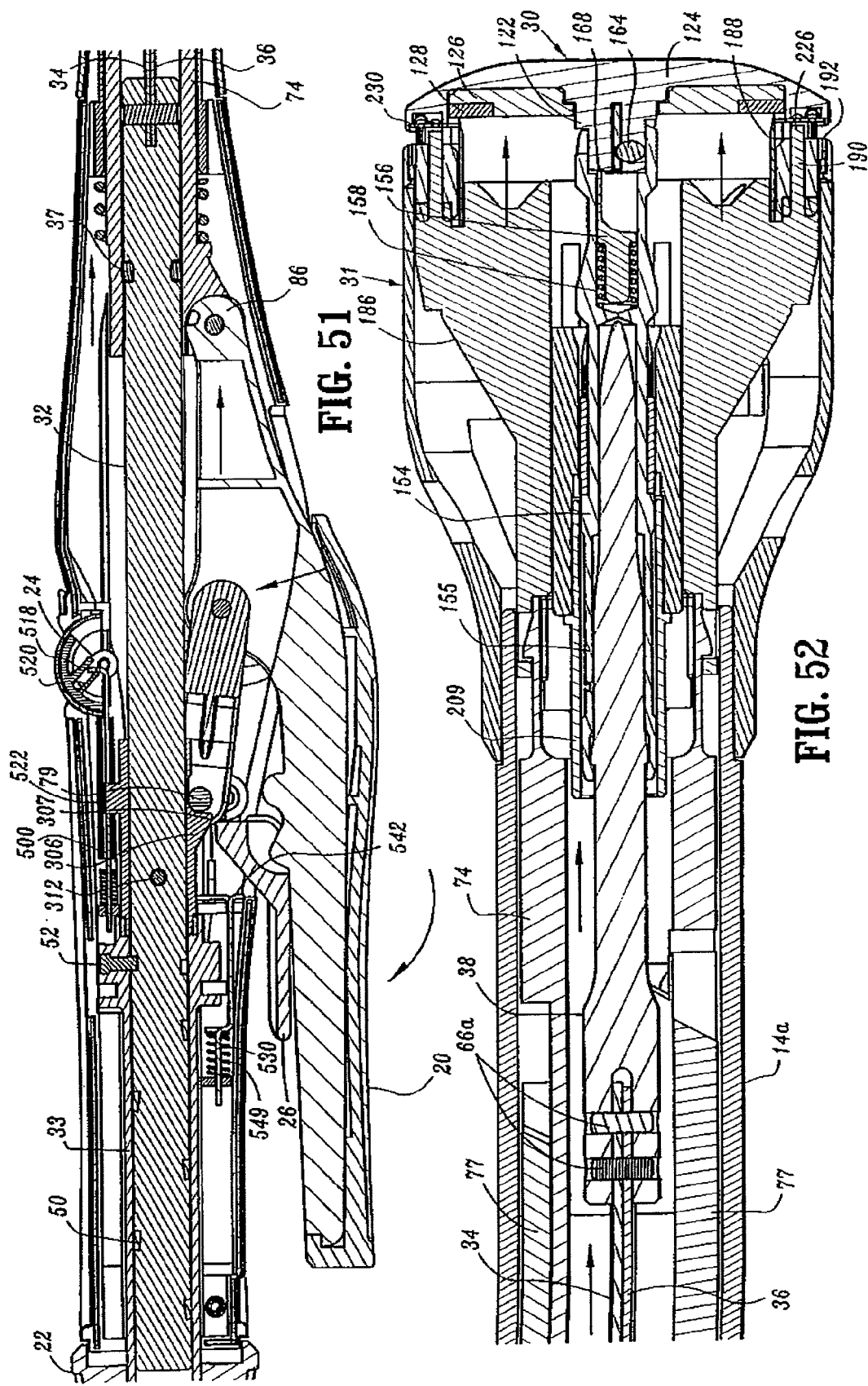

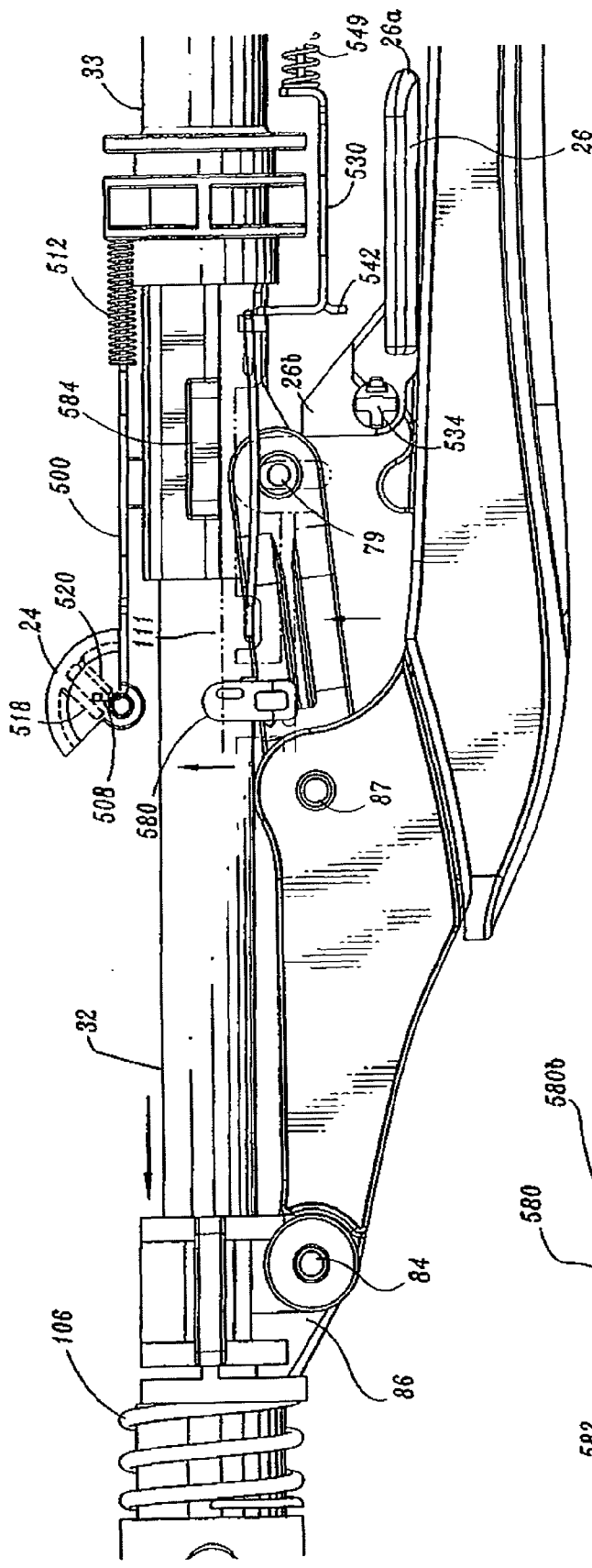
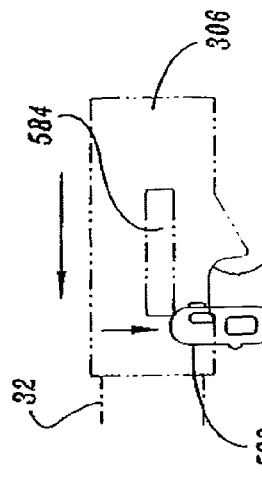
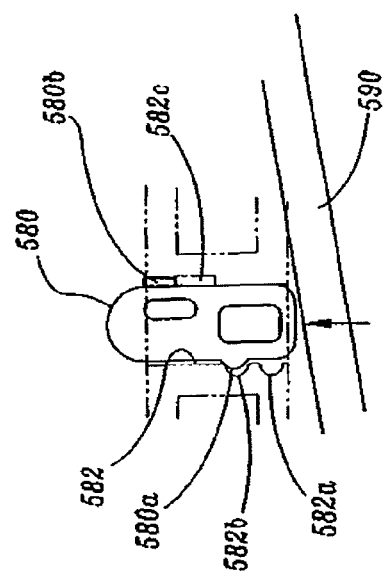
FIG. 53
Fig. 58
FIG. 54

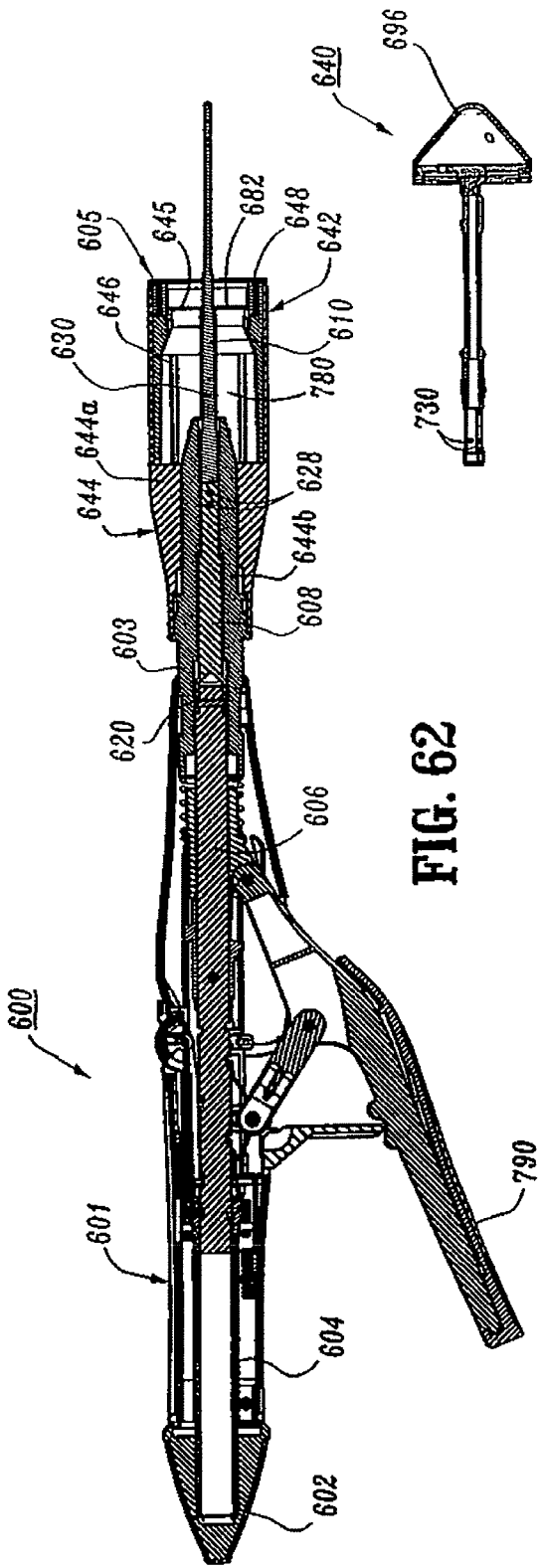
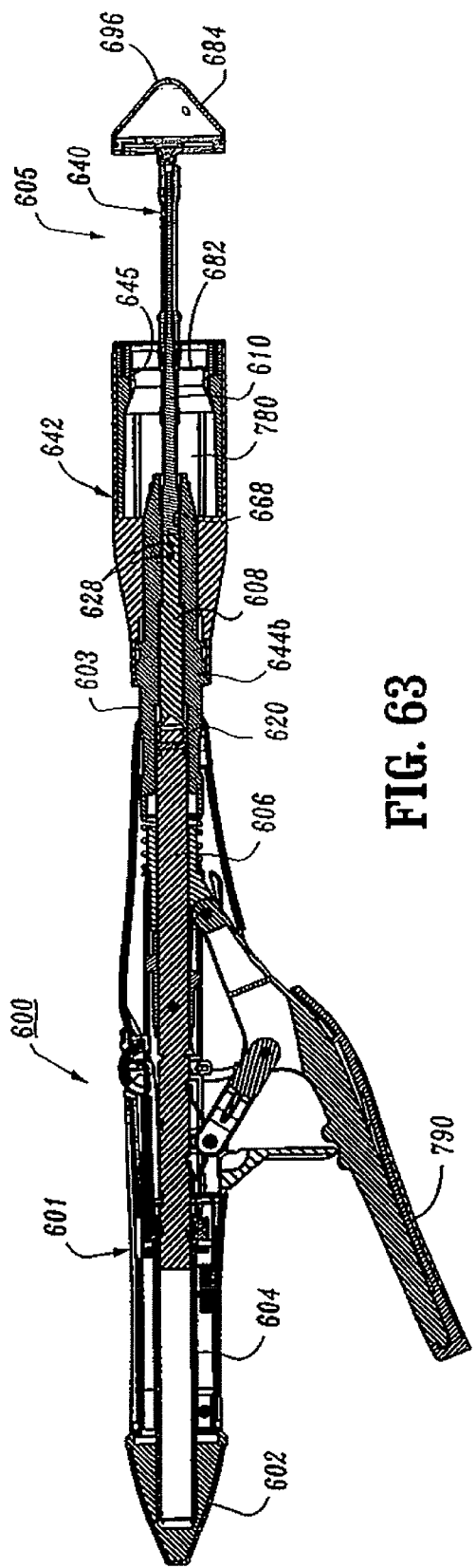
FIG. 62
FIG. 64
FIG. 63

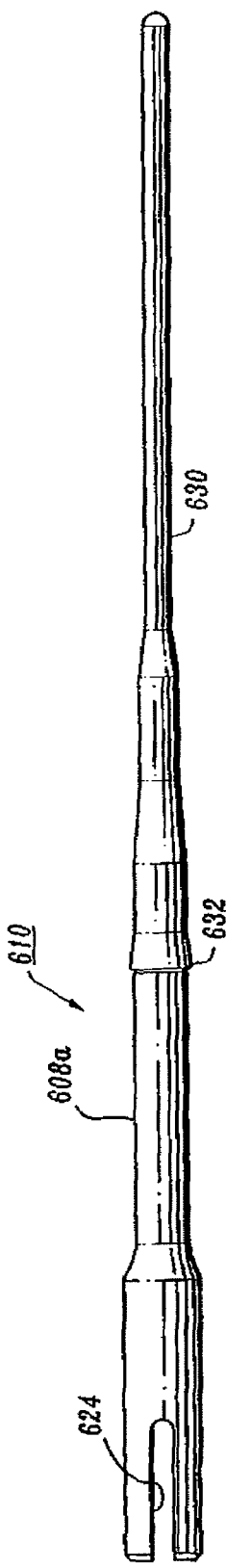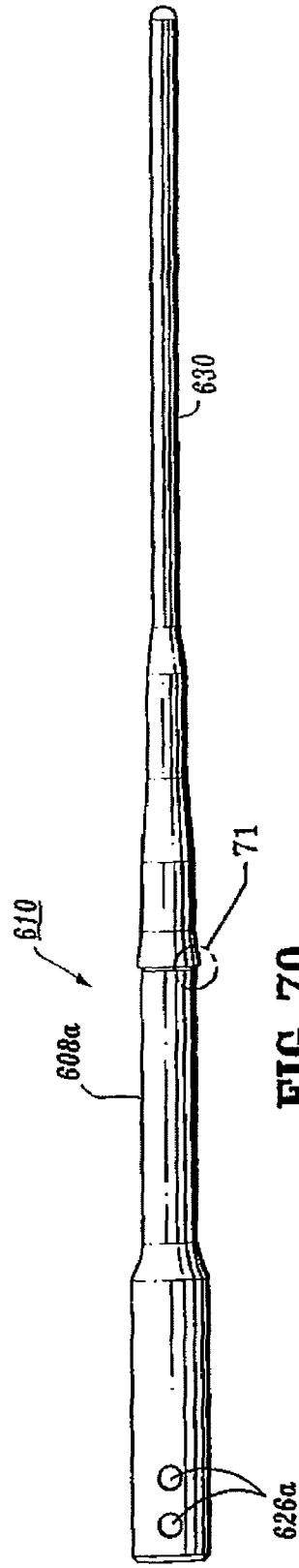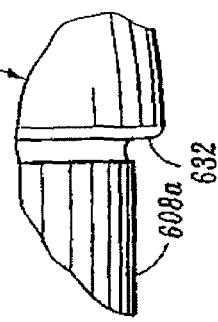

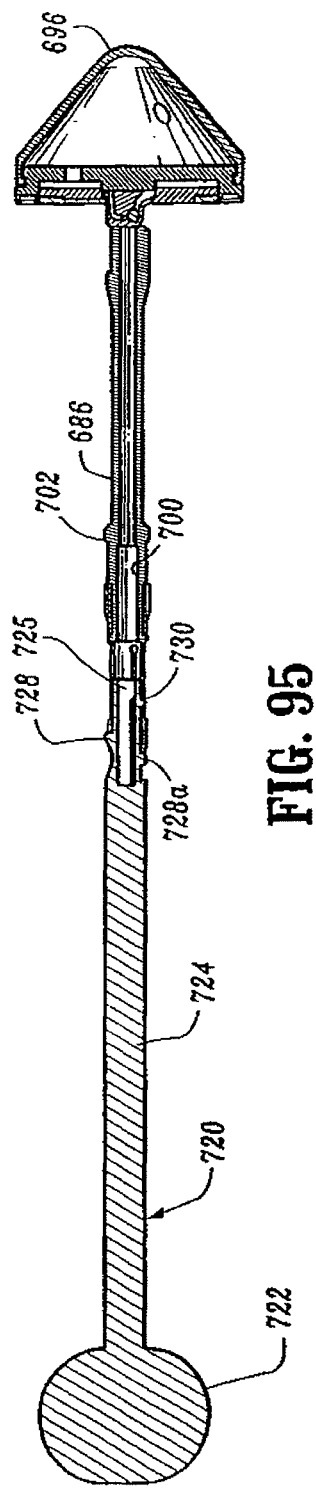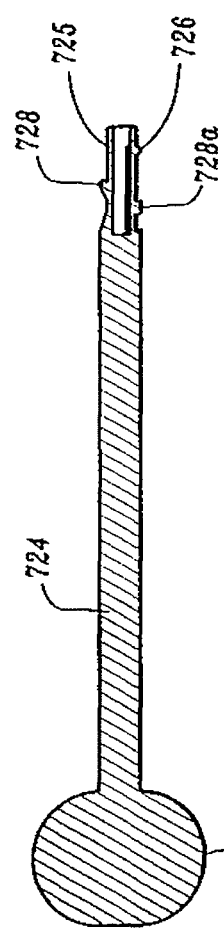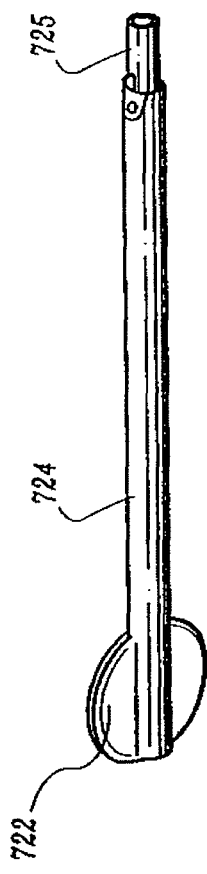

RATCHETING MECHANISM FOR SURGICAL STAPLING DEVICE

CROSS-REFERENCE TO RELATED APPLICATIONS

This application claims the benefit of and priority to U.S. Provisional Patent Application Nos. 61/035,756 filed Mar. 12, 2008 and 61/044,611 filed Apr. 14, 2008, the entire disclosure of which is incorporated by reference herein.

BACKGROUND

1. Technical Field

The present disclosure relates generally to a surgical stapling device for applying surgical staples to body tissue. More particularly, the present disclosure relates to a surgical stapling device suitable for performing circular anastomosis and/or treatment to internal walls of hollow tissue organs.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is concurrently advanced to core tissue with the hollow organ to free a tubular passage within the organ.

Besides anastomosis of hollow organs, surgical stapling devices for performing circular anastomosis have been used to treat internal hemorrhoids in the rectum. Hemorrhoids are masses of tissue in the anus containing enlarged blood vessels. Internal hemorrhoids are inside the anal canal; external hemorrhoids lie outside the anal canal. In hemorrhoidectomy, the hemorrhoids are removed. Stapled hemorrhoidopexy is a surgical procedure in which the stapling device is used to remove tissue just above the hemorrhoids in order to pull the hemorrhoids back up inside the rectum and reduce the symptoms. The staples interrupt the blood flow of the superior hemorrhoidal arterial branches, cutting off the blood supply, thus causing the hemorrhoids to shrink.

During the use of a circular stapling device for hemorrhoid treatment, the anvil head and the staple holding component of the device are inserted through and into the rectum with the anvil head and the stapling holding component in an open or unapproximated position. Thereafter, a purse string suture is used to pull the internal hemorrhoidal tissue and/or mucosal tissue toward the anvil rod. Next, the anvil head and the staple holding component are approximated to clamp the hemorrhoidal tissue and/or mucosal tissue between the anvil head and the staple holding component. The stapling device is fired to remove the hemorrhoidal tissue and/or mucosal tissue and staple the cut.

Typically, such surgical stapling devices include a movable handle or trigger which is movable through a firing stroke to simultaneously affect formation of a circular array of staples and coring or cutting of tissue. When the movable handle is moved through only a portion of the firing stroke during firing of the stapling device, the circular array of staples may not be adequately formed, nor may the tissue be adequately cut. In current instruments, when the movable handle is released after firing of the stapling device, the movable handle is returned by a biasing member to its pre-fired position. This occurs whether or not the handle has been moved through a complete firing stroke or only a portion of the firing stroke. Thus, where a surgeon inadvertently fails to move the handle or trigger to complete the firing stroke and acceptable staple formation and cutting are not affected, the handle will still return to its pre-fired position.

Accordingly, it would be desirable for a surgical stapling device to include a mechanism for substantially preventing the movable handle from prematurely returning to its pre-fired position until the movable handle has been moved substantially through the full firing stroke.

SUMMARY

The present disclosure provides a surgical stapling device comprising a housing, an elongated portion extending distally from the housing, and an end effector, at least a portion of which is disposed in mechanical cooperation with a distal portion of the elongated portion. A movable handle is disposed in mechanical cooperation with the housing and is movable between a first open position and a second approximated position for affecting a function of the end effector. A ratchet mechanism is disposed in mechanical cooperation with the movable handle, and is configured to substantially prevent the movable handle from moving towards its first open position until the movable handle reaches a predetermined position.

The ratchet mechanism includes a rack having rack teeth and a cam surface and disposed in mechanical cooperation with the housing, and a pawl having pawl teeth and disposed in mechanical cooperation with the movable handle. The rack teeth and the pawl teeth are configured for engagement with each other. A spring is disposed in mechanical cooperation with the movable handle and is configured to bias at least one of the pawl and the rack towards the other such that the pawl teeth and the rack teeth are in engagement with one another. Preferably, the cam surface is configured to disengage the pawl teeth and the rack teeth upon the cam surface contacting the pawl for facilitating movement of the movable handle towards its first open position.

In a preferred embodiment, the end effector is configured for ejection of staples therefrom upon movement of the movable handle from its first open position towards its second approximated position, and the ratchet mechanism is configured to substantially prevent the movable handle from moving towards its first open position until at least one staple has been ejected from the end effector.

The surgical stapling device in a preferred embodiment includes a knife configured for distal translation upon movement of the movable handle from its first open position towards its second approximated position, and the ratchet mechanism in this embodiment is configured to substantially prevent the movable handle from moving towards its first open position until the knife has been distally translated. Preferably, the cam surface of the rack moves the pawl away from the rack after the knife has been distally translated.

The device may further include an override disposed in mechanical cooperation with the pawl configured to allow a user to disengage the pawl teeth from the rack teeth before the movable handle reaches the predetermined position, to allow the movable handle to be moved towards its first open position.

The surgical stapling device may include a clip disposed in mechanical cooperation with the ratchet mechanism and configured to releasably maintain the pawl teeth and the rack teeth in a disengaged position.

In a preferred embodiment, the end effector includes an anvil assembly having an anvil head and an anvil center rod and a shell assembly supporting a plurality of staples, wherein the anvil assembly is movable in relation to the shell assembly between spaced and approximated positions.

The present disclosure also provides a surgical stapling device comprising a housing, an elongated portion extending distally from the housing, and an end effector disposed adjacent a distal portion of the elongated portion and including an anvil assembly and a shell assembly. The anvil assembly includes an anvil head and an anvil center rod having a proximal end and a distal end. The anvil head is supported on the distal end of the anvil center rod. The shell assembly supports a plurality of staples and the anvil assembly is movable in relation to the shell assembly between spaced and approximated positions. A movable handle is disposed in mechanical cooperation with the housing and is movable between a first open position and a second approximated position for affecting a function of the end effector. A ratchet mechanism is disposed in mechanical cooperation with the movable handle and is configured to substantially prevent the movable handle from moving towards its first open position until the movable handle reaches a predetermined position.

In one embodiment the device includes an approximation mechanism including an anvil retainer for supporting the anvil assembly, the anvil retainer including an annular shoulder configured to engage the anvil center rod to fasten the anvil center rod to the anvil retainer.

The present disclosure also provides a ratchet mechanism for use with a surgical stapling device, the ratchet mechanism comprising a rack having rack teeth and a cam surface and a pawl having pawl teeth, wherein the rack teeth and the pawl teeth are configured for engagement with each other. A spring is disposed in mechanical cooperation with one of the pawl and the rack. The spring is positioned to bias at least one of the pawl and the rack towards the other to engage the rack teeth and the pawl teeth. The cam surface is configured to disengage the pawl teeth and the rack teeth upon the cam surface contacting the pawl. The ratchet mechanism is configured to substantially prevent a movable handle of the surgical stapling device from moving towards a first open position until the movable handle reaches a predetermined position.

The device may further include an override disposed in mechanical cooperation with the pawl, the override configured to allow a user to disengage the pawl teeth from the rack teeth before the movable handle reaches the predetermined position to allow the movable handle to be moved towards its first open position.

DESCRIPTION OF THE DRAWINGS

Various embodiments of the presently disclosed surgical stapling device are disclosed herein with reference to the drawings, wherein:

FIG. 1 is a top side perspective view from the proximal end of the presently disclosed surgical stapling device in the unapproximated position;

FIG. 2 is a top side perspective view from the distal end of the surgical stapling device shown in FIG. 1;

FIG. 3 is a side perspective exploded view of the handle assembly of the surgical stapling device shown in FIG. 1;

FIG. 3A is a top perspective view of the indicator of the handle assembly shown in FIG. 3;

FIG. 7 is an enlarged side perspective of the anvil retainer and band portions of the central body portion shown in FIG. 6;

FIG. 8 is a side perspective view of the screw and screw stop of the approximation mechanism of the handle assembly shown in FIG. 5;

FIG. 10 is a side perspective exploded view from the proximal end of the anvil assembly of the surgical stapling device shown in FIG. 1;

FIG. 11 is a side perspective view of the retaining clip of the anvil assembly shown in FIG. 10;

FIG. 12 is a side perspective view of the distal end of the center rod of the anvil assembly shown in FIG. 10 with a removable trocar fastened thereto;

FIG. 13 is a side perspective view of the center rod and removable trocar shown in FIG. 11 separated one from the other;

FIG. 16 is a side cross-sectional view taken through the retaining clip of the anvil assembly and removable trocar of the anvil assembly shown in FIG. 15;

FIG. 17 is an enlarged view of the indicated area of detail shown in FIG. 16;

FIG. 18 is a side cross-sectional view taken through the pivot member of the anvil head assembly of the anvil assembly shown in FIG. 15;

FIG. 19 is a side perspective view from the proximal end of the anvil assembly shown in FIG. 18 with the removable trocar removed;

FIG. 36 is a perspective view from the front of the distal end of the surgical stapling device shown in FIG. 35 with an anvil assembly attached thereto;

FIG. 37 is a side cross-sectional view of the distal end of the surgical stapling device shown in FIG. 36;

FIG. 39 is a cross-sectional view taken along section lines 39-39 of FIG. 38;

FIG. 40 is a cross-sectional view taken along section lines 40-40 of FIG. 38;

FIG. 41 is a cross-sectional view taken along section lines 41-41 of FIG. 38;

FIG. 42 is a cross-sectional view taken along section lines 42-42 of FIG. 38;

FIG. 43 is a cross-sectional view taken along section lines 43-43 of FIG. 38;

FIG. 44 is a cross-sectional view taken along section lines 44-44 of FIG. 38;

FIG. 45 is a side perspective view of the surgical stapling device shown in FIG. 38 with the anvil assembly in an approximated position;

FIG. 46 is a side cross-sectional view of the distal end of the surgical stapling device shown in FIG. 45;

FIG. 48 is a side cross-sectional view of the handle assembly of the surgical stapling device shown in FIG. 45;

FIG. 49 is a top horizontal cross-sectional view of a portion of the handle assembly of the surgical stapling device shown in FIG. 45;

FIG. 51 is a side cross-sectional view of a portion of the handle assembly of the surgical stapling device shown in FIG. 45 after the firing trigger has been actuated;

FIG. 52 is a side cross-sectional view of the distal end of the surgical stapling device shown in FIG. 45 after the firing trigger has been actuated;

FIG. 53 is a side view of the handle assembly shown in FIG. 51 with the handle sections removed;

FIG. 54 is an enlarged view of the firing link extension engaging the abutment member of the tactile indicator mechanism of the handle assembly shown in FIG. 53;

FIG. 58 is an enlarged view of the abutment member of the tactile indicator mechanism of the handle assembly shown in FIG. 53 (during unapproximation of the anvil and cartridge assemblies) with the wing of the screw stop, shown in phantom, in engagement with the abutment member;

FIG. 62 is a side cross-sectional view of another embodiment of the presently disclosed surgical stapling device with the anvil assembly removed from the anvil retainer;

FIG. 63 is a side cross-sectional view of the surgical stapling device shown in FIG. 62 with the anvil assembly attached to the anvil retainer in the open position;

FIG. 64 is a side cross-sectional view of the anvil assembly of the surgical stapling device shown in FIG. 63;

FIG. 69 is a top view of the anvil retainer of the surgical stapling device shown in FIG. 65;

FIG. 70 is a side view of the anvil retainer shown in FIG. 69;

FIG. 71 is an enlarged view of the indicated area of detail shown in FIG. 70;

FIG. 93 is a side cross-sectional view of an anvil assembly insertion handle;

FIG. 94 is a side perspective view of the anvil assembly insertion handle shown in FIG. 93;

FIG. 95 is a side cross-sectional view of the anvil assembly insertion handle attached to the anvil assembly shown in FIG. 84;

DETAILED DESCRIPTION OF EMBODIMENTS

Figure 4:
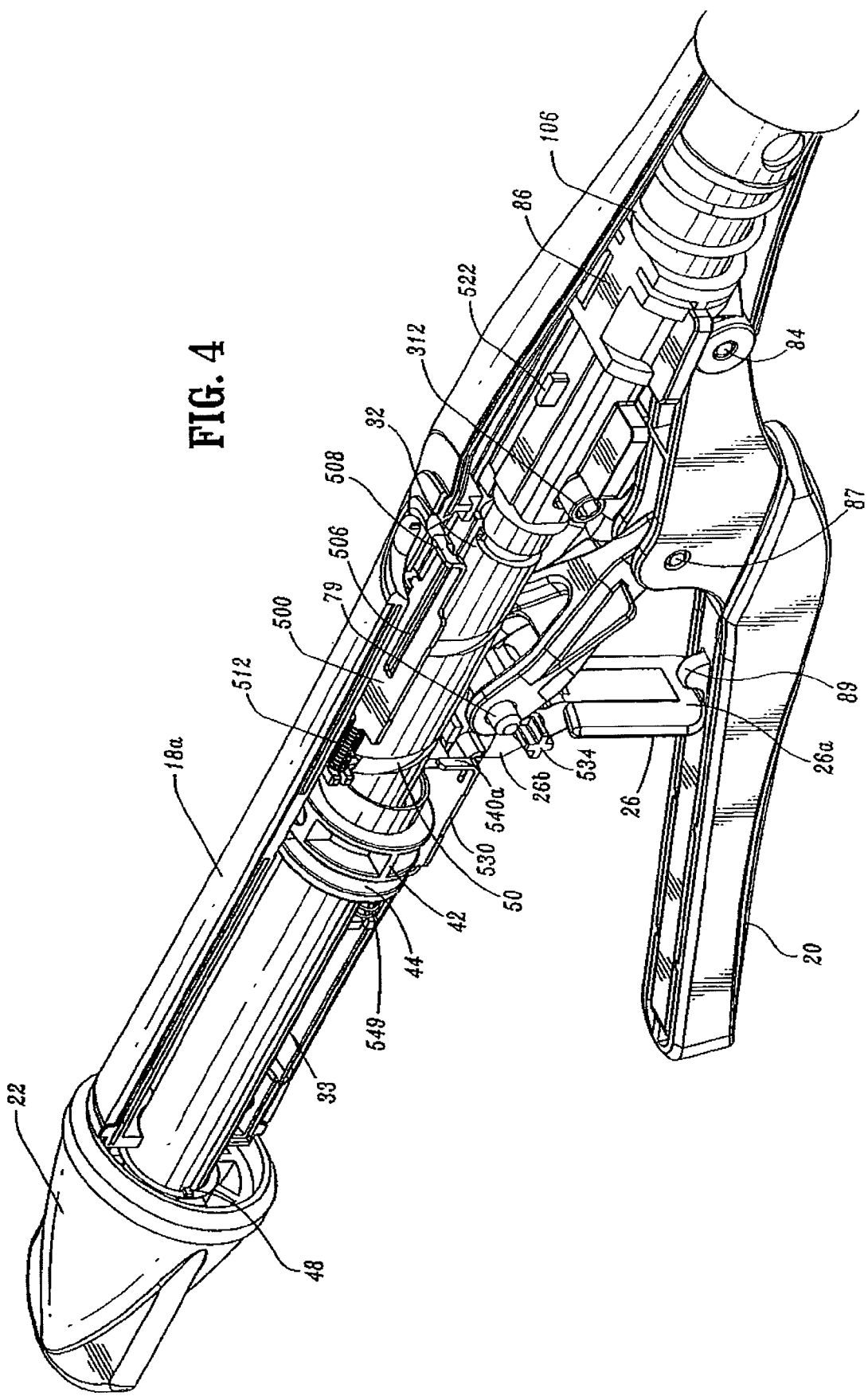
FIG. 4 is a side perspective view from the top of the handle assembly of the surgical stapling device shown in FIG. 1 with a handle section removed.

Embodiments of the presently disclosed surgical stapling device will now be described in detail with reference to the drawings in which like reference numerals designate identical or corresponding elements in each of the several views.

Throughout this description, the term "proximal" will refer to the portion of the instrument closest to the operator and the term "distal" will refer to the portion of the instrument farthest from the operator.

FIGS. 1 and 2 illustrate one embodiment of the presently disclosed surgical stapling device shown generally as 10. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight central body portion. The length, shape and/or the diameter of body portion 14 and head portion 16 may also be varied to suit a particular surgical procedure.

Handle assembly 12 includes a stationary handle 18, a firing trigger 20, a rotatable approximation knob 22 and an indicator 24. Stationary handle 18 may be formed from thermoplastic handle sections 18a and 18b, e.g., polycarbonate, (FIG. 3) which together define a housing for the internal components of handle assembly 12. Handle sections 18a and 18b may be secured together by sonic welding. Alternately, other known securement techniques may be employed including screws, adhesives, snap-fit connectors, etc. The internal components of handle portion 12 will be discussed in detail below. In one embodiment, cushioned and/or resilient slip resistant portions such as a grip (not shown) can be fastened to or included as part of handle sections 18a and 18b and firing trigger 20. The slip resistant grip may be formed over handle sections 18a and 18b and firing trigger 20 using an overmolding procedure and may be formed from Neoprene polychloroprene or rubber. Alternately, other suitable, e.g., elastomeric, materials and joining techniques may be employed. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device has been fired and/or when the device is ready to be fired.

Head portion 16 includes an anvil assembly 30 and a shell assembly 31. Each of these assemblies will be discussed in detail below. Except where otherwise noted, the components of surgical device 10 are formed from thermoplastics including polycarbonates, and metals including stainless steel and aluminum. The particular material selected to form a particular component will depend upon the strength requirements of the particular component. For example, the anvil may be formed from a metal, such as stainless steel, and the stationary handle may be formed from a thermoplastic such as polycarbonate. Alternately, other materials not listed above, which can withstand sterilization procedures, may be used to form components of stapling device 10 provided the materials are suitable for surgical use and meet the strength requirements of the particular component.

Figure 5:
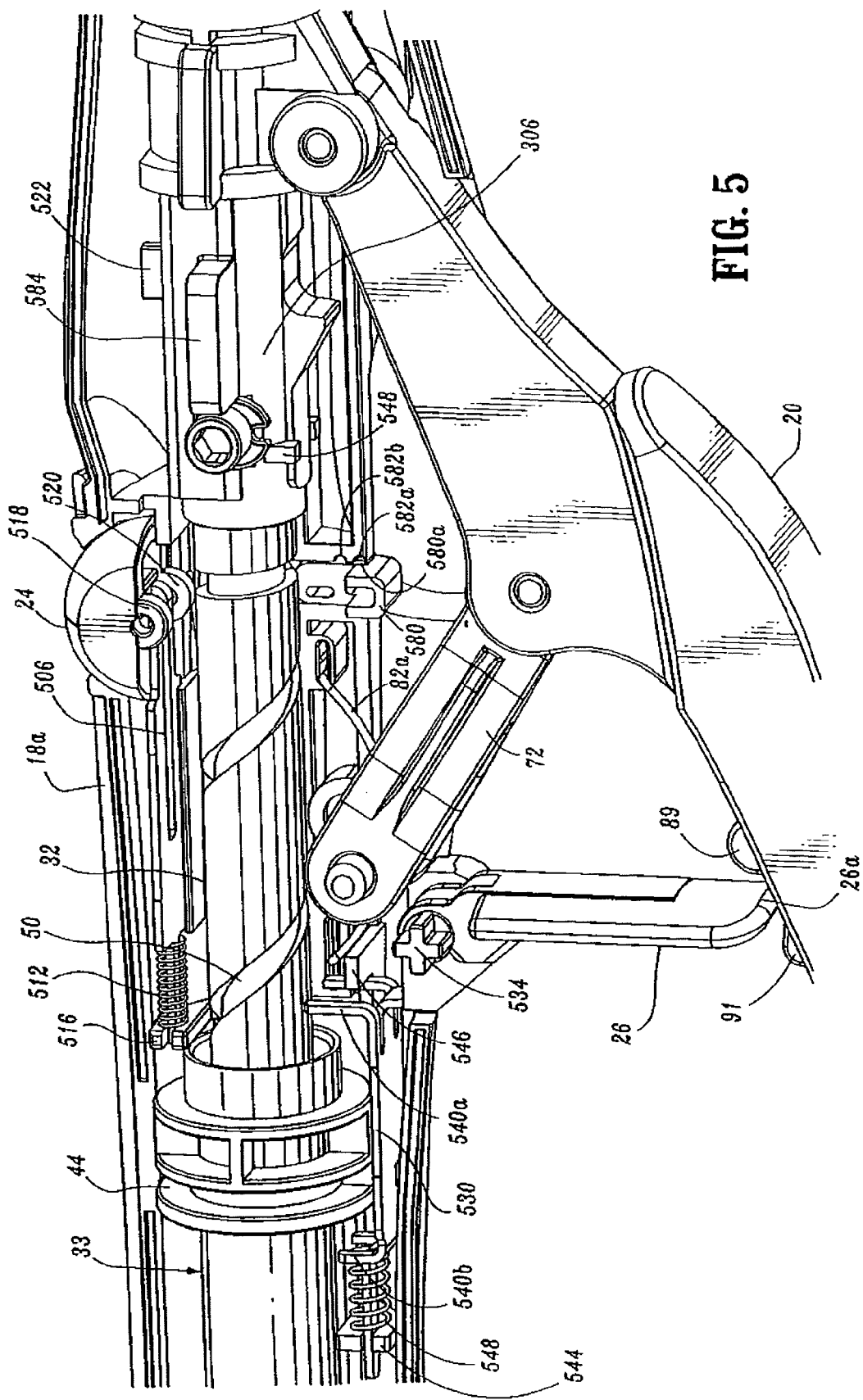
FIG. 5 is a side perspective view from the bottom of the handle assembly of the surgical stapling device shown in FIG. 4.
Figure 6:
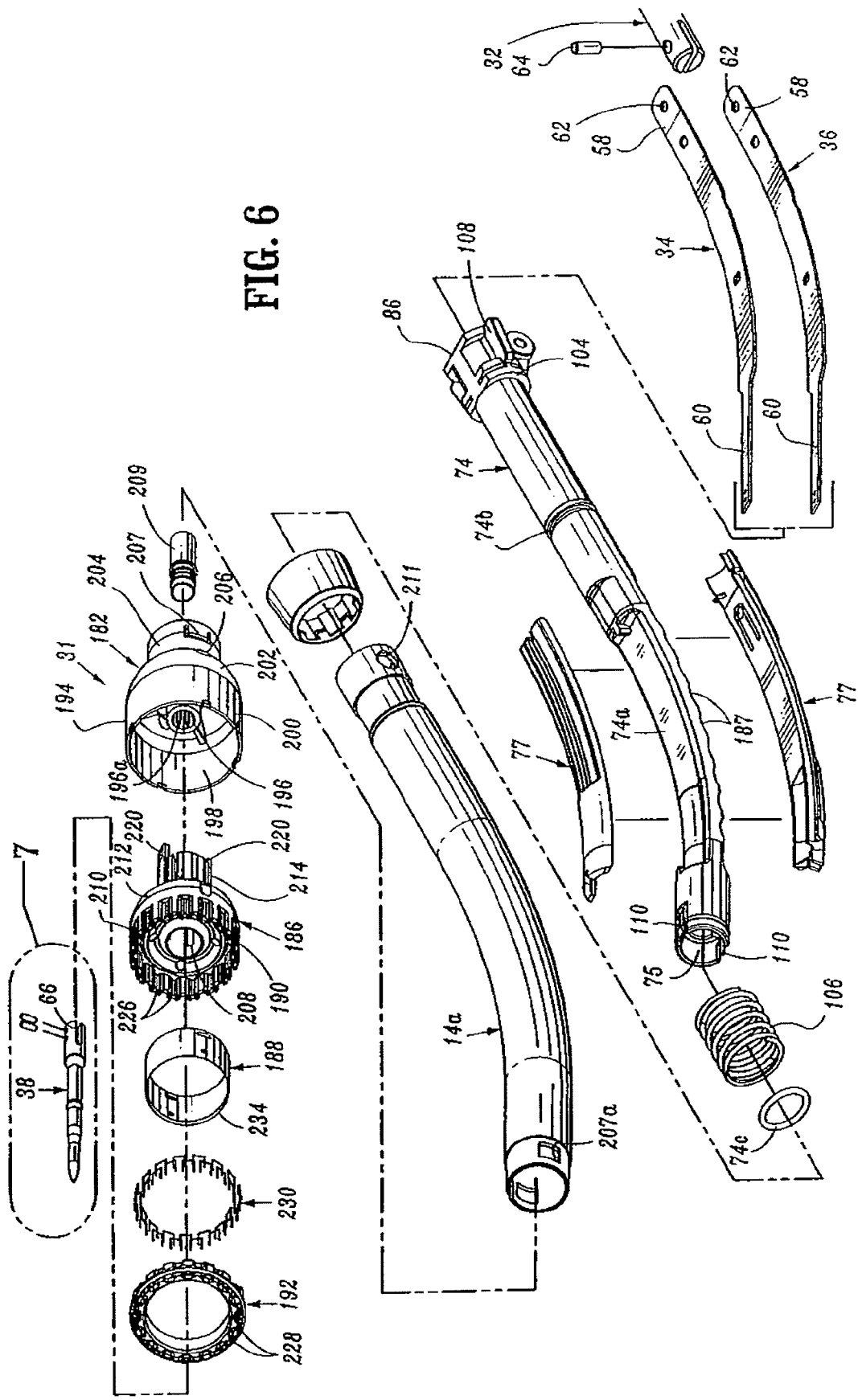
FIG. 6 is a side perspective exploded view of the central body portion and distal head portion of the surgical stapling device shown in FIG. 1.
Figure 9A:
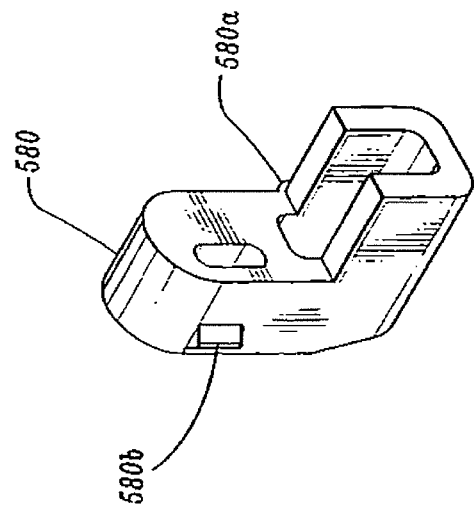
FIG. 9A is a side perspective view from the top of the abutment member of the handle assembly shown in FIG. 3.
Figure 9:
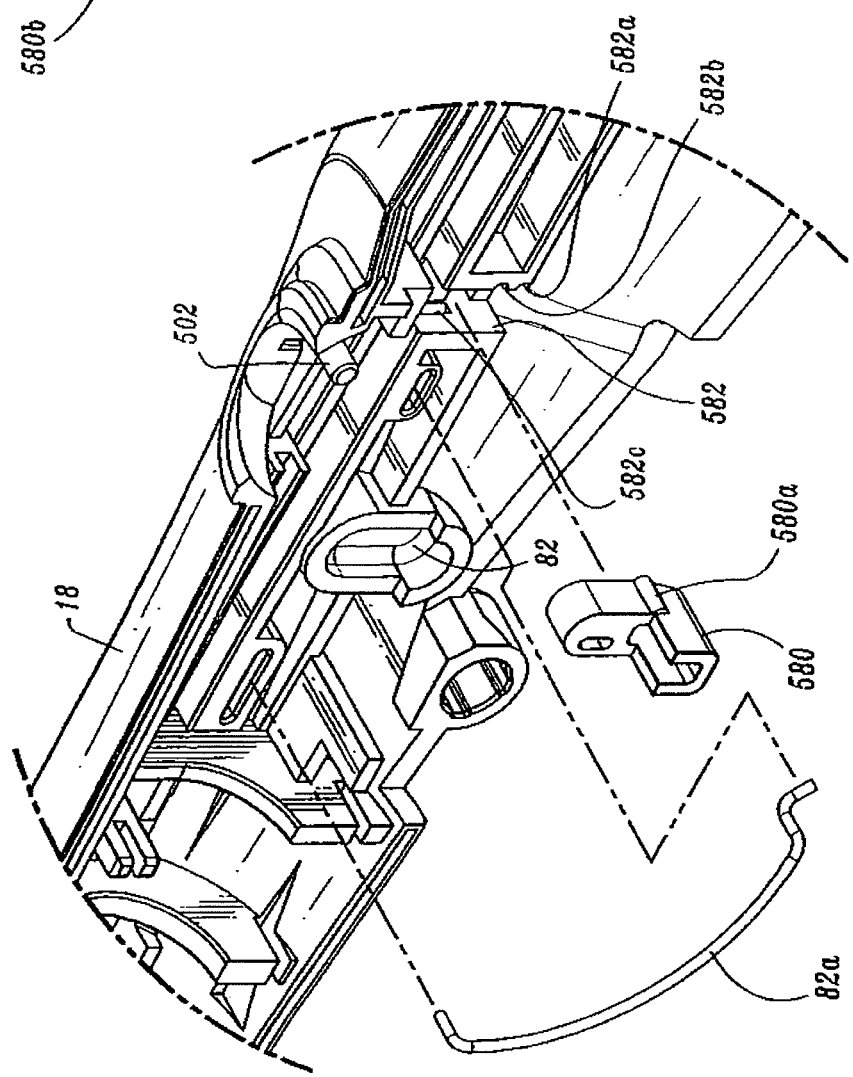
FIG. 9 is an enlarged view of the indicated area of detail shown in FIG. 3.
Figure 14:
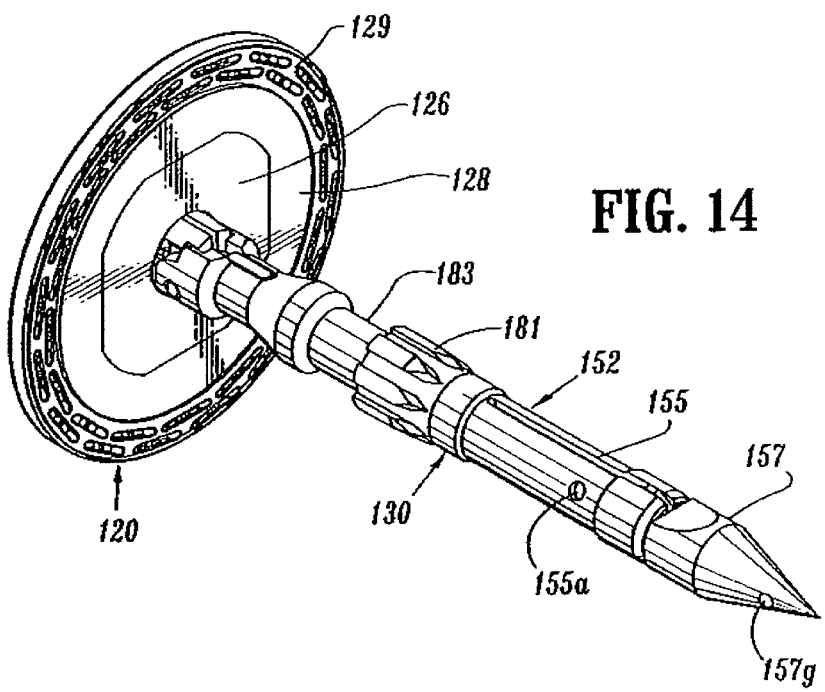
FIG. 14 is a side perspective view from the proximal end of the anvil assembly shown in FIG. 10 with the removable trocar attached thereto.
Figure 15:
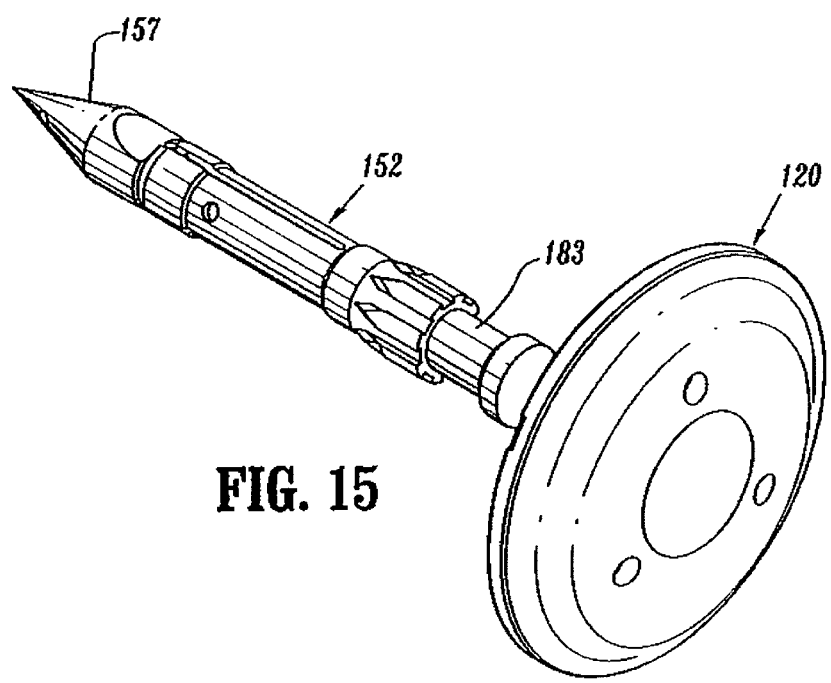
FIG. 15 is a side perspective view from the distal end of the anvil assembly shown in FIG. 14.
Figure 21:
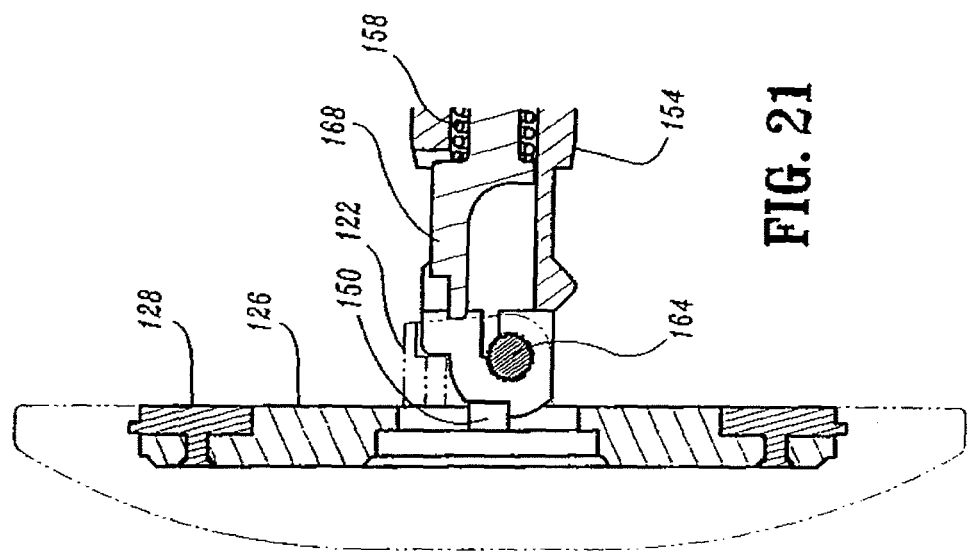
FIG. 21 is a side cross-sectional partial cutaway view of the distal portion of the anvil assembly shown in FIG. 19, with the anvil head in phantom.
Figure 20:
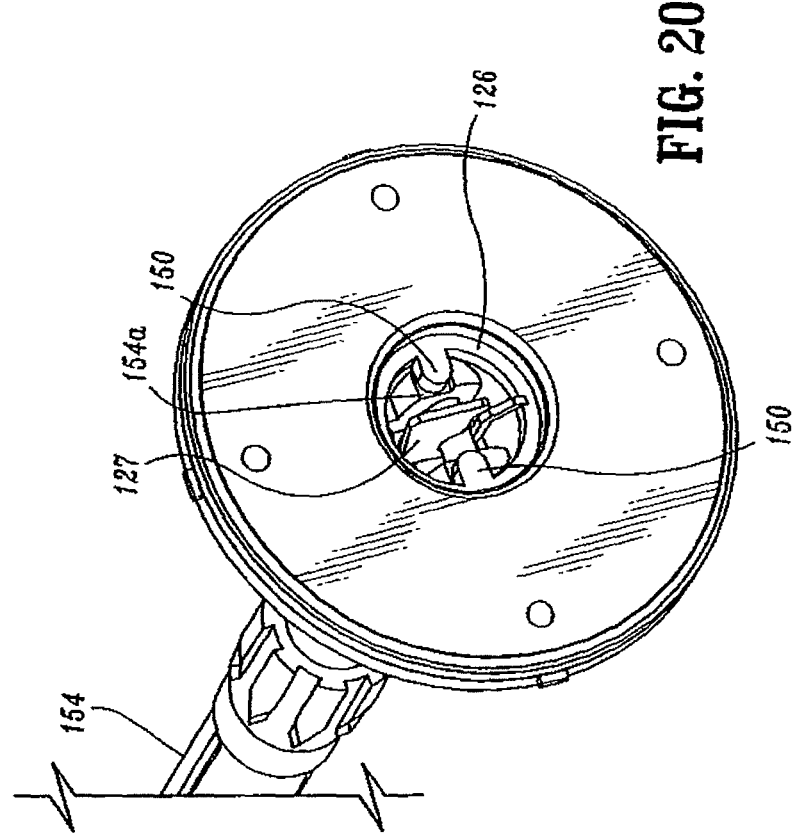
FIG. 20 is a perspective, partial cutaway view from the distal end of the anvil assembly shown in FIG. 19, with the anvil head removed.
Figure 22:
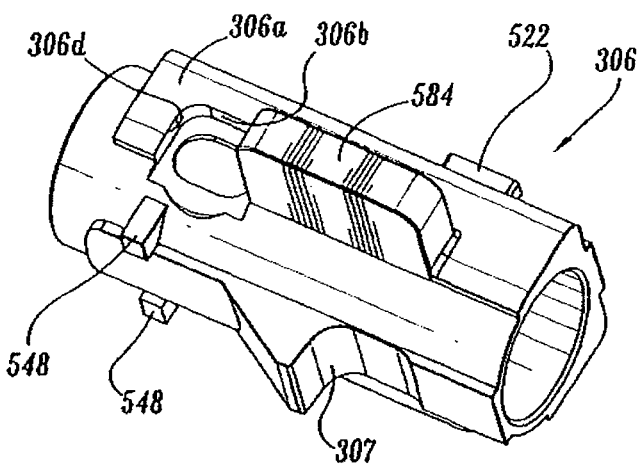
FIG. 22 is a side perspective view from the bottom of the screw stop of the handle assembly shown in FIG. 3.
Figure 23:
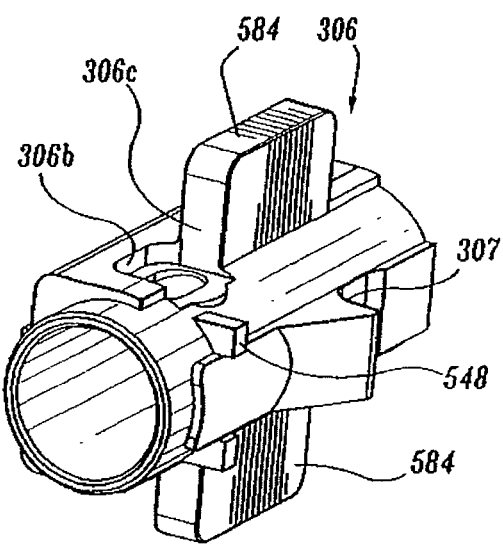
FIG. 23 is a bottom perspective view from the proximal end of the screw stop shown in FIG. 22.
Figure 24:
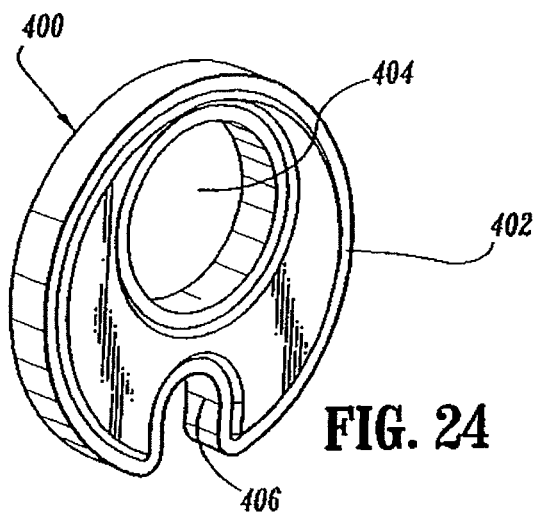
FIG. 24 is a top perspective view of the cam adjustment member of the handle assembly shown in FIG. 3.

FIGS. 3-5 illustrate the internal components of handle assembly 12. The internal components include the proximal components of approximation and firing mechanisms, a firing lockout mechanism and an indicator drive mechanism. FIGS. 6 and 7 illustrate the internal components of elongated body portion 14. These components include the distal components of the approximation and firing mechanisms. Each of these mechanisms will be disclosed in detail hereinbelow.

Approximation Mechanism

Referring to FIGS. 3-8, the approximation mechanism includes approximation knob 22, a rotatable sleeve 33, a drive screw 32, first and second screw extensions 34 and 36 (FIG. 6), and an anvil retainer 38. Rotatable sleeve 33 includes a substantially cylindrical hollow body portion 40 and a substantially cylindrical collar 42 which together define a central bore 33a. Collar 42 has an annular groove 44 formed thereabout and is dimensioned to receive an inwardly extending flange 46 formed on an inner wall of stationary handle 18. Engagement between groove 44 and flange 46 axially fixes sleeve 33 within handle 18 while permitting rotation of sleeve 33 in relation to stationary handle 18. The proximal end of body portion 40 of rotatable sleeve 33 extends through an opening 18b in the proximal end of stationary handle 18. A pair of diametrically opposed elongated ribs 48 are positioned on the outer surface of body portion 40. Approximation knob 22 includes a pair of internal slots 49a positioned to receive ribs 48 of sleeve 33 to rotatably fix sleeve 33 to knob 22, such that rotation of knob 22 causes concurrent rotation of sleeve 33.

The proximal half of screw 32 includes a helical channel 50 and is dimensioned to be slidably positioned within central bore 33a of rotatable sleeve 33. The distal end of screw 32 includes an annular recess 35 dimensioned to receive a seal member 37 (FIG. 3) for providing a fluid tight seal between the outer surface of screw 32 and the inner surface of pusher link 74 (FIG. 6). A pin 52 (FIG. 3) extends radially through body portion 42 of sleeve 33 into helical channel 50. Since sleeve 33 is axially fixed with respect to stationary handle 18, rotation of sleeve 33 about screw 32 causes pin 52 to move along channel 50 of screw 32 to effect axial movement of screw 32 within stationary handle 18.

The distal end of screw 32 includes a transverse slot 54. Top and bottom screw extensions 34 and 36 (FIG. 6) each include a proximally located flexible flat band portion 58 and a distally located flat band portion 60. Alternately, it is envisioned that screw extensions 34 and 36 may have other than a band configuration. For example, screw extensions 34 and 36 may be semi-circular or circular in cross-section. The flexibility of top and bottom screw extensions 34 and 36 permits movement of screw extensions 34 and 36 through curved elongated body portion 14. The proximal end of each band portion 58 includes a hole 62 dimensioned to receive a pin 64 for securing the proximal end of screw extensions 34 and 36 within transverse slot 54 of screw 32. Alternately, other fastening techniques may be used to secure each band portion 58 to screw 32, e.g., welding, crimping, etc. Distally located band portion 60 of each screw extension 34 and 36 is dimensioned to be received within a transverse slot 66 formed in a proximal end of anvil retainer 38 (FIG. 7) to fasten anvil retainer 38 to the distal end of screw extensions 34 and 36. In one embodiment, a pair of pins 66a which extend through the proximal end of anvil retainer 38 and band portions 60 are used to secure screw extensions 34 and 36 to anvil retainer 38. Alternately, band portions 60 can be brazed or welded within slot 66 or other fastening techniques may be used to secure band portions 60 of screw extensions 34 and 36 to anvil retainer 38, e.g., screws, crimping, etc. Anvil retainer 38 includes an annular protrusion 177 (FIG. 7) which is configured to engage the anvil assembly in a manner to be discussed in detail below. Alternately, protrusion 177 need not be annular or may include different attachment structure, e.g., recesses, grooves, etc.

In operation, when approximation knob 22 is manually rotated, rotatable sleeve 33 is rotated about the proximal end of screw 32 to move pin 52 along helical channel 50 of screw 32. Since sleeve 33 is axially fixed to stationary handle 18, as pin 52 is moved through channel 50, screw 32 is advanced or retracted within stationary handle 18. As a result, top and bottom screw extensions 34 and 36, which are fastened to the distal end of screw 32, and anvil retainer 38, which is fastened to the distal end of screw extensions 34 and 36, are moved axially within elongated body portion 14. Since anvil assembly 30 is secured to the distal end of anvil retainer 38, rotation of approximation knob 22 will effect movement of anvil assembly 30 in relation to shell assembly 31 between spaced and approximated positions.

Firing Mechanism

Referring to FIGS. 3-6 and 9, the firing mechanism includes firing trigger 20, a firing link 72 and an elongated pusher link 74 (FIG. 6). Firing trigger 20 includes a body portion 76 and a trigger cover 80. A cushioned gripping surface (not shown) which may be formed of Neoprene polychloroprene or rubber is provided on trigger cover 80. The cushioned gripping surface provides a non-slip cushioned surface to make actuation of device 10 more comfortable and less traumatic to a surgeon. Body portion 76 of trigger 20 is pivotally connected to a coupling member 86 (which is secured to the proximal end of pusher link 74), by a pivot member 84. Coupling member 86 may be formed integrally with pusher link 74 or as a separate element fastened thereto. Firing link 72 has a first end pivotally secured to body portion 76 of trigger 20 by a pivot member 87 and a second end pivotally secured within a vertical slot 82 formed between stationary handle half-sections 18a and 18b of stationary handle 18 by pivot member 79. Pivot member 79 is free to move vertically within slot 82. A spring 82a (FIG. 9) is supported within handle 18 to urge pivot member 79 downwardly towards the bottom of slot 82. Body portion 76 further includes a pair of abutments including an abutment 89 and an abutment 91 which are positioned to engage the distal end 26a (FIG. 4) of trigger lock 26 in a manner to be described in greater detail below to prevent actuation of trigger 20 prior to approximation of device 10.

Coupling member 86 which is supported on the proximal end of elongated pusher link 74 includes a flange 104 (FIG. 6). A spring 106, positioned between an inner wall or abutment within stationary handle 18 and flange 104, biases pusher link 74 proximally to a retracted, non-fired position. A pair of wings 108 extend radially outwardly from coupling member 86. Wings 108 are dimensioned to slide along channel 111 (FIG. 3) formed along the internal walls of stationary handle 18 to maintain proper alignment of pusher link 74 within stationary handle 18 during firing of device 10.

The distal end of pusher link 74 includes a pair of engagement fingers 110 which are dimensioned to lockingly engage with members 220 formed in the proximal end of pusher back 186. Pusher back 186 forms part of shell assembly 31 and will be discussed in greater detail below. Pusher link 74 may be formed from a flexible plastic material and includes a plurality of notches 187 which allow pusher link 74 to bend more easily as it moves through body 14. Pusher link 74 defines a hollow channel 75 for slidably receiving the approximation mechanism. A flat surface or cutout 74a formed in pusher link 74 slidably supports screw extensions 34 and 36 which are positioned in juxtaposed alignment one on top of the other. Spacers 77 are positioned within outer tube 14a adjacent cutout 74a to provide additional support for screw extensions 34 and 36 and pusher link 74 and prevent each component from buckling during actuation. An annular channel 74b is formed about pusher link 74 to receive an O-ring seal 74c. Pusher link 74 is slidably positioned within body portion 14 such that O-ring 74c seals the space between pusher link 74 and an internal wall of outer tube 14a. Operation of the firing mechanism of the device will be described in detail below.

Figure 25:
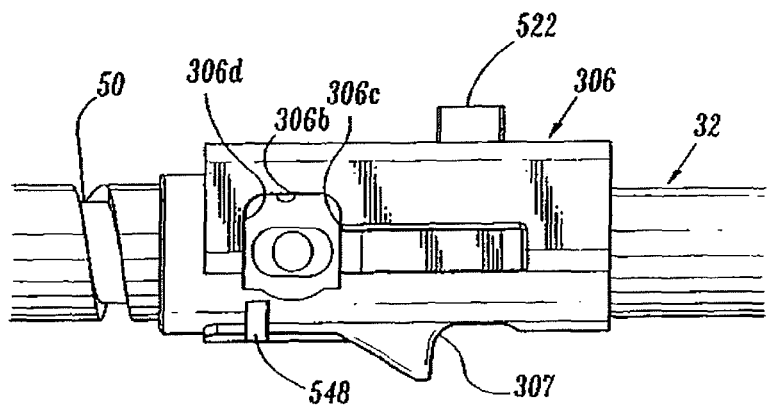
FIG. 25 is a side view of the screw and screw stop of the handle assembly shown in FIG. 3 with the set screw and the cam adjustment member removed.
Figure 26:
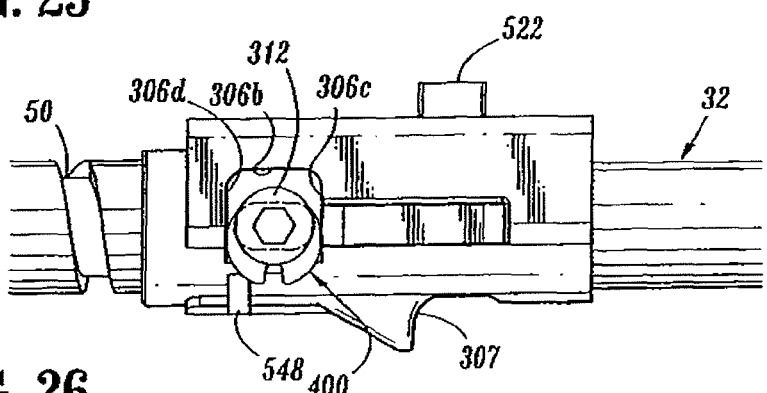
FIG. 26 is a side view of the screw and screw stop shown in FIG. 25 with the set screw and cam adjustment member attached thereto.
Figure 27:
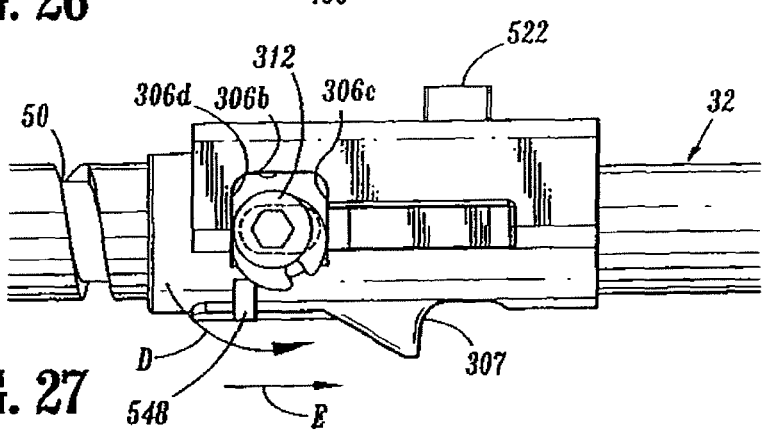
FIG. 27 is a side view of the screw and screw stop shown in FIG. 26 with the cam adjustment screw adjusted to increase the tissue gap.
Figure 28:
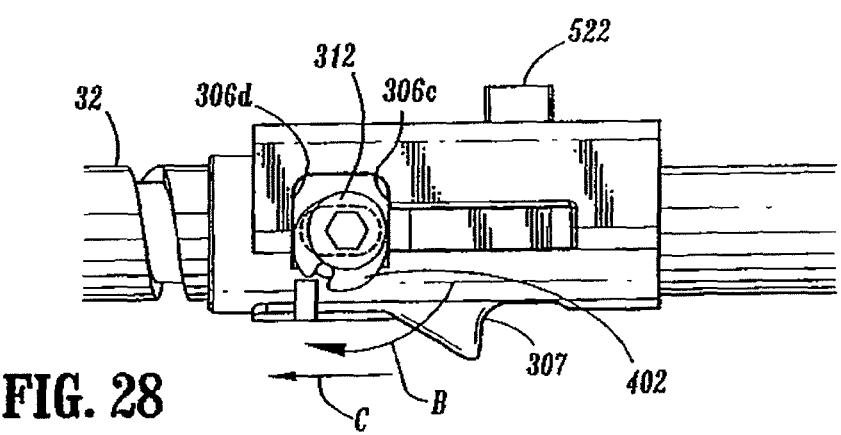
FIG. 28 is a side view of the screw and screw stop shown in FIG. 26 with the cam adjustment screw adjusted to decrease the tissue gap.
Figure 29:
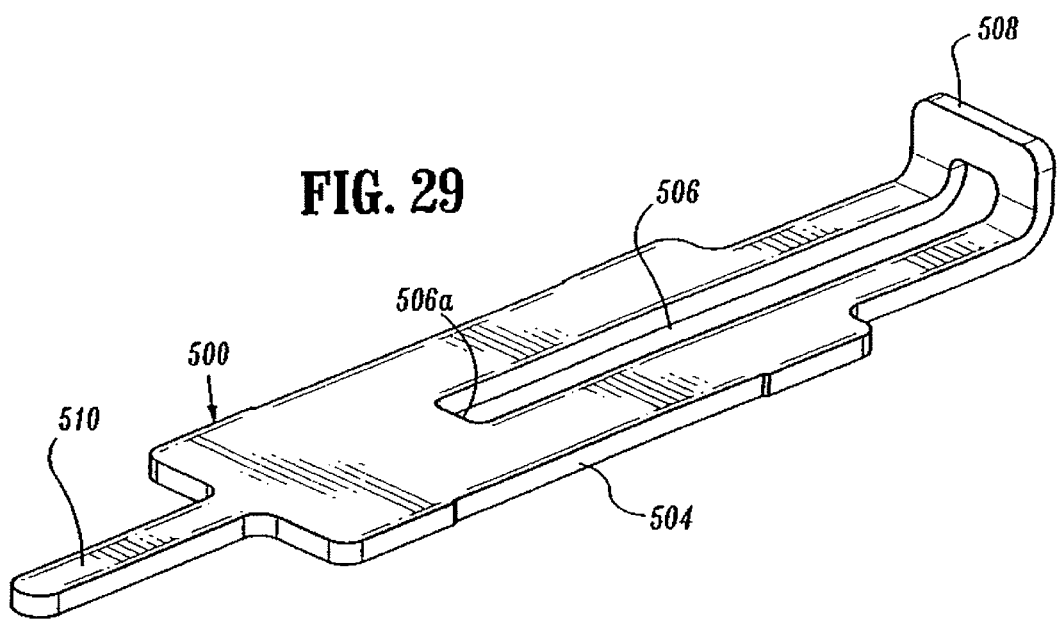
FIG. 29 is a top perspective view from the proximal end of the slide member of the indicator mechanism of the handle assembly shown in FIG. 3.
Figure 30:
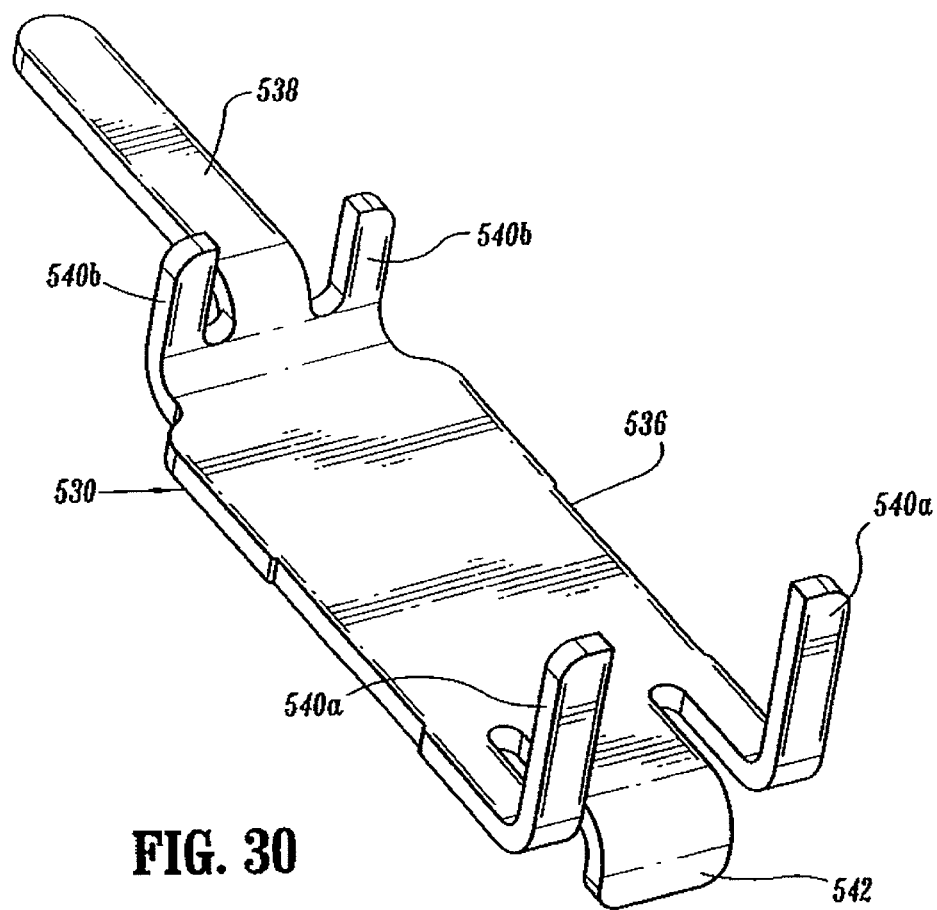
FIG. 30 is a bottom perspective view of the lockout member of the fire lockout mechanism of the handle assembly shown in FIG. 3.
Figure 31:
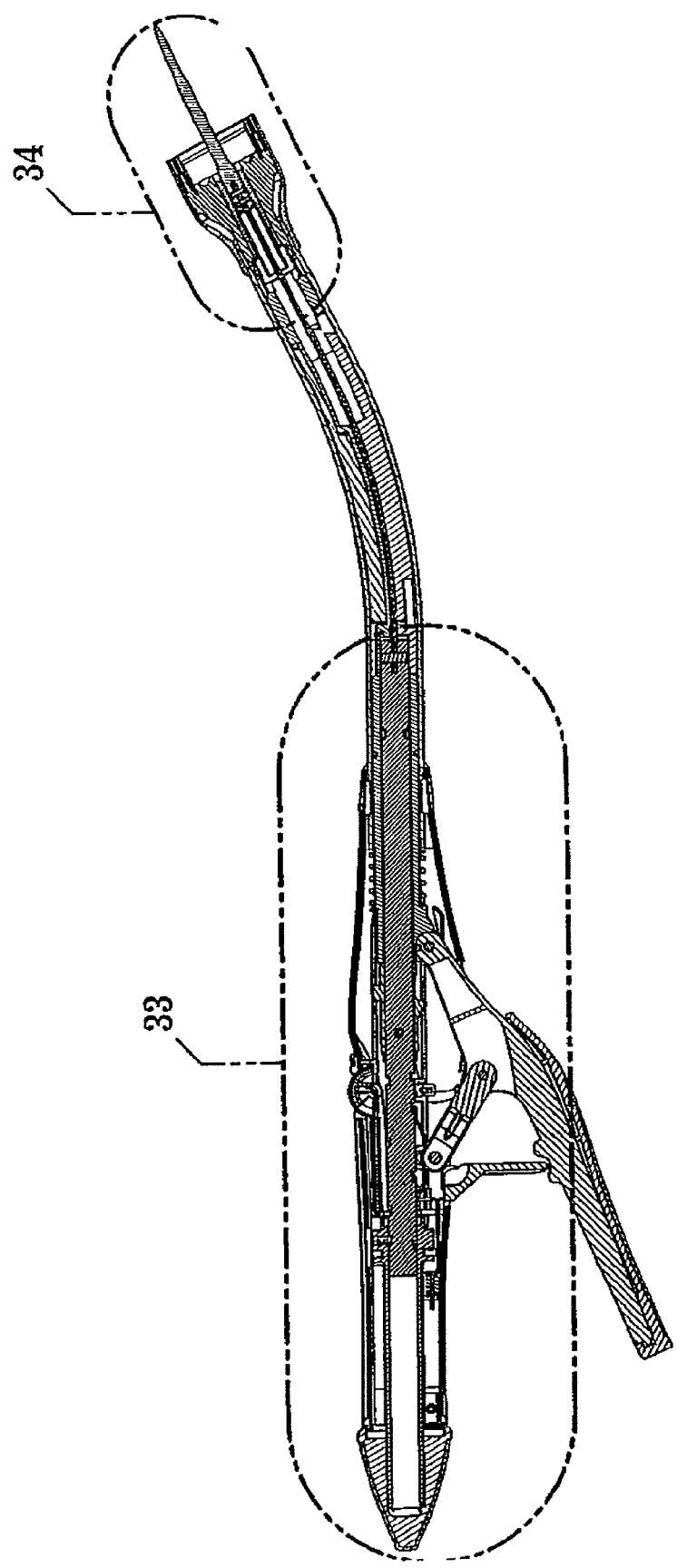
FIG. 31 is a side cross-sectional view of the surgical stapling device shown in FIG. 1 with the anvil assembly removed.
Figure 32:
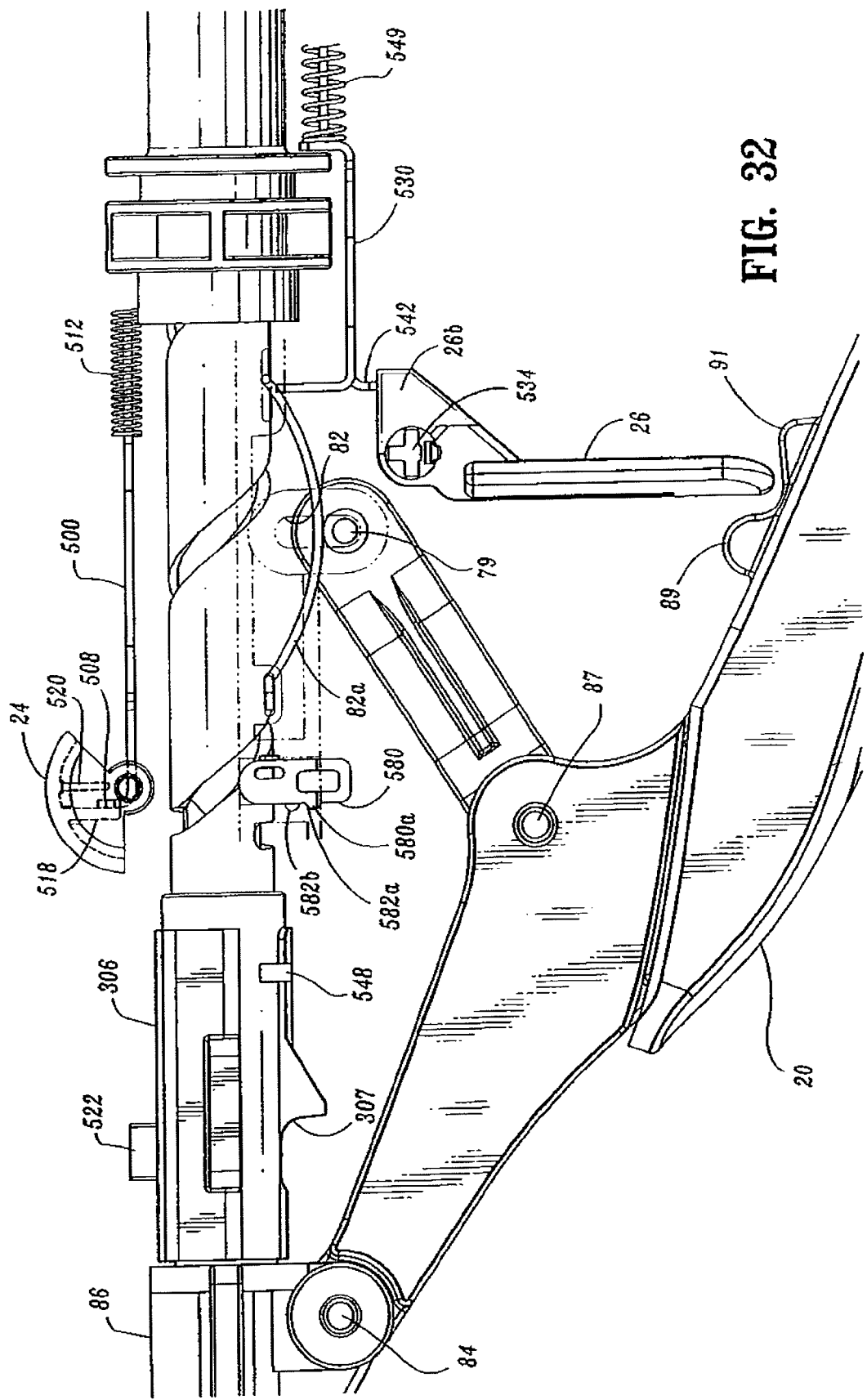
FIG. 32 is a side enlarged view of the handle assembly of the surgical stapling device shown in FIG. 31 with the handle sections removed.
Figure 33:
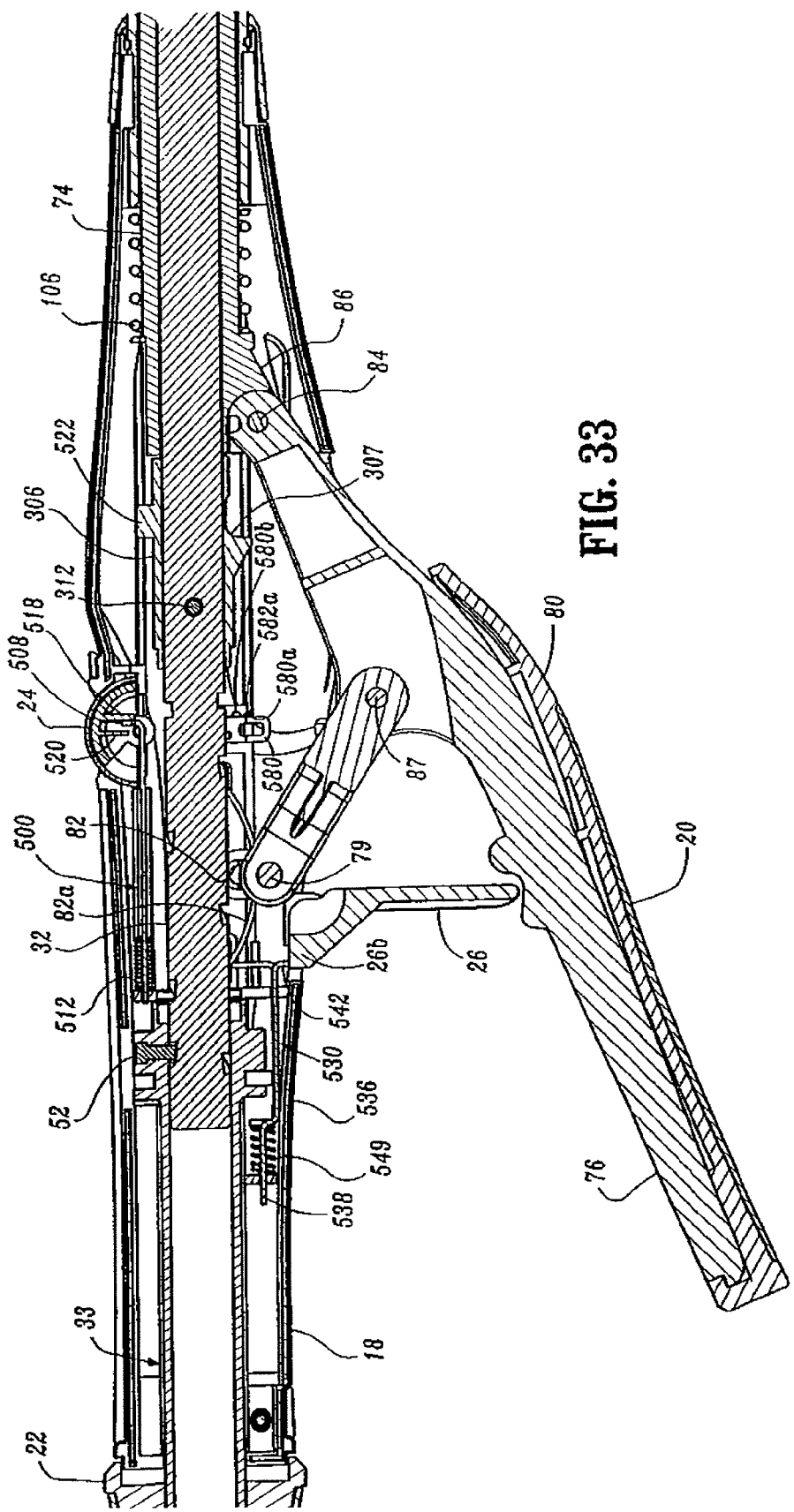
FIG. 33 is an enlarged view of the indicated area of detail shown in FIG. 31.
Figure 34:
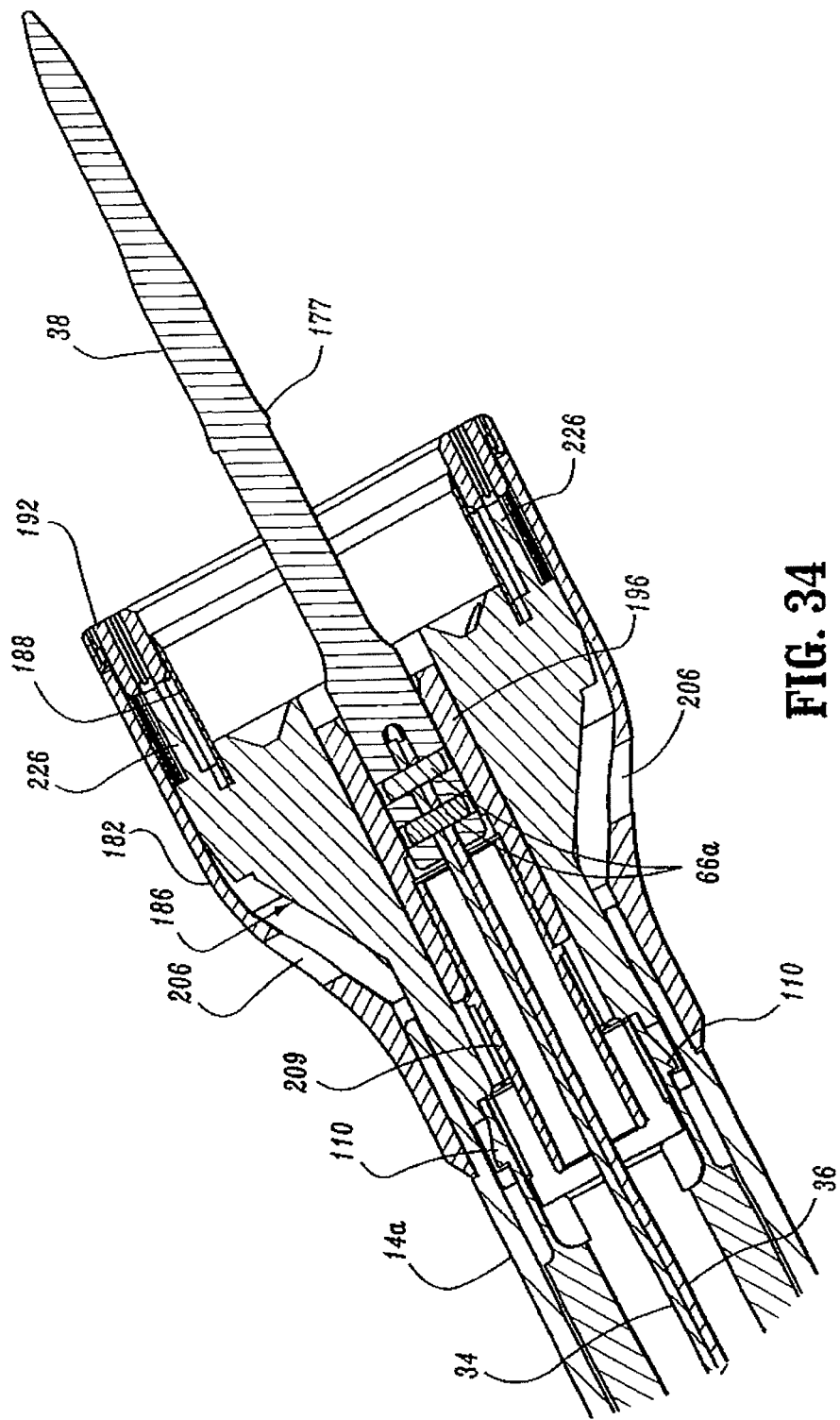
FIG. 34 is an enlarged view of the indicated area of detail shown in FIG. 31.
Figure 35:
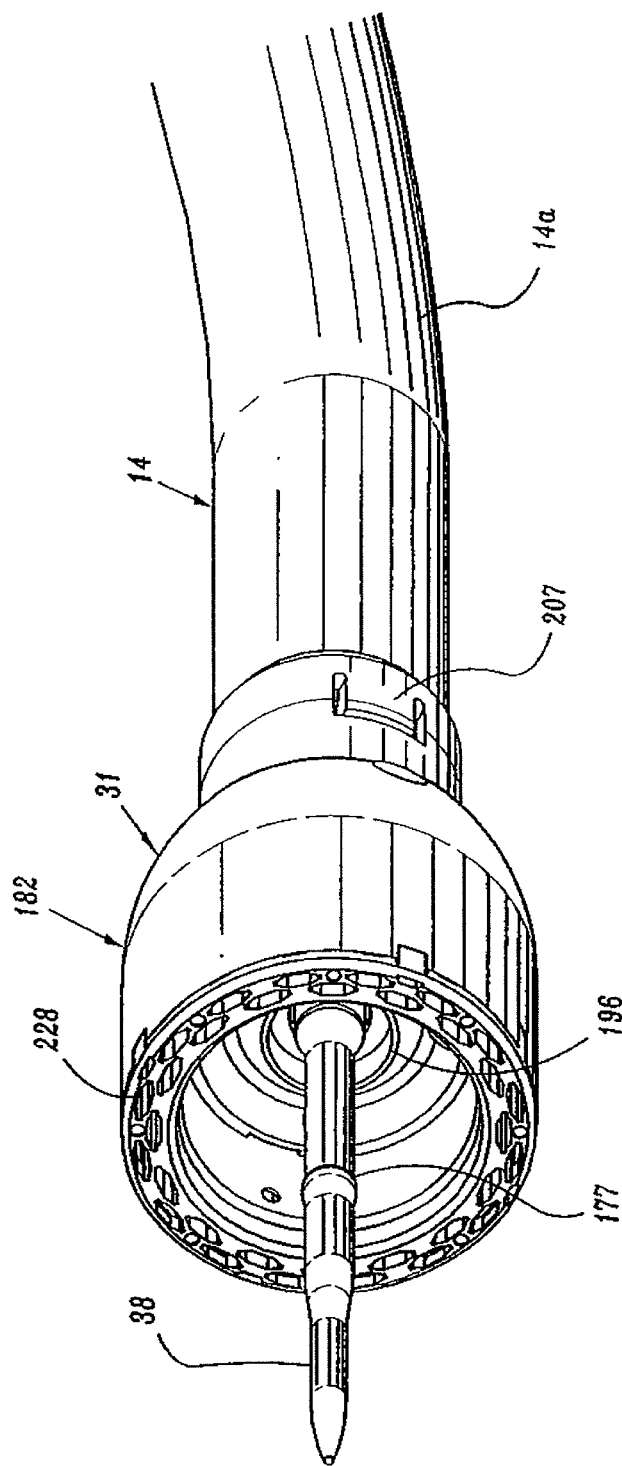
FIG. 35 is a perspective view from the front of the distal end of the surgical stapling device shown in FIG. 31 with the anvil assembly removed.

When firing trigger 20 is actuated, i.e., pivoted about pivot member 84, firing link 72 is moved proximally until pivot member 79 engages an abutment surface 307 (FIGS. 25, 28 and 48) formed on screw stop 306. Screw stop 306 is axially fixed to screw 32. When firing trigger 20 is pushed distally, pusher link 74 is advanced distally against the bias of spring 106. Turning again to FIG. 6, since the distal end of pusher link 74 is connected to pusher back 186, actuation of firing trigger 20 effects advancement of pusher back 186 within shell assembly 31 to eject staples from shell assembly 31 in a manner to be described below.

Anvil Assembly

Referring to FIGS. 10-21, anvil assembly 30 includes an anvil head assembly 120 and an anvil center rod assembly 152. Anvil head assembly 120 includes a post 122, an anvil head 124, a backup plate 126, a cutting ring 128, an anvil 129 and a retaining clip 127. Post 122 is centrally positioned through a bore in anvil head 124. Anvil 129 is supported on anvil head 124 in an outer annular recess 136 and includes a plurality of pockets 140 for receiving and deforming staples. At least one tab 129a extends radially outwardly from anvil 129 and is dimensioned to be received within a cutout 124a formed in anvil head 124. Tab 129a and cutout 124a function to align anvil 129 within annular recess 136. Backup plate 126 includes a central opening 126b which is positioned about post 122 within an inner recess 134 of anvil head 124 between post 122 and annular recess 136. Backup ring 126 includes a raised platform 126a. Cutting ring 128 includes an opening 128a having a configuration substantially the same as platform 126a. Opening 128a is positioned about platform 126a to rotatably fix cutting ring 128a on backup ring 126. In one embodiment, cutting ring 128 is formed from polyethylene and is fixedly secured to backup plate 126 using, for example, an adhesive. Backup ring 126 may be formed from a harder material such as a metal. Alternately other materials of construction may be used to construct plate 126 and ring 128. Cutting ring 128 and backup plate 126 are slidably mounted about post 122. Backup plate 126 includes a pair of inwardly extending tabs 150 which will be described in further detail below. Cutting ring 128 includes tabs 128b which are received within cutouts 124b formed in anvil head 124 to properly align backup ring 126 and cutting ring 128 within anvil head 124.

Anvil center rod assembly 152 includes anvil center rod 154, a plunger 156 and plunger spring 158. A first end of center rod 154 includes a transverse throughbore 160 which is offset from the central longitudinal axis of center rod 154. Post 122 of anvil head assembly 120 also includes a transverse throughbore 162. A pivot member 164 pivotably secures post 122 to center rod 154 such that anvil head assembly 120 is pivotably mounted to anvil center rod assembly 152. Plunger 156 is slidably positioned in a bore 154b (FIG. 16) formed in the first end of center rod 154. Plunger 156 includes an engagement finger 168 which is offset from the pivot axis of anvil head assembly 120 and biased into engagement with the base 122a of post 122 by plunger spring 158 to urge anvil head assembly 120 to a pivoted position orthogonal to center rod 154. In a prefired position, tabs 150 formed on backup plate 126 engage a top surface 154a (FIG. 20) of center rod 154 to prevent anvil head assembly 120 from pivoting about pivot member 164. As device 10 is fired, backup plate 126 and cutting ring 128 are moved deeper into anvil recess 134 of anvil head 124 about post 122 (FIG. 21) by knife 188 (FIG. 6) in a manner to be described in further detail below. Movement of backup plate 126 and cutting ring 128 into anvil recess 134 moves tabs 150 out of engagement with top surface 154a of center rod 154 to permit plunger 156 to pivot anvil head assembly 120 about pivot member 164.

A retainer clip 127 is positioned in a transverse slot 122c formed in post 122 and includes a pair of outwardly biased flexible arms 127a and 127b. Arm 127b includes a recess 127c dimensioned to receive pivot pin 164 (FIG. 17). Prior to firing device 10, arms 127a and 127b are deformed inwardly by backup plate 126 (FIG. 17). After device 10 has been fired and backup plate 126 has been pushed deeper into anvil head 124 by knife 188, flexible arms 127a and 127b spring outwardly to a position in front of backup plate 126. In this position, arms 127a and 127b prevent cutting ring 128 and backup plate 126 from sticking to knife 188 when anvil assembly 30 is unapproximated.

A second end of center rod 154 includes a bore 170 defined by a plurality of flexible arms 155. Bore 170 is dimensioned to receive a removable trocar 157 (FIG. 12). Flexible arms 155 each include an opening 155a dimensioned to receive a projection 157d formed on removable trocar 157 to releasably secure trocar 157 to center rod 154 (FIG. 13). The distal ends of each of flexible arms 155 include an internal shoulder 155b dimensioned to releasably engage anvil retainer 38 (FIG. 6) in a manner to be discussed in detail below. A plurality of splines 181 (FIG. 10) are formed about center rod 154 and are dimensioned to be received within grooves 196a (FIG. 6) in shell assembly 31 to align anvil assembly 30 with shell assembly 31 during approximation of the anvil and shell assemblies. Center rod 154 also includes an annular recessed portion 183 to facilitate grasping of anvil assembly 30 by a surgeon with a grasper.

Turning again to FIG. 12-15, removable trocar 157 includes a trocar tip 157a, a body portion 157b and a cantilevered arm 157c. Projection 157d is positioned on the end of cantilevered arm 157c. Arm 157c is deflectable downwardly, i.e., radially inwardly, in the direction indicated by arrow "A" in FIG. 13 to facilitate insertion of body portion 157b into bore 170 of center rod 154. Splines 157e are provided on body portion 157b to properly align trocar 157 within bore 170 of center rod 154. Arm 157c biases projection 157d outwardly such that when projection 157d passes beneath opening 155a in center rod 154, projection 157d snaps into opening 155a to releasably secure removable trocar 157 to center rod 154. A tab 157f is positioned on arm 157c and can be depressed to facilitate removal of trocar 157 from center rod 154. Trocar tip 157a includes a throughbore 157g dimensioned to receive a suture (not shown) to facilitate locating and removal of trocar 157 within and from the human body. Although illustrated as having a sharpened tip, other trocar tip configurations are envisioned, e.g., blunt.

Shell Assembly

Referring to FIG. 6, shell assembly 31 includes a shell 182, a pusher back 186, a cylindrical knife 188, and a staple guide 192. Shell 182 includes an outer housing portion 194 and an inner guide portion 196 having grooves 196a for mating with splines 181 on anvil center rod 154 (FIG. 10). Outer housing portion 194 defines a throughbore 198 having a distal cylindrical section 200, a central conical section 202 and a proximal smaller diameter cylindrical section 204. A plurality of openings 206 may be formed in conical section 202. Openings 206 are dimensioned to permit fluid and tissue passage during operation of the device. A pair of diametrically opposed flexible engagement members 207 are formed on proximal cylindrical section 204 of shell 182. Engagement members 207 are positioned to be received in openings 207a formed on the distal end of outer tube 14a to secure shell 182 to elongated body 14. A pair of openings 211 formed in the proximal end of outer tube 14a are dimensioned to receive protrusions (not shown) formed on the internal wall of stationary handle 18 (FIG. 1) to facilitate attachment of tube 14a to handle portion 12.

Turning again to FIG. 6, pusher back 186 includes a central throughbore 208 which is slidably positioned about inner guide portion 196 of shell 182. Pusher back 186 includes a distal cylindrical section 210 which is slidably positioned within distal cylindrical section 200 of shell 182, a central conical section 212 and a proximal smaller diameter cylindrical section 214. The proximal end of pusher back 186 includes members 220 which are configured to lockingly engage with resilient fingers 110 of pusher link 74 to fasten pusher link 74 to pusher back 186 such that a distal face of pusher link 74 abuts a proximal face of pusher back 186.

The distal end of pusher back 186 includes a pusher 190. Pusher 190 includes a multiplicity of distally extending fingers 226 dimensioned to be slidably received within slots 228 formed in staple guide 192 to eject staples 230 therefrom. Cylindrical knife 188 is frictionally retained within the central throughbore of pusher back 186 to fixedly secure knife 188 in relation to pusher 190. Alternately, knife 188 may be retained within pusher back 186 using adhesives, crimping, pins, etc. The distal end of knife 188 includes a circular cutting edge 234.

In operation, when pusher link 74 is advanced distally in response to actuation of firing trigger 20, as will be described below, pusher back 186 is advanced distally within shell 182. Advancement of pusher back 186 advances fingers 226 through slots 228 of staple guide 192 to advance staples 230 positioned within slots 228 and eject staples 230 from staple guide 192 into staple deforming pockets 140 of anvil 129 (FIG. 11). Since knife 188 is secured to pusher back 186, knife 188 is also advanced distally to core tissue as will be described in more detail below.

A rigid bushing 209 is supported in the proximal end of inner guide portion 196 of shell 182. Bushing 209 defines a throughbore dimensioned to slidably receive anvil retainer 38 and center rod 154 (FIG. 10) of anvil assembly 30. Bushing 209 provides lateral support for flexible arms 155 of center rod 154 when the anvil assembly 30 has been approximated to prevent disengagement of anvil assembly 30 from anvil retainer 38. In the unapproximated position, flexible arms 155 of center rod 154 are positioned externally of bushing 209 to permit removal of anvil assembly 30 from retainer 38.

Cam Adjustment Mechanism

Referring to FIGS. 8 and 22-28, a cam adjustment member 400 is secured by set screw 312 onto a sidewall 306a of screw stop 306 within a recess 306b formed in sidewall 306a. Cam adjustment member 400 includes a circular disc 402 having a throughbore 404. Throughbore 404 is eccentrically formed through disc 402 and is dimensioned to receive set screw 312. A smaller notch or hole 406 is also formed in disc 402 and is dimensioned to receive the tip of an adjustment tool (not shown). Recess 306b (FIG. 22) includes a forward abutment shoulder or surface 306c (FIG. 23) and a rear abutment surface 306d and is dimensioned to receive disc 402 such that the outer edge of disc 402 abuts forward and rear abutment surfaces 306c and 306d.

Set screw 312 extends through disc 402 and screw stop 306 and is received in a threaded bore 32a in screw 32 to secure screw stop 306 in position on screw 32. Cam adjustment member 400 functions to adjust the axial position of screw stop 306 on screw 32. More specifically, set screw 312 can be loosened to allow disc 402 to rotate within recess 306b of screw stop 306 while still remaining fixed to screw 32. Since disc 402 is eccentrically mounted about screw 32 and engages forward and rear abutment surfaces 306c and 306d of recess 306b, rotation of disc 402 about fixed set screw 312 will urge screw stop 306 axially along screw 32 to adjust the axial position of screw stop 306 on screw 32. For example, when disc 402 is rotated in a clockwise direction (as viewed in FIG. 28) identified by arrow "B", screw stop 306 will be moved axially in relation to screw 32 in the direction indicated by arrow "C" in response to engagement between the outer edge of disc 402 and rear shoulder 306d of recess 306b. Conversely, when disc 402 is rotated in a counter-clockwise direction (as viewed in FIG. 27), identified by arrow "D", screw stop 306 will be moved axially in relation to screw 32 in the direction indicated by arrow "E" in response to engagement between the outer edge of disc 402 and forward shoulder 306c of recess 306b.

When stapling device 10 is in a fully approximated position (as can be seen for instance in FIG. 65), i.e., anvil assembly 30, 640 and shell assembly 31, 605 are brought into juxtaposed alignment to define a tissue receiving clearance, screw stop 306 (FIG. 47) abuts against body portion 42 of the rotatable sleeve 33, i.e., sleeve 33 functions as a stop for the approximation mechanism. In this position, anvil assembly 30 and shell assembly 31 are spaced slightly to define a tissue receiving clearance. By providing cam adjustment member 400, the tissue receiving clearance can be selectively adjusted to be within a desired range by adjusting the position of screw stop 306 on screw 32. In one embodiment, cam adjustment member 400 permits adjustment of the tissue receiving clearance of ±0.045 inches, although greater or lesser adjustment capabilities are also envisioned. Typically, adjustments to the tissue receiving clearance will be made by the device manufacturer. Alternately, a hole or opening (not shown) may be provided in handle portion 12 (FIG. 1) to provide direct access to adjustment member 400 to allow for adjustment of the tissue receiving clearance at the surgical site.

Indicator Mechanism

Referring to FIGS. 3-5, 9, 22, 29 and 33, the indicator mechanism includes indicator 24, lens cover 24a and slide member 500. Indicator 24 is pivotally supported about a pivot member 502 which may be formed monolithically with handle sections 18a and 18b. Lens cover 24a is positioned above indicator 24 and may be formed of magnification material to facilitate easy visualization of indicator 24. Slide member 500 (FIG. 29) includes a body portion 504 having an elongated slot 506 formed therein, a distal abutment member or upturned lip portion 508, and a proximal extension 510. Slide member 500 is slidably positioned between handle sections 18a and 18b. Proximal extension 510 is slidably supported within stationary handle 18 by support structure 516 (FIG. 5). A biasing member 512, e.g., a coil spring, is positioned in compression about proximal extension 510 between support structure 516 and body portion 504 of slide member 500 to urge slide member 500 distally within stationary handle 18. Indicator 24 includes a pair of downwardly extending projections 518 and 520 positioned about pivot member 502. Upturned lip portion 508 of slide member 500 is positioned between projections 518 and 520 and is positioned to engage projections 518 and 520 as it moves within stationary handle 18. In the unfired position of device 10, biasing member 512 urges slide member 500 distally to move lip portion 508 into engagement with projection 518 to pivot indicator to a first position, which provides indication to a surgeon that the device has not been approximated and is not in a fire-ready condition.

As discussed above, screw stop 306 is fixedly attached to screw 32. Screw stop 306 includes a first engagement member 522 which is positioned to travel through slot 506 and engage the proximal end 506a of slot 506 during approximation of the device. When engagement member 522 abuts proximal end 506a (FIG. 29) of slot 506, further approximation of device 10 moves slide plate 500 proximally within stationary handle 18 against the bias of spring 512 such that upturned lip 508 of slide member 500 engages projections 518 & 520 of indicator 24. (See FIG. 48). Engagement between projections 518 & 520 and lip 508 causes indicator 24 to pivot about pivot member 502 to a second position. In the second position, indicator 24 provides indication to a surgeon that the device has been approximated and is now in a fire-ready position.

Fire-Lockout Mechanism

Referring to FIGS. 3-5, 22, 30, 33, and 47, the firing-lockout mechanism includes trigger lock 26 and lockout member 530. Trigger lock 26 is pivotally supported within bores 532 in handle sections 18a and 18b about pivot member 534. In one embodiment, pivot member 534 extends from an upper edge of trigger lock 26 and is T-shaped and frictionally engages the inner wall of bores 532 to prevent free rotation of trigger lock 26. Tip 26a (FIG. 5) of trigger lock 26 is positioned between abutments 89 and 91 on body portion 76 of firing trigger 20 to prevent actuation of trigger 20 when trigger lock 26 is in the locked position. Trigger lock 26 also includes a proximal extension 26b (FIG. 4) which will be discussed in further detail below.

Lockout member 530 (FIG. 30) includes a body portion 536, a proximal extension 538, a pair of front legs 540a, a pair of rear legs 540b, and an abutment member or downturned lip portion 542. Lockout member 530 is slidably positioned between first and second stops 544 and 546 (FIG. 5) formed on an internal wall of handle sections 18a and 18b. Stop 544 is positioned to engage rear legs 540b and stop 546 is positioned to engage front legs 540a. It is also envisioned that a single abutment member may be substituted for each pair of legs. A biasing member 548, e.g., a coil spring, is positioned between stop 544 and body 536 about proximal extension 538 to urge lockout 530 to its distal-most position with legs 540a abutting stop 546. In this position, extension 26b of trigger lock 26 is positioned beneath lip portion 542 of lockout member 530 to prevent pivotal movement of trigger lock 26, and thus prevent actuation of stapling device 10.

As discussed above and as shown in FIG. 47, screw stop 306 is secured to screw 32. A second engagement member or members 548 extend downwardly from screw stop 306. (See FIG. 22). When stapling device 10 is approximated and screw 32 is moved proximally within stationary handle 18, engagement member 548 abuts front legs 540a of lockout member 530 to move lockout member 530 proximally against the bias of member 548 to a position in which lip portion 542 is spaced proximally of extension 26b of trigger lock 26. In this position of lockout member 530, trigger lock 526 can be pivoted to permit firing of stapling device 10.

Tactile Indicator Mechanism

Referring to FIGS. 3, 5, 9 and 9A, a tactile indicator mechanism provided in stationary handle 18 includes an abutment member 580 which is slidably positioned in a vertical slot 582 defined within handle sections 18a and 18b. Abutment member 580 includes a protuberance 580a and a guide rib 580b. Protuberance 580a is dimensioned to be received within one of two detents 582a and 582b formed along a wall of slot 582. Abutment member 580 is movable from a retracted (downward) position, wherein protuberance 580a is positioned within detent 582a, to an extended (upward) position, wherein protuberance 580a is positioned within detent 582b. Engagement between protuberance 580a and detents 582a and 582b retains abutment member 580 in the respective position. Detent 582c, formed in vertical slot 582, is sized to slidably receive guide rib 580b and thereby maintain member 580 in contact with slot 582.

Prior to firing of stapling device 10, abutment member 580 is located in the retracted (downward) position (FIG. 5). When device 10 is fired, an extension 590 of firing link 72 engages abutment member 580 and moves abutment member 580 from its retracted to its extended position. In the extended position, abutment member 580 extends into channel 111 of stationary handle 18.

Figure 57:
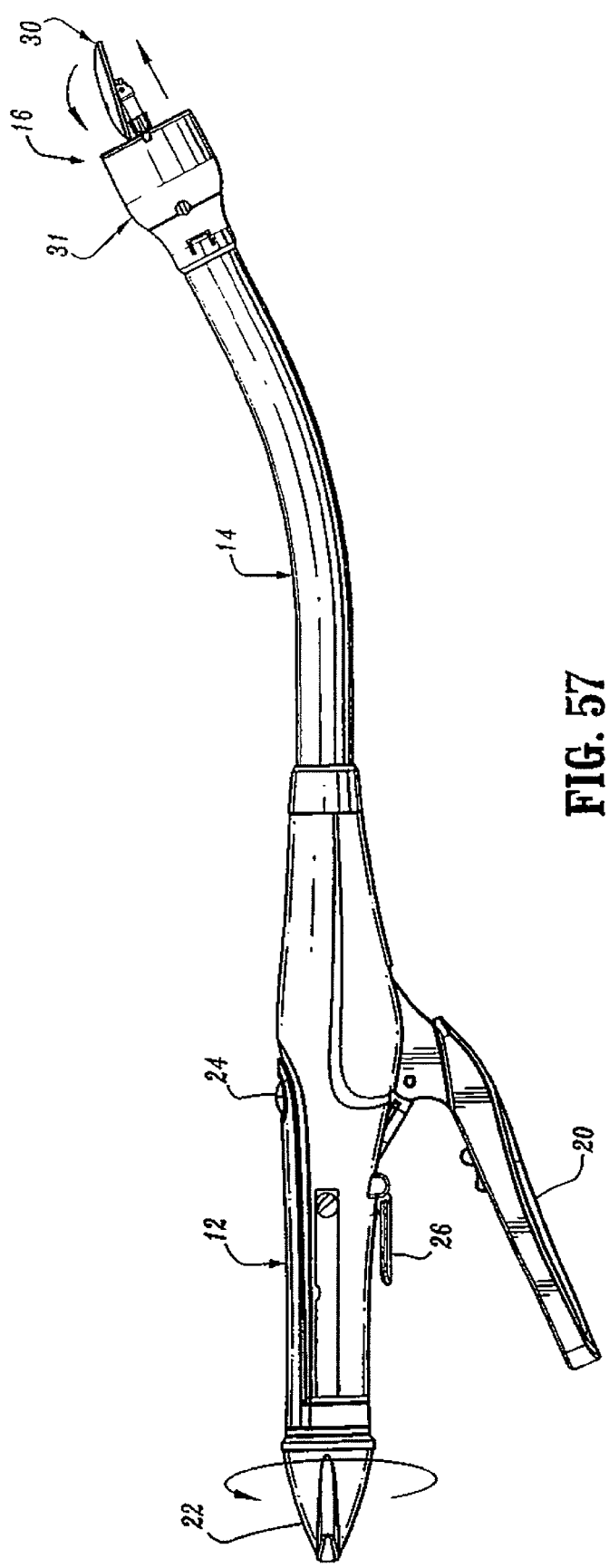
FIG. 57 is a side view of the surgical stapling device shown in FIG. 45 after the anvil assembly and cartridge assembly have been unapproximated a distance sufficient to permit the anvil head assembly to pivot on the anvil center rod.
Figure 59:
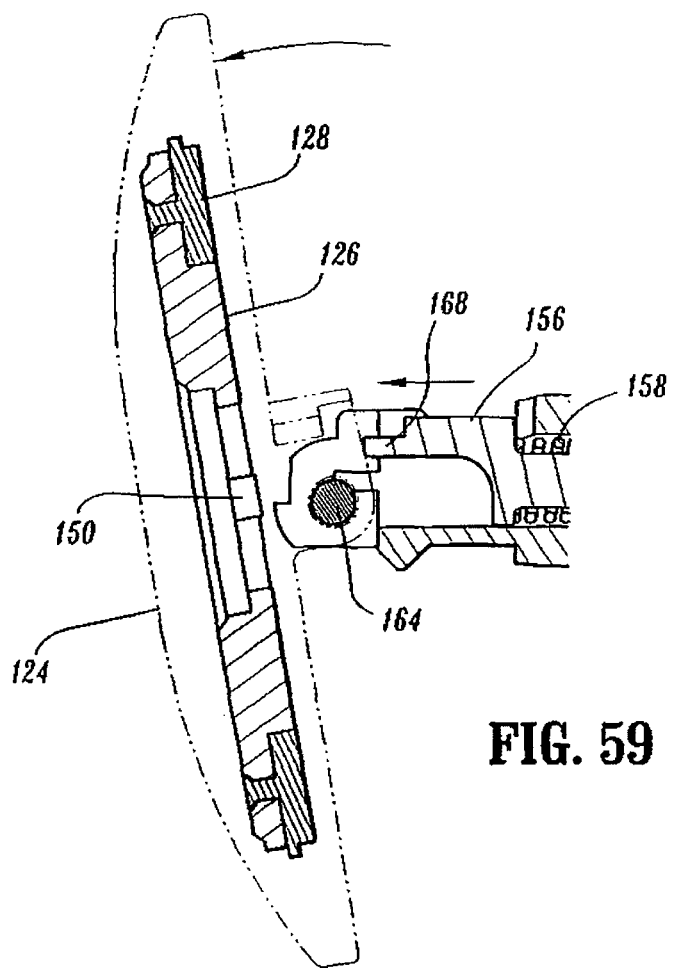
FIG. 59 is a side cross-sectional view of the anvil assembly shown in FIG. 56 as the anvil head assembly begins to tilt.
Figure 60:
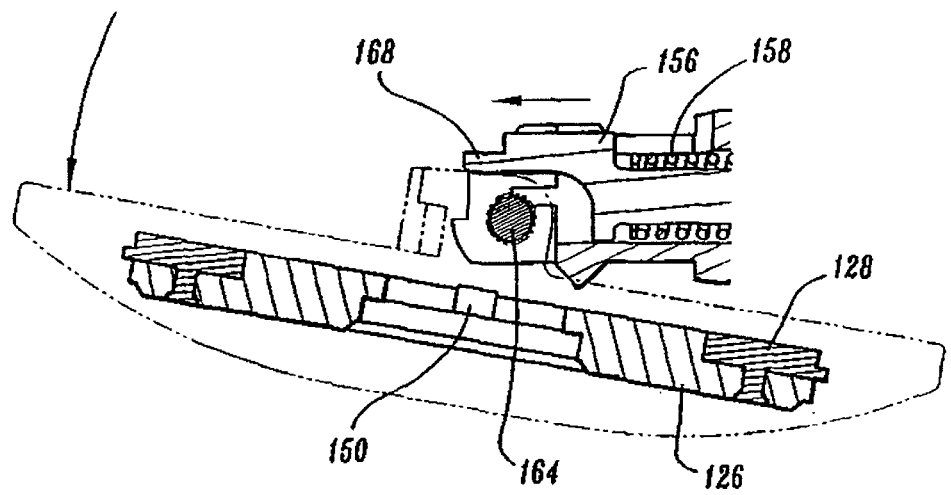
FIG. 60 is a side cross-sectional view of the anvil assembly shown in FIG. 59 with the anvil assembly tilted.
Figure 61:
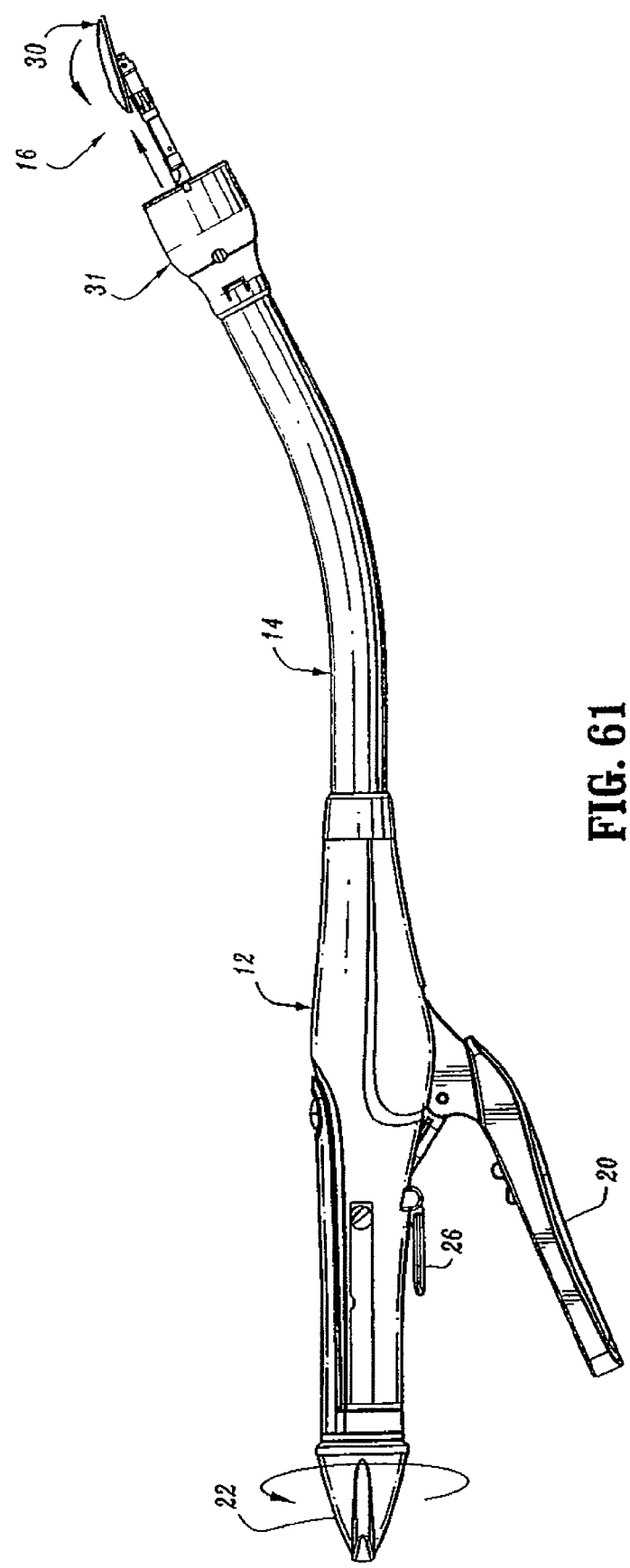
FIG. 61 is a side view of the surgical stapling device shown in FIG. 45 with the anvil head assembly unapproximated and tilted.

Screw stop 306 includes a pair of wings 584 which are slidably positioned in channel 111 of stationary handle 18. After stapling device 10 has been fired, abutment member 580 is positioned within channel 111. During unapproximation of anvil assembly 150 and cartridge assembly 31, one of the wings 584 of screw stop 306 engage abutment member 580 when the device has been unapproximated a sufficient distance to allow anvil assembly 30 to pivot to its reduced profile position (as will be discussed in mere detail below and as can be seen in FIG. 57). Engagement between abutment member 580 and wing 584 of screw stop 306 provides a tactile and/or an audible indication to the surgeon that the anvil assembly 120 has tilted and stapling device 10 can be removed from a patient. If the surgical stapling device is unapproximated further, wing 584 will force abutment member 580 from the extended position back to the retracted position.

Operation

Operation of surgical stapling device 10 will now be described in detail with reference to FIGS. 31-61.

FIGS. 31-35 illustrate surgical stapling device 10 in the unapproximated or open position prior to attachment of anvil assembly 30 to anvil retainer 38. In this position, biasing member 106 is engaged with coupling 86 to urge pusher link 74 to its proximal-most position in which coupling 86 abuts screw-stop 306. Biasing member 512 is engaged with slide member 500 of the indicator mechanism to position slide member 500 in engagement with projection 518 of indicator 24 to pivot indicator 24 in a clockwise direction, as viewed in FIG. 33. Biasing member 549 is engaged with body 536 of lockout member 530 to urge lockout member 530 to its distal-most position, wherein lip portion 542 of lockout member 530 is positioned above extension 26b of trigger lock 26 to prevent movement of trigger lock 26 to the unlocked position. Biasing member 82a engages pivot member 79 to urge pivot member 79 to the base of vertical slot 82. Tactile indicator 580 is in the retracted or downward position with protrusion 580a positioned with detent 582a.

Figure 38:
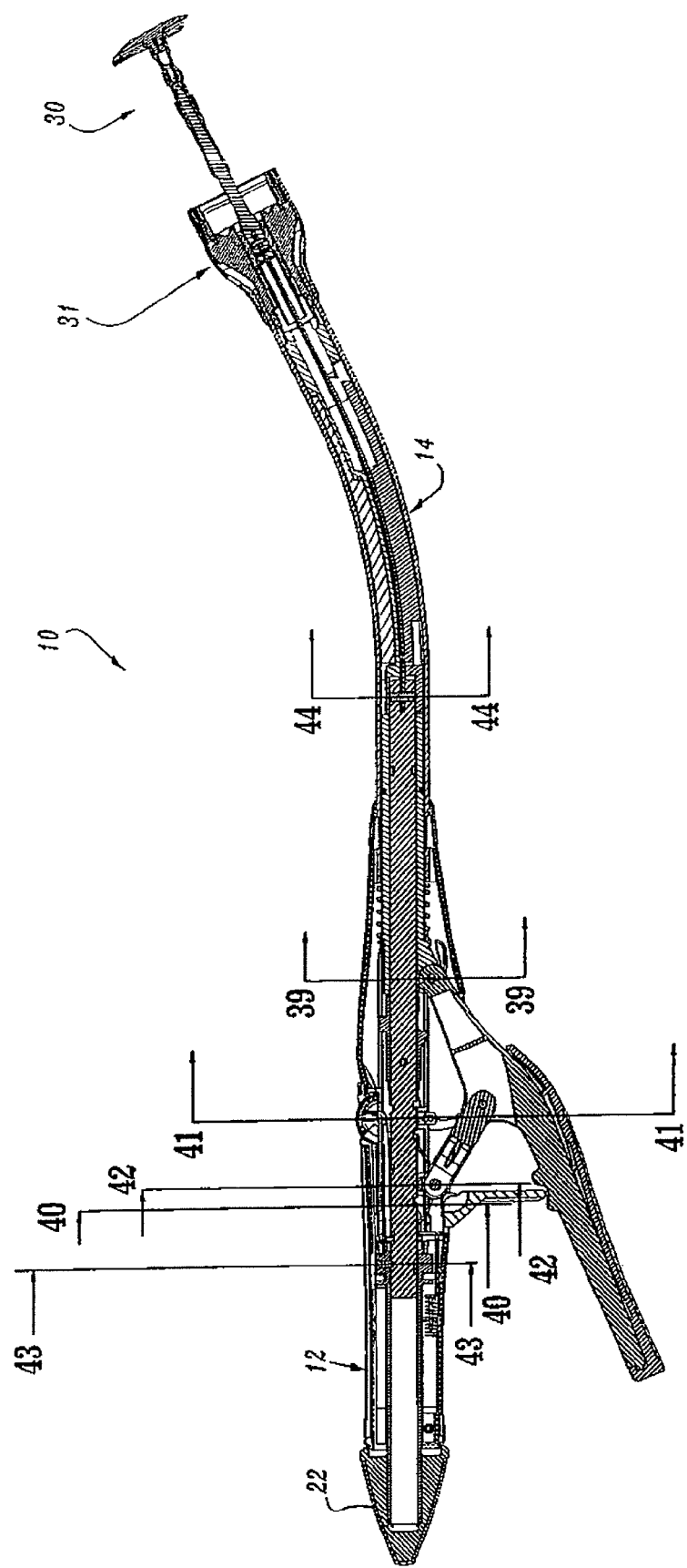
FIG. 38 is a side cross-sectional view of the surgical stapling device shown in FIG. 31 with the anvil assembly attached thereto.

FIGS. 36-44 illustrate surgical stapling device 10 with anvil assembly 30 attached to anvil retainer 38 and the anvil assembly 30 in the unapproximated or open position. Referring to FIGS. 37 and 38, during attachment of anvil assembly 30 to anvil retainer 38, anvil retainer 38 is positioned within bore 170 of center rod 154 of anvil assembly 30. Flexible arms 155 deflect outwardly to accommodate center rod 154. Center rod 154 is advanced onto anvil retainer 38 in the direction indicated by arrow "K" in FIG. 37 until internal shoulder 155b of flexible arms 155 passes over annular protrusion 177 formed on anvil retainer 38. At this point, resilient legs 155 releasably engage the anvil retainer. The position of the remaining components of stapling device are unaffected by attachment of anvil assembly 30 to anvil retainer 38 and remain as described above and shown in FIGS. 31-35.

FIGS. 45-50 illustrate surgical stapling device 10 during movement of anvil assembly 30 and cartridge assembly 31 to the approximated or closed position. As discussed above, anvil assembly 30 is moved to the approximated or closed position by rotating rotation knob 22 in the direction indicated by arrow "L" in FIG. 45. Rotation of knob 22 causes cylindrical sleeve 33 to rotate to move pin 52 along helical channel 50 of screw 32. Movement of pin 52 (FIG. 48) along helical channel 50 causes screw 32 to translate within sleeve 33. The distal end of screw 32 is connected to screw extensions 34 and 36 which are fastened at their distal ends to anvil retainer 38. As such, retraction of screw 32 within sleeve 33 is translated into proximal movement of anvil retainer 38 and anvil assembly 30. It is noted that when anvil assembly 30 is approximated, flexible legs 155 of center rod 154 are drawn into bushing 209 to lock legs 155 onto anvil retainer 38. (See FIG. 46).

As discussed above, screw stop 306 (FIG. 47) is axially fixed to screw 32 by set screw 312. Thus, as screw 32 is retracted within sleeve 33, screw stop 306 is moved from a distal position within stationary handle 18 to a proximal position. As screw stop 306 moves from the distal position to the proximal position, first engagement member 522 formed on screw stop 306 abuts proximal end 506a of slot 506 of slide plate 500 and moves slide plate 500 proximally against the bias of spring 512. As slide plate 500 moves proximally, lip 508 of slide member 500 engages projections 518 & 520 of indicator 24 to pivot indicator 24 in a counter-clockwise direction as viewed in FIG. 48.

Figure 47:
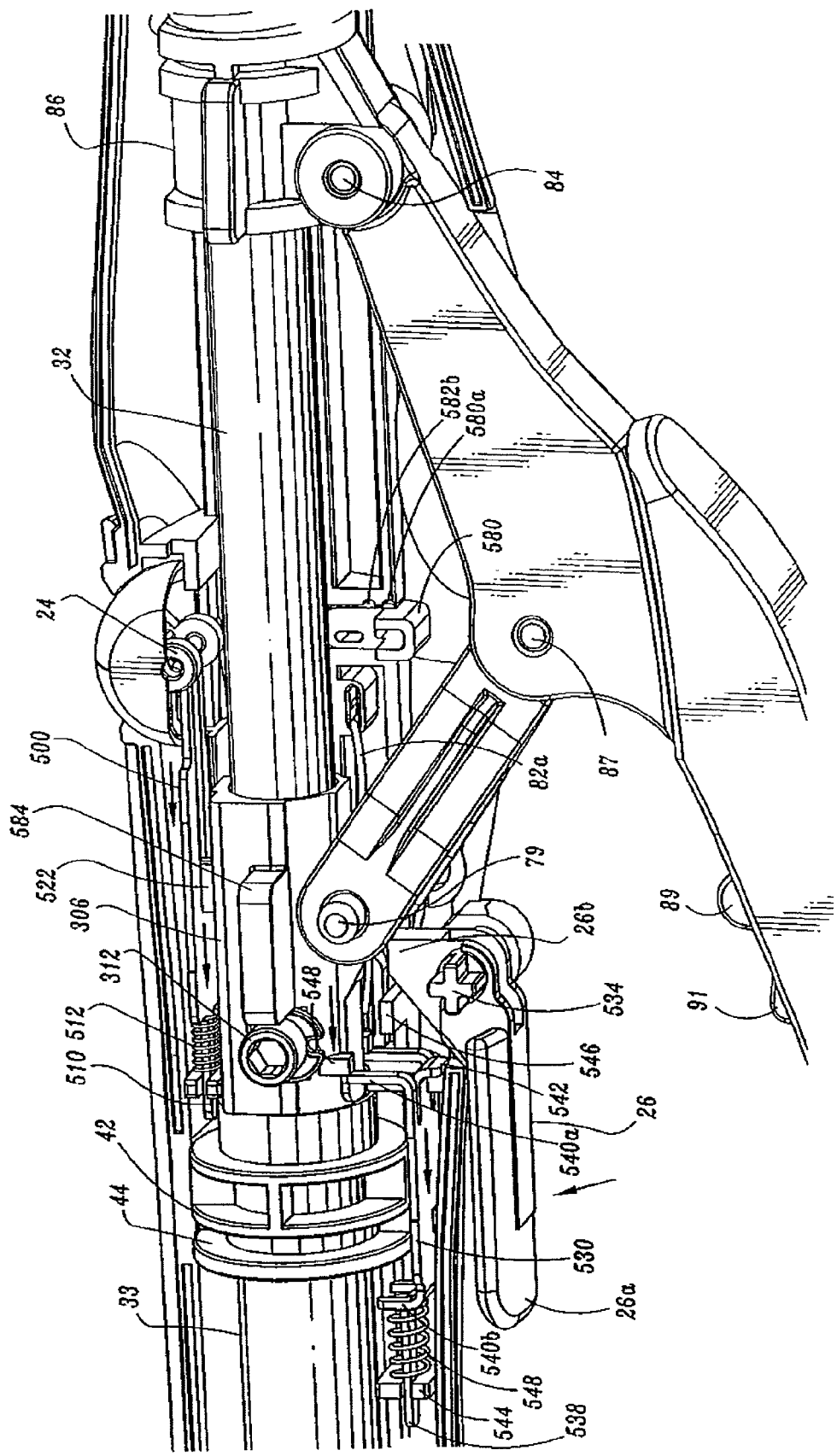
FIG. 47 is a side enlarged view of the handle assembly of the surgical stapling device shown in FIG. 45 with a handle section removed.
Figure 50:
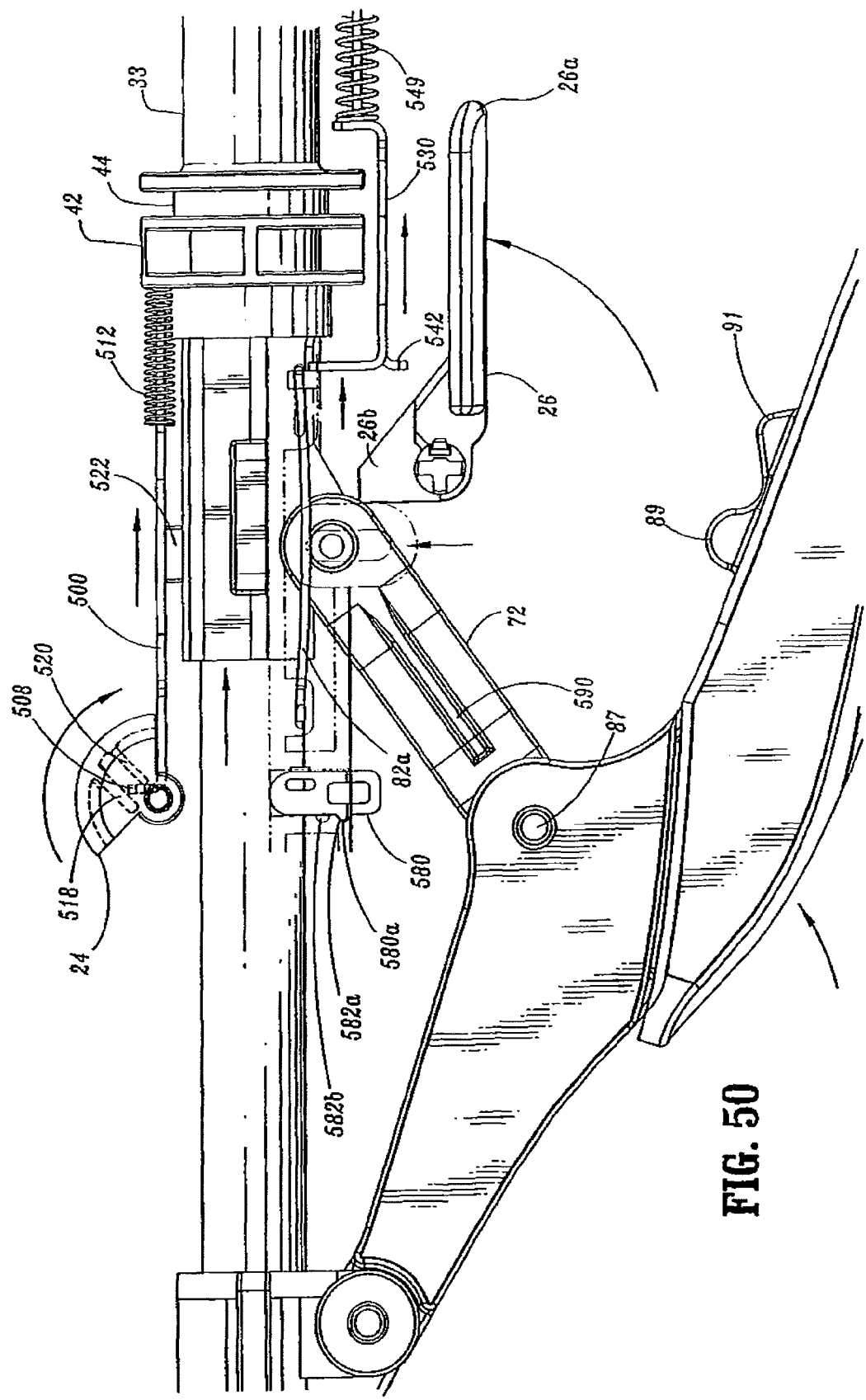
FIG. 50 is a side view of a portion of the handle assembly of the surgical stapler shown in FIG. 45 with the handle sections removed.

Screw stop 306 also includes a second engagement member 548 (FIG. 47). As screw stop 306 is moved from the distal position to the proximal position during approximation of anvil assembly 30, second engagement member 548 engages distal legs 540a of lockout member 530 to move lockout member 530 proximally to a position in which lip portion 542 is spaced proximally of extension 26b of trigger lock 26. In this position, trigger lock 26 can be pivoted to an unlocked position to permit firing of stapling device 10.

Movement of screw stop 306 to its proximal-most position within stationary handle 18 positions abutment surface 307 (FIG. 48) of screw stop 306 in position to engage pivot member 79 of firing link 72. Abutment surface 307 comprises a substantially concave surface which is positioned to partially capture and act as a backstop for pivot 79 during firing of the stapling device.

FIGS. 51-56 illustrate surgical stapling device 10 during the firing stroke of firing trigger 20. As trigger 20 is compressed towards stationary handle 18 (as shown by the arrow in FIG. 51), pivot member 79 engages abutment surface 307 on screw stop 306 and firing trigger 20 is pushed distally. As discussed above, the distal end of firing trigger 22 is connected through coupling member 86 to the proximal end of pusher link 74. Accordingly, as firing trigger 20 is moved distally, pusher link 74 is moved distally to effect advancement of pusher back 186 within shell assembly 31. Fingers 190 of pusher back 186 engage and eject staples 230 from staple guide 192 (FIG. 52).

Figure 55:
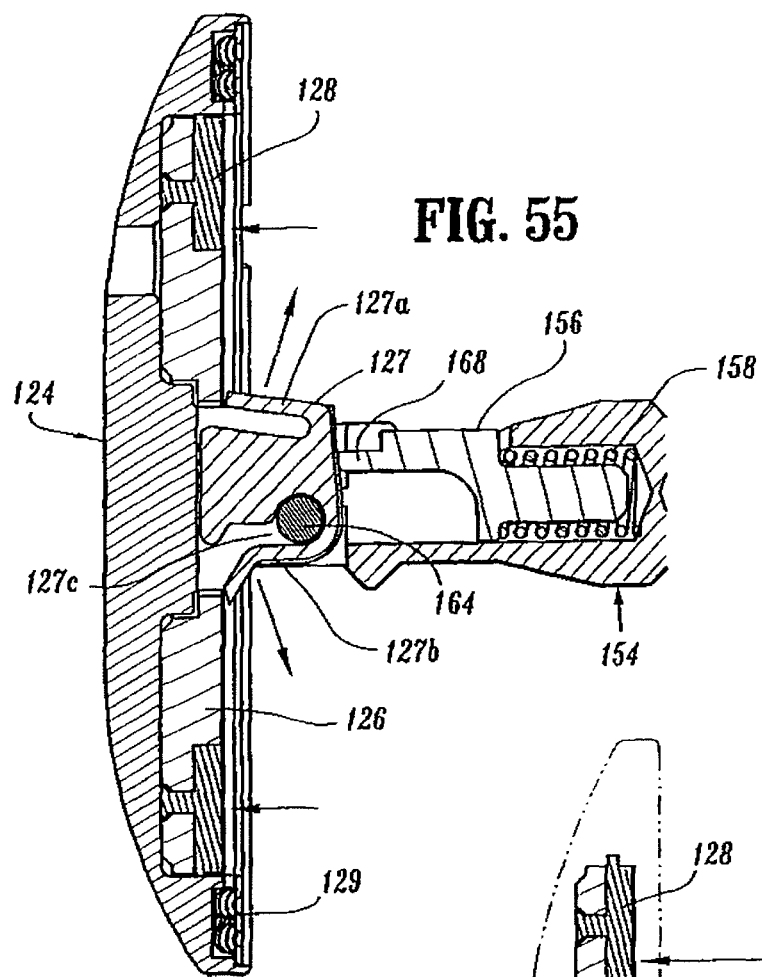
FIG. 55 is a side cross-sectional view of the distal portion of the anvil assembly of the surgical stapling device shown in FIG. 52.
Figure 56:
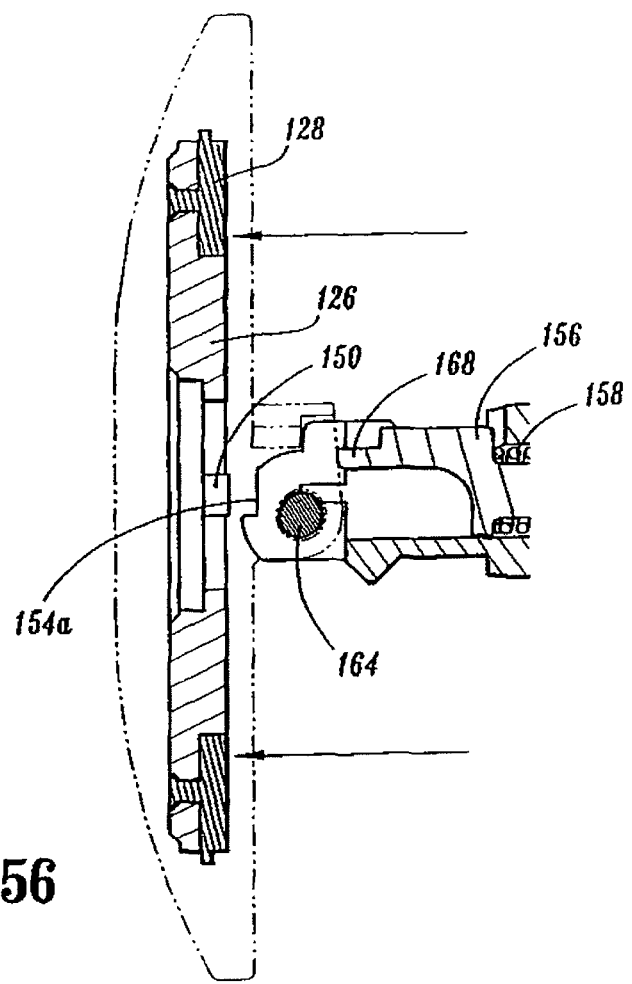
FIG. 56 is a side cross-sectional view of the distal portion of the anvil assembly shown in FIG. 55 with a portion of the anvil head assembly in phantom.

Cylindrical knife 188 is moved concurrently with pusher back 186 such that knife 188 moves into engagement with cutting ring 128 and backup plate 126. As discussed above, cutting ring 128 may be formed from polyethylene and backup plate 126 may be formed from a metal. When knife 188 engages cutting ring 128, it cuts into cutting ring 128 and pushes backup plate 126 deeper into anvil head 124 to move tabs 150 from engagement with top surface 154a of center rod 154 (FIG. 56). Anvil head 124 is now free to pivot about member 164 and is urged to do so by plunger 156. It is noted that because the anvil assembly is in juxtaposed alignment with shell assembly 31, the anvil head 14 will not pivot fully until the anvil and shell assemblies have been unapproximated a distance sufficient to allow the anvil head to fully pivot. When backup plate 126 moves into anvil head 124, flexible arms 127a and 127b of retainer clip 127 spring outwardly to a position in front of backup plate 126 blocking movement of backup plate 126 out of anvil head 124 (FIG. 55). As discussed above, arms 127a and 127b prevent backup plate 126 from sticking to knife 188 when anvil assembly 30 is returned to the unapproximated position.

Referring to FIGS. 57-60, during unapproximation of stapling device 10 after device 10 has been fired, wing 584 of screw stop 306 engages tactile indicator 580 (FIG. 58) at the point of unapproximation at which anvil assembly 124 is able to pivot to its tilted reduced profile position. Contact between wing 584 and tactile indicator 580 provides a tactile and/or audible indication that anvil head 124 has tilted. If additional force is provided to approximation knob 22, wing 584 of screw stop 306 will force tactile indicator to the retracted position to allow stapling device 10 to move to the fully open position. In this position, flexible arms 155 are positioned distally of bushing 209 and anvil assembly 30 can be disengaged from anvil retainer 28.

FIGS. 62-91 illustrate another embodiment of the presently disclosed surgical stapling device shown generally as 600. Stapling device 600 is configured and dimensioned to be particularly suitable for use in surgical procedures for removing internal hemorrhoids from a patient. Briefly, surgical stapling device 600 includes a proximal handle assembly 601, a central body portion 603 and a distal head portion 605. The handle assembly 601 is substantially identical to handle assembly 12 of surgical stapling device 10 and will not be discussed in further detail herein.

Figure 65:
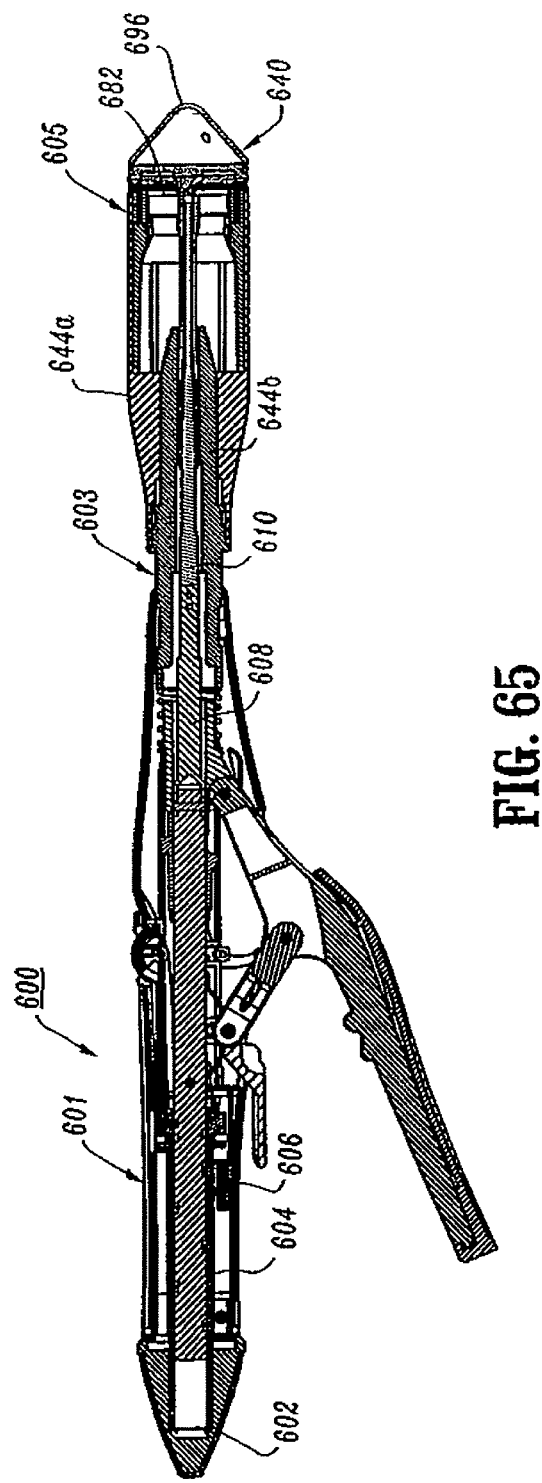
FIG. 65 is a side cross-sectional view of the surgical stapling device shown in FIG. 63 with the anvil assembly in the approximated position.
Figure 67:
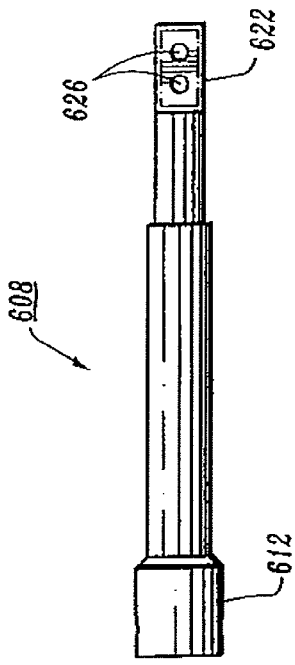
FIG. 67 is a side view of the retainer extension shown in FIG. 66.
Figure 66:
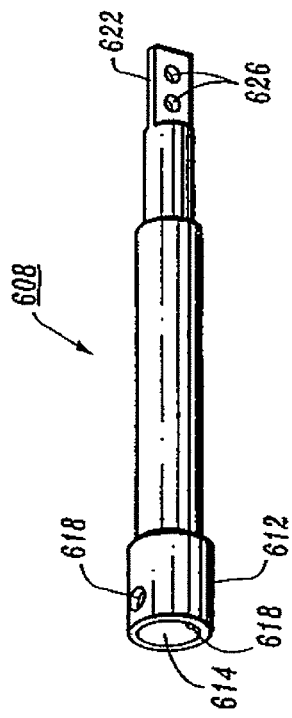
FIG. 66 is a side perspective view from the proximal end of the retainer extension of the surgical stapling device shown in FIG. 65.
Figure 68:
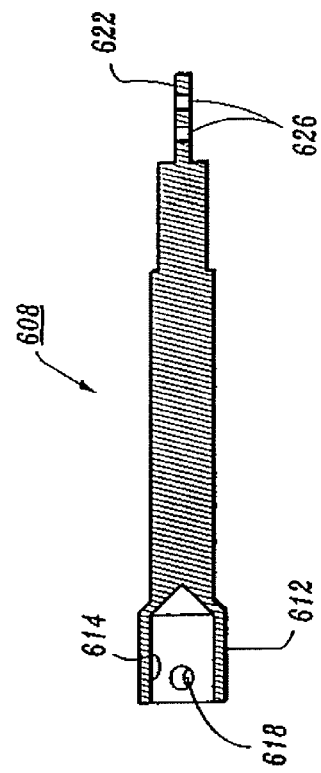
FIG. 68 is a top cross-sectional view of the retainer extension shown in FIG. 67.
Figure 72:
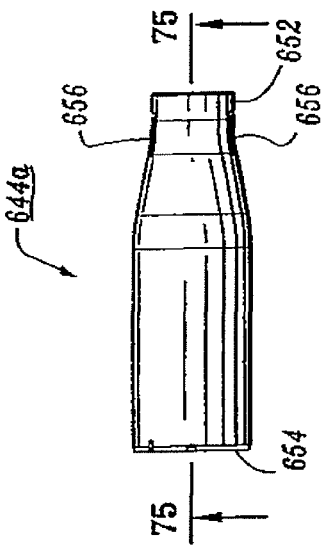
FIG. 72 is a side view of the outer housing portion of the shell assembly of the surgical stapling device shown in FIG. 65.
Figure 73:
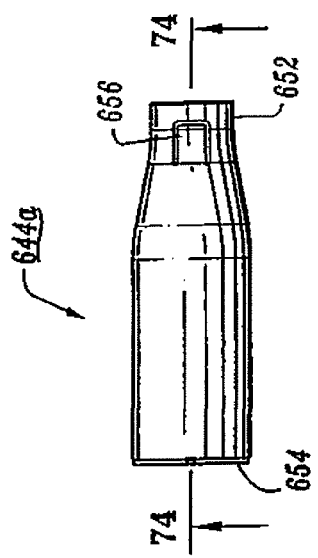
FIG. 73 is a top view of the outer housing portion of the shell assembly shown in FIG. 72.
Figure 74:
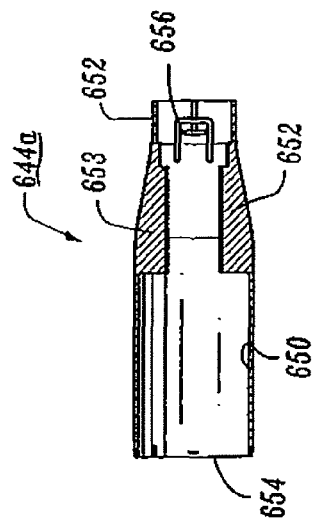
FIG. 74 is a cross-sectional view taken along section lines 74-74 of FIG. 72.
Figure 75:
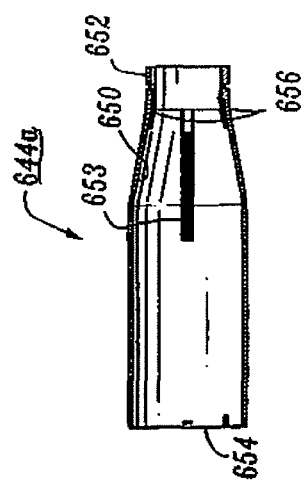
FIG. 75 is a cross-sectional view taken along section lines 75-75 of FIG. 73.
Figure 77:
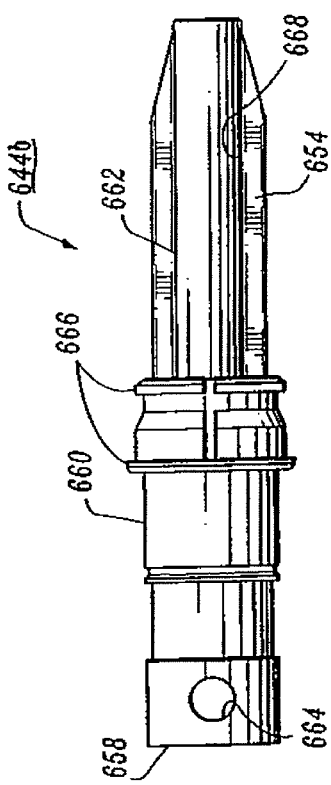
FIG. 77 is a top view of the inner guide portion of the shell assembly shown in FIG. 76.
Figure 79:
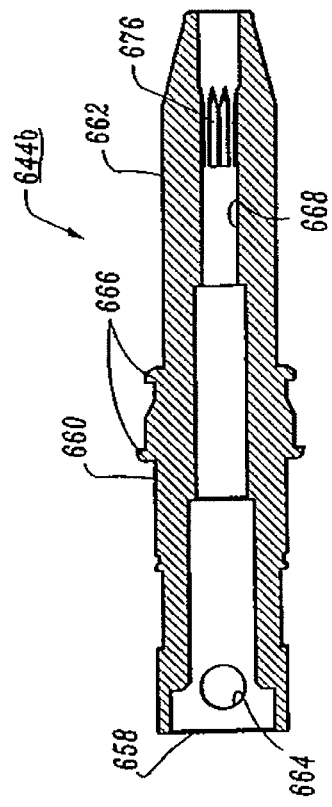
FIG. 79 is a top cross-sectional view of the inner guide portion of the shell assembly shown in FIG. 77.
Figure 76:
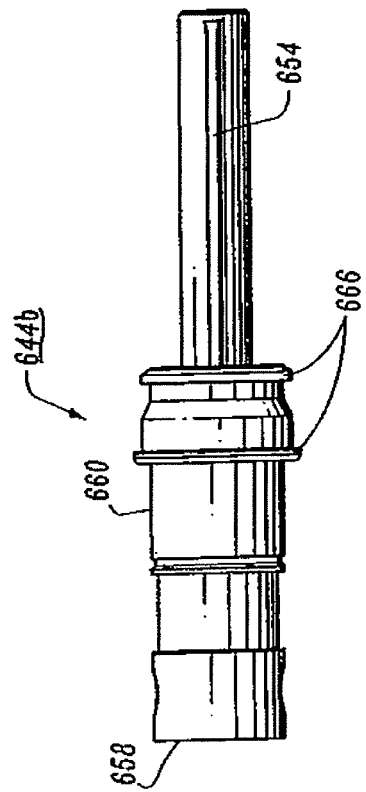
FIG. 76 is a side view of the inner guide portion of the shell assembly of the surgical stapling device shown in FIG. 65.

Referring to FIGS. 62-71, the approximation mechanism of surgical stapling device 600 includes an approximation knob 602, a rotatable sleeve 604, a drive screw 606, a retainer extension 608, and an anvil retainer 610. Approximation knob 602, rotatable sleeve 604 and drive screw 606 are substantially identical to the like named components described above with respect to surgical stapling device 10 and will not be described in further detail herein. Referring to FIGS. 66-68, retainer extension 608 includes a proximal end 612 defining a bore 614 dimensioned to receive the distal end of drive screw 606. A pair of transverse openings 618 extend through sidewalls of the proximal end of retainer extension 608 to facilitate attachment of retainer extension 608 to the distal end of drive screw 606 with a pin or screw 620 (FIG. 62). Alternately, other known attachment devices may be used, e.g., welding, brazing, screw threads, etc. The distal end of retainer extension 608 includes a flat finger 622 configured to be received within a slot 624 (FIG. 69) formed in the proximal end of anvil retainer 610. Openings 626 and 626a in retainer extension 608 and anvil retainer 610 (FIG. 70), respectively, are dimensioned to receive pins or screws 628 (FIG. 62) to secure anvil retainer 610 to the distal end of retainer extension 608. Alternately, other attachment configurations and techniques are contemplated.

Referring also to FIGS. 69-71, anvil retainer 610 includes an elongated reduced diameter distal extension 630 and a central annular shoulder 632. In one embodiment, annular shoulder 632 defines an angle of about ninety-degrees with respect to the outer axial surface 610a of anvil retainer 610 (FIG. 71). As will be discussed in further detail below, the sharp angle of shoulder 632 securely fastens an anvil assembly onto anvil retainer 610. As discussed above with respect to stapling device 10, when approximation knob 602 (FIG. 62) is manually rotated, rotatable sleeve 604 is rotated about the proximal end of screw 606 to advance or retract screw 606 within handle assembly 601. Since the proximal end 612 of retainer extension 608 is fastened to the distal end of screw 606 and the proximal end of anvil retainer 610 is fastened to the distal end of retainer extension 608, retainer extension 608 and anvil retainer 610 will move axially within central body portion 603 when drive screw 606 moves axially within handle assembly 601. As will be discussed in further detail below, an anvil assembly 640 (FIG. 64) is secured to anvil retainer 610. Accordingly, when approximation knob 602 is manually rotated, anvil assembly 640 will move axially with anvil retainer 610 in relation to a shell assembly 642 between spaced and approximated positions.

As illustrated in FIGS. 62-64, distal head portion 605 (FIG. 63) includes anvil assembly 640 and shell assembly 642. Shell assembly 642 includes a housing 644, a pusher 646, a cylindrical knife 645 and a staple guide 648. Referring also to FIGS. 72-79, housing 644 includes an outer housing portion 644a and an inner guide portion 644b. Outer housing portion 644a (FIGS. 72-75) defines an outwardly diverging throughbore 650 and includes a small diameter proximal end 652 and a large diameter distal end 654. Distal end 652 includes a pair of diametrically opposed spring tabs 656 for releasably engaging inner guide portion 644b in a manner to be discussed below. Throughbore 650 is dimensioned to slidably receive pusher 646 (FIG. 62). Because of the configuration of throughbore 650 and pusher 646, pusher 646 is slidable in throughbore 650 only in a distal direction. A pair of stabilizing ribs 653 (FIG. 75) extend inwardly from an inner wall defining throughbore 650. Stabilizing ribs 653 engage ribs 654 (FIG. 76) formed on sidewalls of inner guide portion 644b to secure inner guide portion 644b within outer housing portion 644a.

Figure 78:
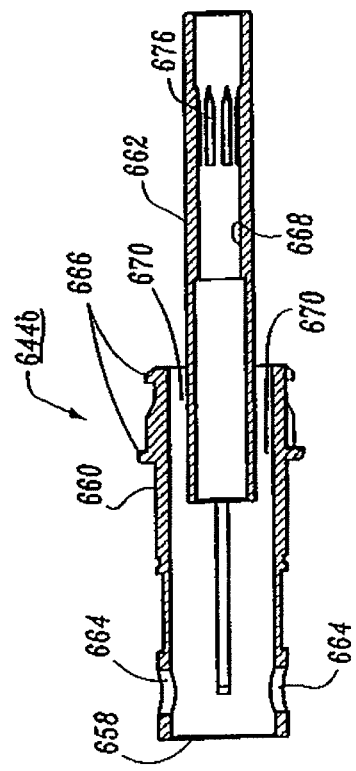
FIG. 78 is a side cross-sectional view of the inner guide portion of the shell assembly shown in FIG. 77.
Figure 81:
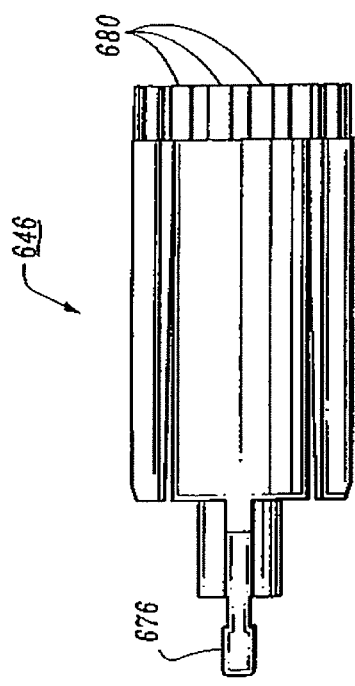
FIG. 81 is a top view of the pusher shown in FIG. 80.
Figure 80:
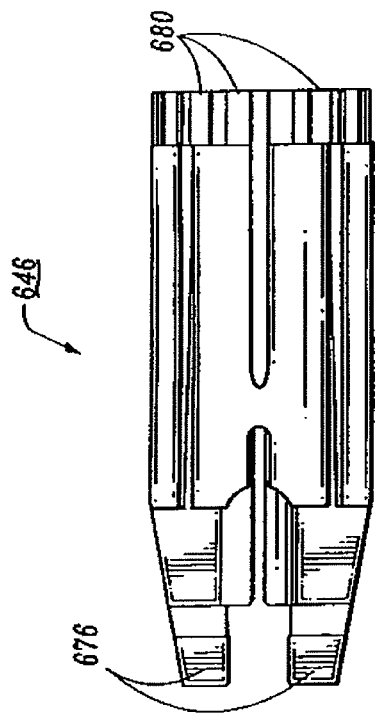
FIG. 80 is a side view of the pusher of the surgical stapling device shown in FIG. 65.
Figure 83:
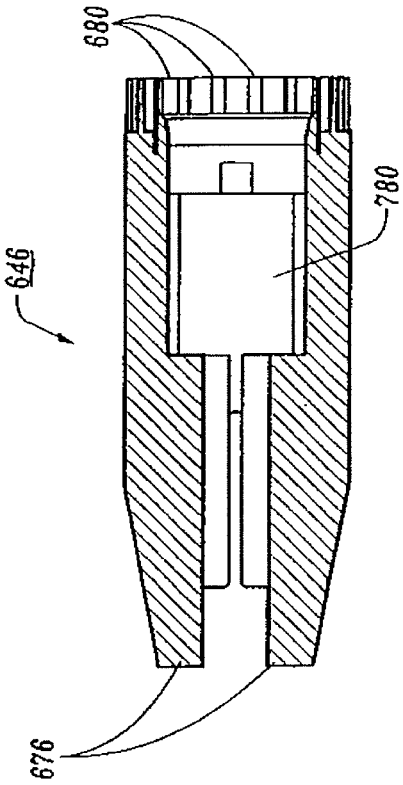
FIG. 83 is a top cross-sectional view of the pusher shown in FIG. 82.
Figure 82:
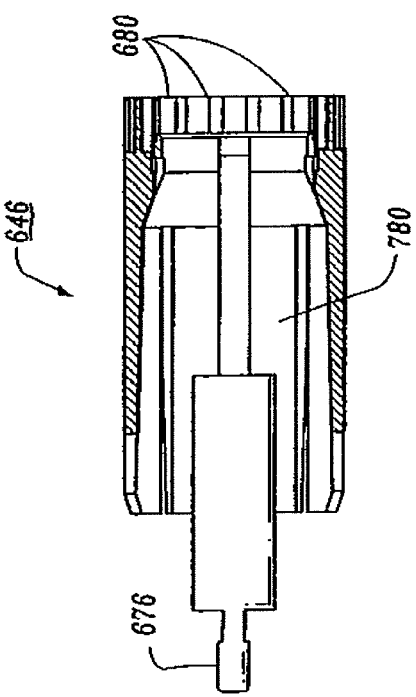
FIG. 82 is a side cross-sectional view of the pusher shown in FIG. 81.
Figure 88:
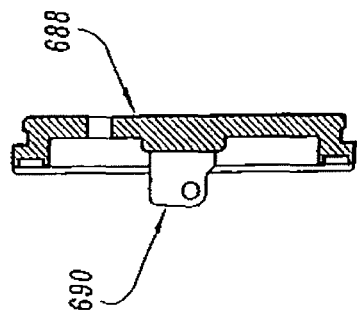
FIG. 88 is a side cross-sectional view of the anvil head of the anvil assembly shown in FIG. 85.
Figure 89:
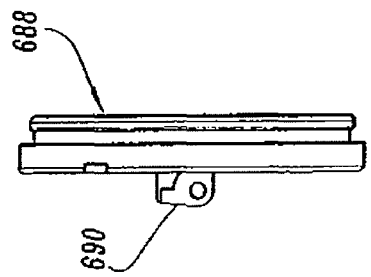
FIG. 89 is a side view of the anvil head shown in FIG. 88.
Figure 84:
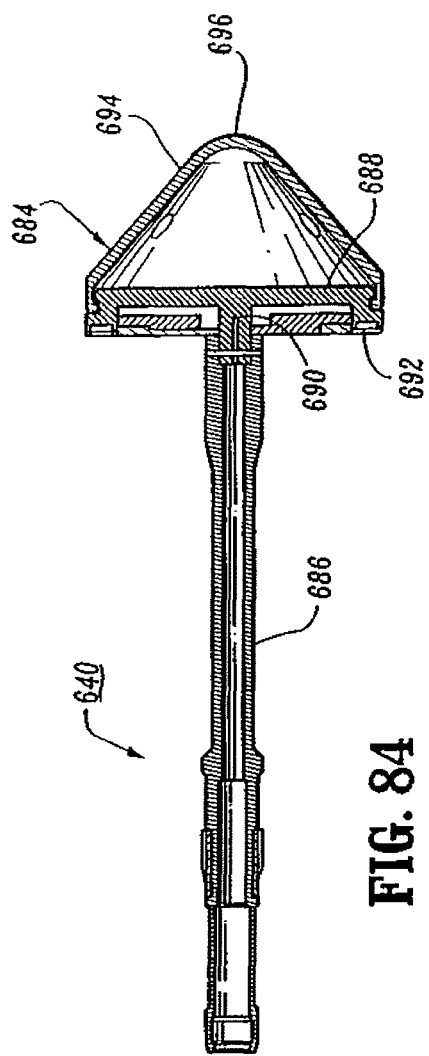
FIG. 84 is a side cross-sectional view of the anvil assembly of the surgical stapling device shown in FIG. 65.
Figure 85:
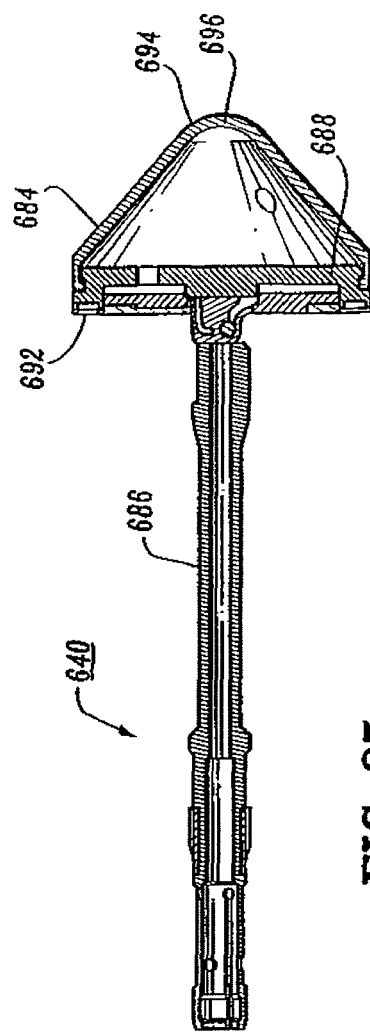
FIG. 85 is a top cross-sectional view of the anvil assembly of the surgical stapling device shown in FIG. 84.

Inner guide portion 644b (FIGS. 76-79) includes a cylindrical proximal end 658, a cylindrical central portion 660 and an inner distal portion 662. Proximal end 658 includes a pair of openings 664 for engaging spring tabs (not shown) formed on handle assembly 612 for securing shell assembly 642 onto handle assembly 612. Ribs 654 are formed on inner distal portion 662 of inner guide portion 644b. A pair of annular ribs 666 are formed in spaced relation on central portion 660. Spring tabs 656 of outer housing portion 644a (FIGS. 72-75) are positioned to snap fit into the space between ribs 666 to secure inner guide portion 644b to outer housing portion 644a. Inner distal portion 662 defines a cylindrical bore 668 for slidably receiving retainer extension 608 and anvil retainer 610 (FIG. 62). Cylindrical bore 668 includes an annular array of ribs and grooves 676 for accurately circumferentially and axially aligning anvil assembly 640 and shell assembly 642 during approximation thereof. The proximal end of distal portion 662 extends proximally within central portion 660 to define therewith a pair of channels 670 (FIG. 78). A proximal portion of channels 670 is dimensioned to slidably receive drive arms of a pusher link (not shown). The pusher link employed in this embodiment is similar to pusher link 74 discussed above with respect to stapling device 10 and will not be discussed in further detail herein.

Referring to FIGS. 62 and 80-83, pusher 646 is slidably positioned within shell assembly housing 644. Pusher 646 includes a pair of proximal extensions 676 which extends through the distal end of channels 670 (FIG. 78) formed in inner guide portion 644b. The distal end of pusher 646 includes a multiplicity of distally extending fingers 680 which are slidably received within slots formed in staple guide 648 (FIG. 62). Staple guide 648 is fixedly retained in the distal end of outer housing portion 644a. Staples (not shown) are housed within the staple guide slots (not shown). Movement of pusher 646 distally within outer housing portion 644a ejects staples from the slots of staple guide 648. A cylindrical knife 645 (FIGS. 62 and 63) is secured or frictionally retained within a central throughbore of pusher 646. The distal end of knife 645 includes an annular cutting edge 682. The distal portion of pusher 646 defines an internal chamber 780 for receiving excised tissue.

Figure 92:
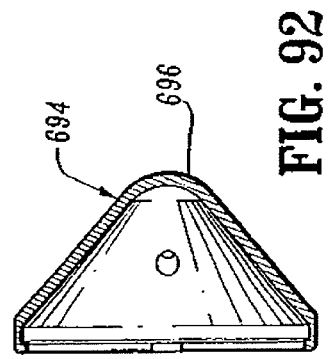
FIG. 92 is a side cross-sectional view of the anvil cover shown in FIG. 91.
Figure 91:
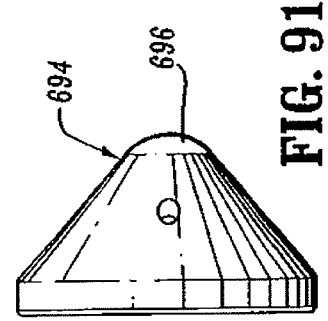
FIG. 91 is a side view of the anvil cover of the anvil assembly shown in FIG. 84.

Referring to FIGS. 84-89, anvil assembly 640 includes an anvil head assembly 684 and an anvil center rod 686. Anvil head assembly 684 includes an anvil head 688, an anvil post 690, an anvil 692 and an anvil cover 694. Anvil cover 694 (FIGS. 91 and 92) is substantially conical and includes a rounded distal portion 696 to facilitate smooth entry of anvil assembly 640 into a body lumen or orifice, e.g., anus. Anvil 692 is secured to anvil head 688 and includes a plurality of staple deforming pockets (not shown), as discussed above, for receiving and deforming staples. Anvil head assembly 684 is secured to the distal end of anvil center rod 686. Although anvil head assembly 684 may be pivotally secured to anvil center rod 686, as discussed above, in one embodiment, anvil head assembly 684 is fixedly secured to anvil center rod 686.

Figure 86:
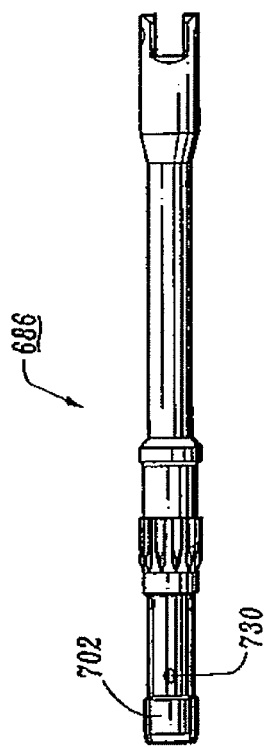
FIG. 86 is a top view of the anvil center rod of the anvil assembly shown in FIG. 85.
Figure 87:
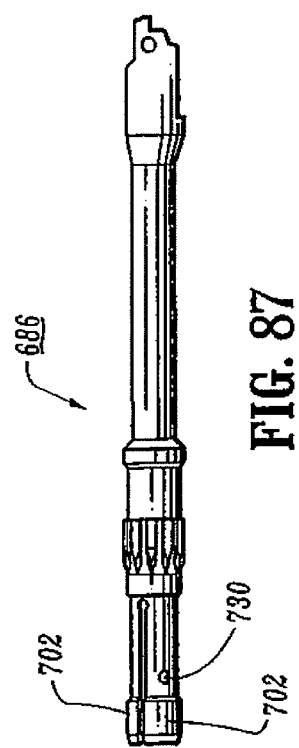
FIG. 87 is a side view of the anvil center rod of the anvil assembly shown in FIG. 85.
Figure 90:
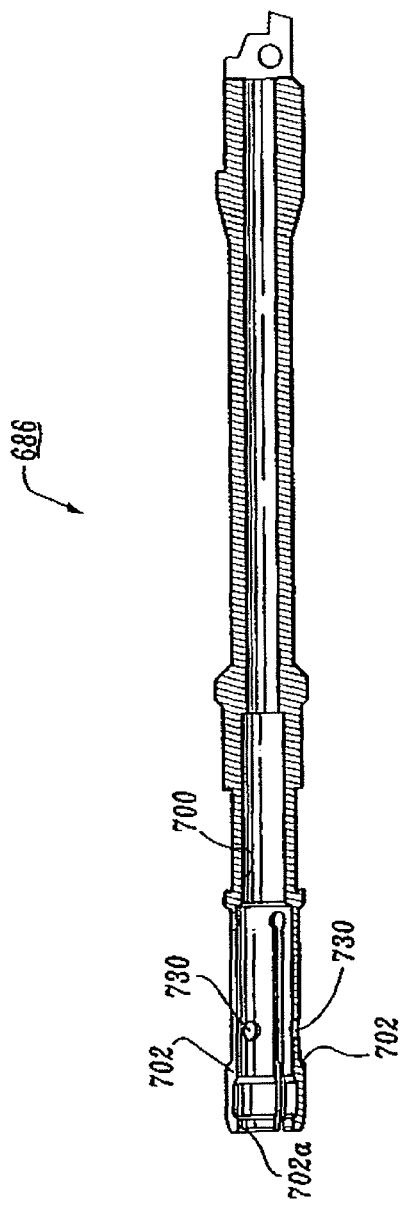
FIG. 90 is a side cross-sectional view of the anvil center rod shown in FIG. 87.
Figure 97:
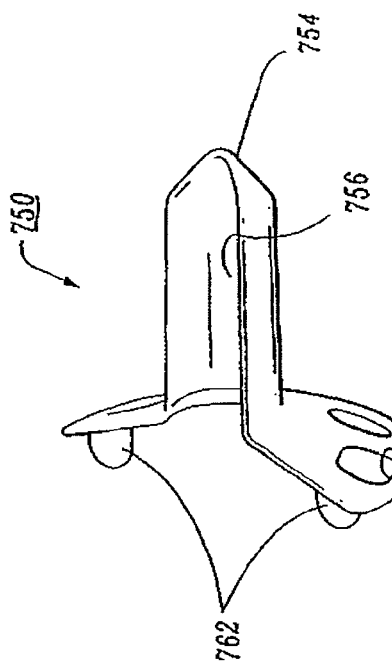
FIG. 97 is a side perspective view from above of the speculum shown in FIG. 96.
Figure 99:
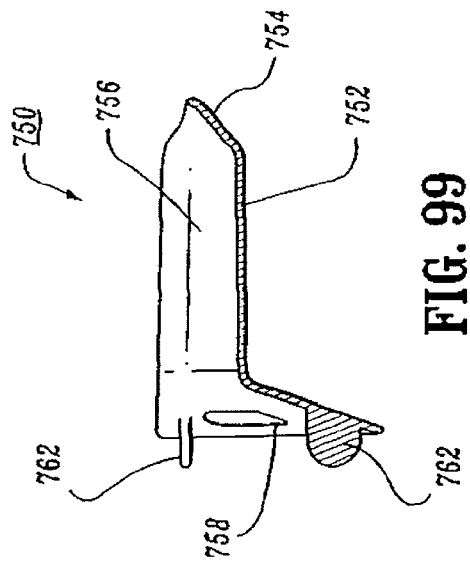
FIG. 99 is a side cross-sectional view of the speculum shown in FIG. 97.
Figure 96:
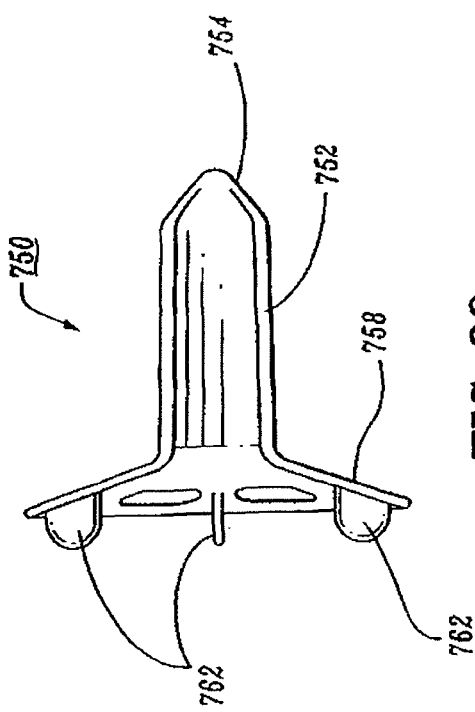
FIG. 96 is a top view of a speculum suitable for use with the presently disclosed surgical stapling device.
Figure 98:
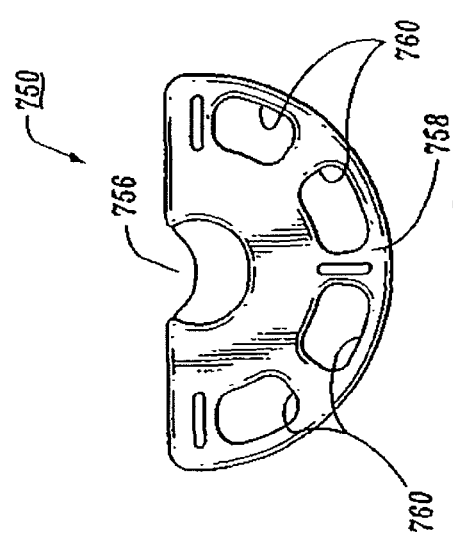
FIG. 98 is a rear view of the speculum shown in FIG. 96.

As illustrated in FIGS. 86 and 87 and 90, anvil center rod 686 defines a central bore 700 which is partially defined by a plurality of flexile arms 702. Central bore 700 extends substantially along the longitudinal length of center rod 686. The distal end of each flexible arm 702 includes a radial projection 702a. Central bore 700 is dimensioned to slidably receive anvil retainer 610 (FIG. 62) including distal extension 630 such that radial projections 702a snap over and engage annular shoulder 632 (FIGS. 70 and 71) of anvil retainer 610 to secure anvil assembly 640 to anvil retainer 610. Radial projection 702a (FIG. 90) defines a perpendicular surface which abuts shoulder 632 to securely fasten anvil assembly 640 to anvil retainer 610 and substantially prevent inadvertent disengagement of anvil assembly 640 from anvil retainer 610. When anvil assembly 640 is secured to anvil retainer 610, distal extension 630 of anvil retainer 610 extends through central bore 700 along a substantial portion of the length of anvil center rod 686. In one embodiment, distal extension 630 extends through central bore 700 substantially the entire length of anvil center rod 686.

In use, when approximation knob 602 (FIG. 63) is manually rotated to move screw 606 proximally, anvil retainer 610 and anvil assembly 640 are withdrawn into shell assembly 642 to move anvil head assembly 684 into approximation with shell assembly 642 (FIG. 65). When flexible arms 702 are drawn into cylindrical bore 668 of inner guide portion 644b, arms 702 are prevented from flexing outwardly to lock anvil assembly 640 to anvil retainer 610.

As discussed above, stapling device 600 is particularly suitable for use in surgical procedures for removing internal hemorrhoids from a patient. During such a procedure, anvil assembly 640 (FIG. 64) is inserted into the anus and rectum of the patient independently of stapling device 600. Referring to FIGS. 93-95, an insertion handle 720 may be used to facilitate insertion of anvil assembly 640 into the anus and rectum. In one embodiment, handle 720 includes a gripping knob 722, a rigid shaft 725 extending distally from knob 722 and an attachment portion 724. Attachment portion 724 includes a detent 726 and a protrusion 728. Attachment portion 725 of shaft 724 is dimensioned to be slidably received within anvil center rod central bore 700. Detent 726 is positioned to be received within one of a plurality of suture holes 730 (FIG. 87) formed in the distal end of anvil center rod 686 to releaseably lock handle 720 to anvil center rod 686. Protrusion 728 is positioned to be slidably received between and engaged by flexible arms 702 to properly align handle 720 with anvil center rod 686. A stop member 728a may also be provided on the attachment portion to limit the insertion depth of shaft 724 into central bore 700. To remove handle 720 from anvil center rod 686, a force sufficient to flex flexible arms 702 outwardly must be applied to handle 720 to release detent 726 from suture hole 730. In one embodiment, after anvil assembly 640 has been properly positioned in the anus and rectum, a purse string suture is placed into each of the internal hemorrhoids. Thereafter, the purse string is cinched about the anvil center rod 686 to draw the internal hemorrhoids inwardly about the anvil center rod 686.

Referring to FIGS. 96-99, in an alternate embodiment, the purse string suture may be placed into the internal hemorrhoids prior to insertion of the anvil assembly into the anus and rectum. Using either embodiment, an anoscope or speculum 750, may be provided to place the purse string into the internal hemorrhoids. Speculum 750 may include a semi-cylindrical body 752 having a tapered or blunt tip 754. Body 752 defines a channel or recess 756. The proximal end of body 752 has a semi-annular flange 758 including a plurality of openings 760 and a pair of protruding finger tabs 762. Fingers tabs 762 and openings 760 allow for easier gripping and manipulation of the speculum during use. It is also envisioned that speculum 750 may be formed from a clear plastic material to enhance visualization. Further, the speculum 750 may include gradation markings (not shown) along the surface of the speculum 750 to assist the surgeon with knowledge of depth of placement of the hemorrhoids.

In use, blunt tip 754 of speculum 750 is inserted into the anus to a position in which first internal hemorrhoids hang into channel 756. A purse string suture is placed into a first portion of internal hemorrhoids. Speculum 750 is then rotated using finger tabs 762 and openings 760 until a second portion of internal hemorrhoids hang into channel 756. A purse string suture is placed into the second internal hemorrhoids. This process is repeated until a purse string suture has been placed into each of the internal hemorrhoids about the annulus of the anus.

When a purse string suture has been placed into each of the internal hemorrhoids, speculum 750 is removed from the anus and the anvil assembly 640 is inserted into the anus and rectum. Thereafter, the purse string sutures are cinched to draw the internal hemorrhoids in about the anvil center rod 686. Attachment structure such as openings, grooves, hooks, ridges or ribs, may be provided on anvil center rod 686 to secure the purse string suture and, thus, the internal hemorrhoids to the anvil center rod 686. It is also envisioned that the attachment structure may be in the form of an axially adjustable member, e.g., slidable hook, which may be adjusted to change the position of the purse string suture on anvil center rod 686 and within shell assembly 642. Likewise, gradations can be placed on the center rod 686 to indicate depth of insertion of the center rod 686 or length of the suture or of sutured hemorrhoids.

After the internal hemorrhoids have been cinched about anvil center rod 686, center rod 686 is attached to anvil retainer 610 in the manner discussed above. Distal extension 630 and anvil center rod 686 should be of a length to allow telescoping of extension 630 within anvil center rod 686 before visibility of the surgical site is obstructed by shell assembly 642 of device 600. In one embodiment, the combined length of anvil center rod 686 and retainer extension 630 is at least 4.5 inches (114.3) or of a length to achieve the above objective. By providing an extension on anvil retainer 610 and/or providing an elongated anvil center rod 686, visibility at the surgical site is greatly improved. Improved visibility not only simplifies attachment of anvil assembly 640 to anvil center rod 686 but improves visibility during approximation of anvil to ensure that the hemorrhoidal tissue is properly positioned about the anvil shaft.

After the anvil assembly has been attached to the anvil center rod 686, knob 602 can be manually rotated to approximate the anvil and shell assemblies and draw the internal hemorrhoids into an inner chamber 780 (FIG. 62) defined within pusher 646 and within annular knife 682 of shell assembly 642. Firing trigger 790 (FIG. 62) can now be actuated in the manner discussed above with respect to stapling device 10 to staple, sever and allow removal of the internal hemorrhoids. Thereafter, stapling device 600 is removed from the anus with the excised internal hemorrhoids contained within inner chamber 780 of shell assembly 642.

FIGS. 100-108 illustrate another embodiment of the presently disclosed surgical stapling device shown generally as 1000. Surgical stapling device 1000 includes a housing 1010, an elongated portion 1020, an end effector 1030, a movable handle 1040 and a ratchet mechanism 1050. Housing 1010 is substantially identical to handle assembly 12 of surgical stapling device 10 and handle assembly 601 of surgical stapling device 600 and will not be discussed in further detail herein.

Figure 100:
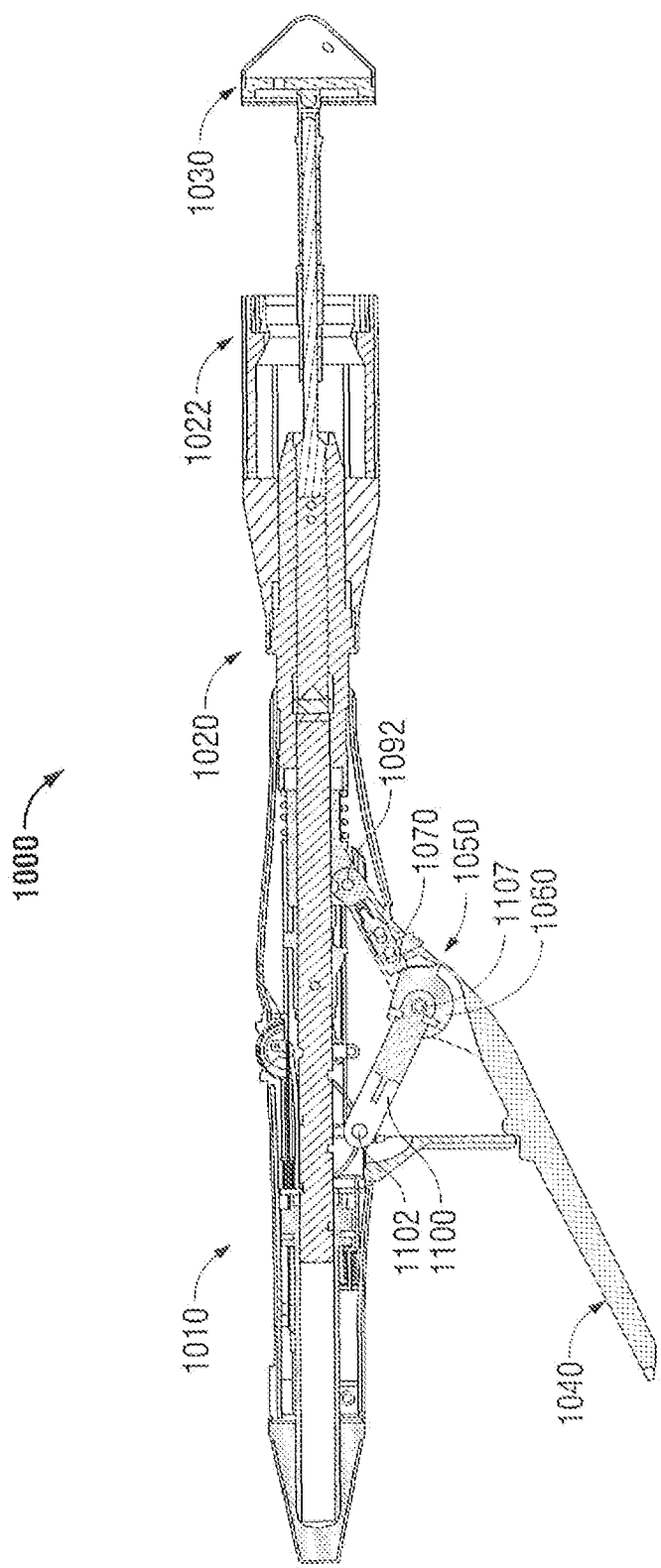
FIG. 100 is a longitudinal cross-sectional view of a surgical stapling device including a ratchet mechanism disposed in a first open position in accordance with another embodiment of the present disclosure.
Figure 101:
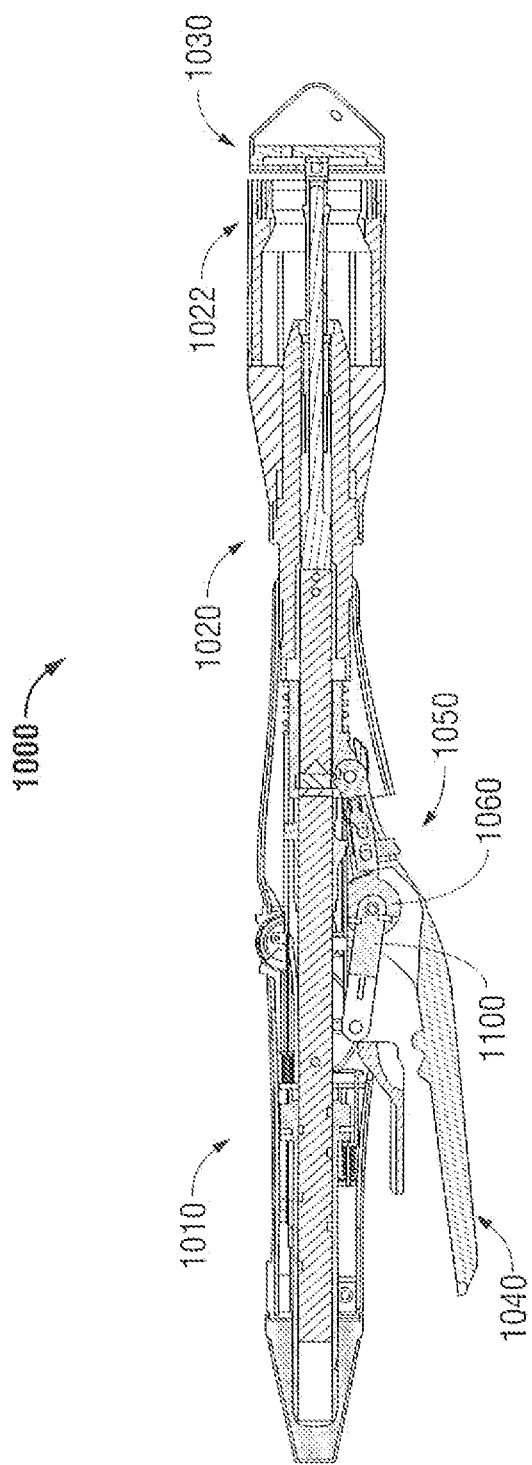
FIG. 101 is a longitudinal cross-sectional view of the surgical stapling device of FIG. 100 disposed in a second approximated position.

With reference to FIGS. 100 and 101, elongated portion 1020 extends distally from housing 1010 and at least a portion of end effector 1030 is disposed in mechanical cooperation with a distal portion 1022 of elongated portion 1020. End effector 1030 in the illustrated embodiment includes an anvil assembly and a shell assembly, the anvil assembly being moved into approximation with the shell assembly of distal portion 1022 by the approximation mechanisms described above. Movable handle 1040 is disposed in mechanical cooperation with housing 1010 and is movable between a first open position (FIGS. 100 and 103) and a second approximated position (FIGS. 101 and 105) for affecting a function of end effector 1030. Ratchet mechanism 1050 is disposed in mechanical cooperation with movable handle 1040 and is configured to substantially prevent movable handle 1040 from moving towards its first open position (in the general direction of arrow "M" in FIG. 105) until movable handle 1040 reaches a predetermined position. This predetermined position in a preferred embodiment corresponds to full firing of the stapler, e.g. firing of all the staples and full distal translation of the knife, if provided, although other predetermined positions are also contemplated, such as the commencement of firing of at least one staple. Thus, ratchet mechanism 1050 helps prevent movable handle 1040 from being prematurely opened, e.g., before staples have been fired and/or before a knife severs tissue. Accordingly, ratchet mechanism 1050 ensures a fuller firing stroke is performed before movable handle 1040 can be opened.

Details of ratchet mechanism 1050 are further illustrated in FIGS. 102-108. Ratchet mechanism 1050 includes a rack 1060, a pawl 1070 and a spring 1080. Rack 1060 is disposed in mechanical cooperation with housing 1010 and includes rack teeth 1062 and a cam surface 1064. Pawl 1070 is disposed in mechanical cooperation with movable handle 1040 and includes pawl teeth 1072. Rack teeth 1062 and pawl teeth 1072 are configured for engagement with one another. Spring 1080, e.g., a compression spring, is disposed in mechanical cooperation with movable handle 1040 and is configured to bias at least one of rack 1060 and pawl 1070 towards the other such that rack teeth 1062 and pawl teeth 1072 engage one another. In the illustrated embodiments, spring 1080 biases pawl 1070 in the direction of arrow "N" (FIG. 103) towards rack 1060. Cam surface 1064 of rack 1060 is configured to disengage rack teeth 1062 and pawl teeth 1072 upon contact between cam surface 1064 and pawl 1070 by urging pawl 1070 away from rack 1060 to facilitate movement of movable handle 1040 back towards its first open position.

With reference to FIGS. 102-105, a trigger insert 1090 is shown. Trigger insert 1090 may be integrally formed with movable handle 1040, attached to movable handle 1040 or may be insertable therewith. Trigger insert 1090 is pivotably coupled to housing 1010, e.g., via a pin 1092 (FIGS. 102-103) disposed through an opening 1094 on trigger insert 1090 and through an opening (not explicitly shown) of housing 1010, for instance.

A link 1100 is disposed in mechanical cooperation with housing 1010 and trigger insert 1090. Link 1100 is illustrated pivotably coupled to housing 1010, e.g., via a pin 1102 disposed through an opening 1104 on a first portion 1105 of link 1100 and through an opening (not explicitly shown) of housing 1010. Additionally, link 1100 is pivotably coupled to trigger insert 1090, e.g., via a pin 1107 disposed through an opening 1108 on a second portion 1109 of link 1100 and through an opening 1095 (FIG. 107) of trigger insert 1090.

Rack 1060, illustrated in FIGS. 103-106, is disposed adjacent second portion 1109 of link 1100. Additionally, rack 1060 is configured to engage second portion 1109 of link 1100 and may be secured to link 1100 via pins 1066a, 1066b extending through bores of rack 1060 and/or link 1100. Accordingly, rack 1060 is pivotably movable with respect to trigger insert 1090 (and movable handle 1040). As such, movement of movable handle 1040 from its first open position (FIGS. 100 and 103) in the direction of arrow "P" (FIG. 103) towards its second approximated position (FIGS. 101 and 105) causes rack 1060 to move in the general direction of arrow "Q" (FIG. 103) with respect to pawl 1070.

Pawl 1070 is illustrated in FIGS. 103-105 and 108 and is translatable with respect to trigger insert 1090 via slots 1074 in pawl 1070 and bosses 1096 in trigger insert 1090. Moreover, as can be appreciated, the width of slots 1074 dictate the boundaries of movement between pawl 1070 and trigger insert 1090. In the illustrated embodiments, pawl 1070 includes a spring hub 1076 for facilitating alignment with a proximal portion 1082 of spring 1080. A distal portion 1084 of spring 1080 is bound by a distal portion 1098 of trigger insert 1090. Thus, spring 1080 biases pawl 1070 proximally towards rack 1060, such that pawl teeth 1072 engage rack teeth 1062.

Figure 104:
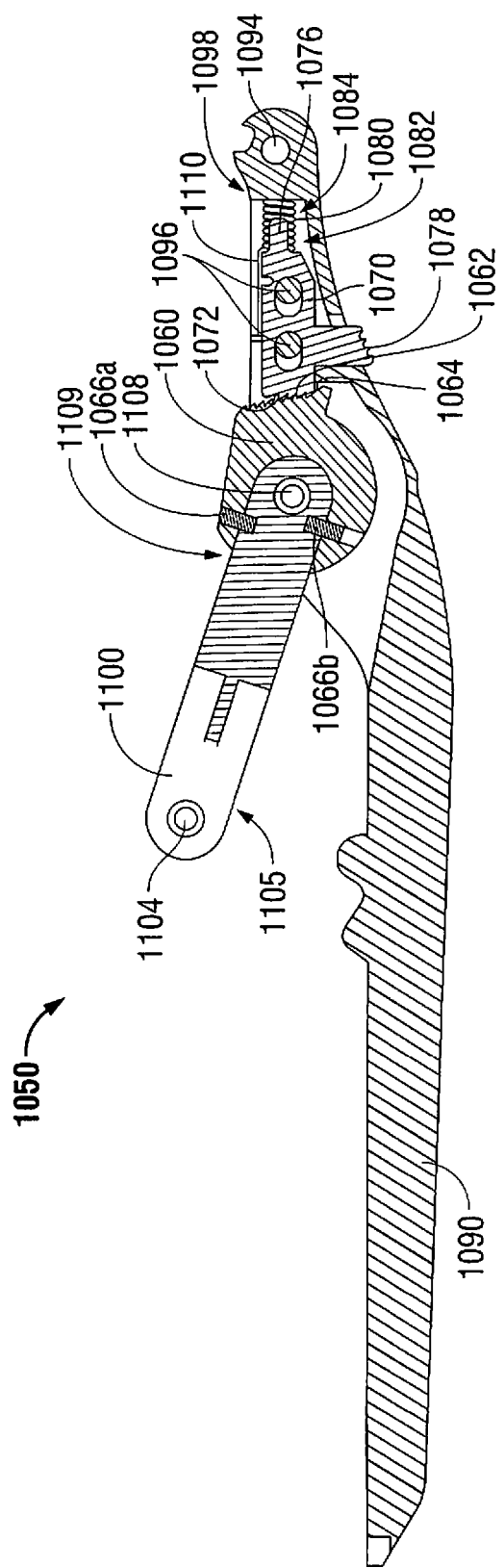
FIG. 104 is a longitudinal cross-sectional view of the ratchet mechanism of FIGS. 100-102 illustrated between its first open position and its second approximated position.

In operation, when movable handle 1040 is in its first open position (FIGS. 100 and 103), rack teeth 1062 are engaged with pawl teeth 1072. As movable handle 1040 is moved through the firing stroke in the direction of arrow "P" towards its second approximated position (FIG. 104 illustrates movable handle 1040 between its first open position and its second approximated position), rack teeth 1062 continue to engage pawl teeth 1072. As can be appreciated with reference to FIG. 104, when movable handle 1040 is between its first open position and its second approximated position, the engagement of rack teeth 1062 and pawl teeth 1072 substantially prevent movable handle 1040 from moving in the direction of arrow "M" towards its first open position.

Figure 105:
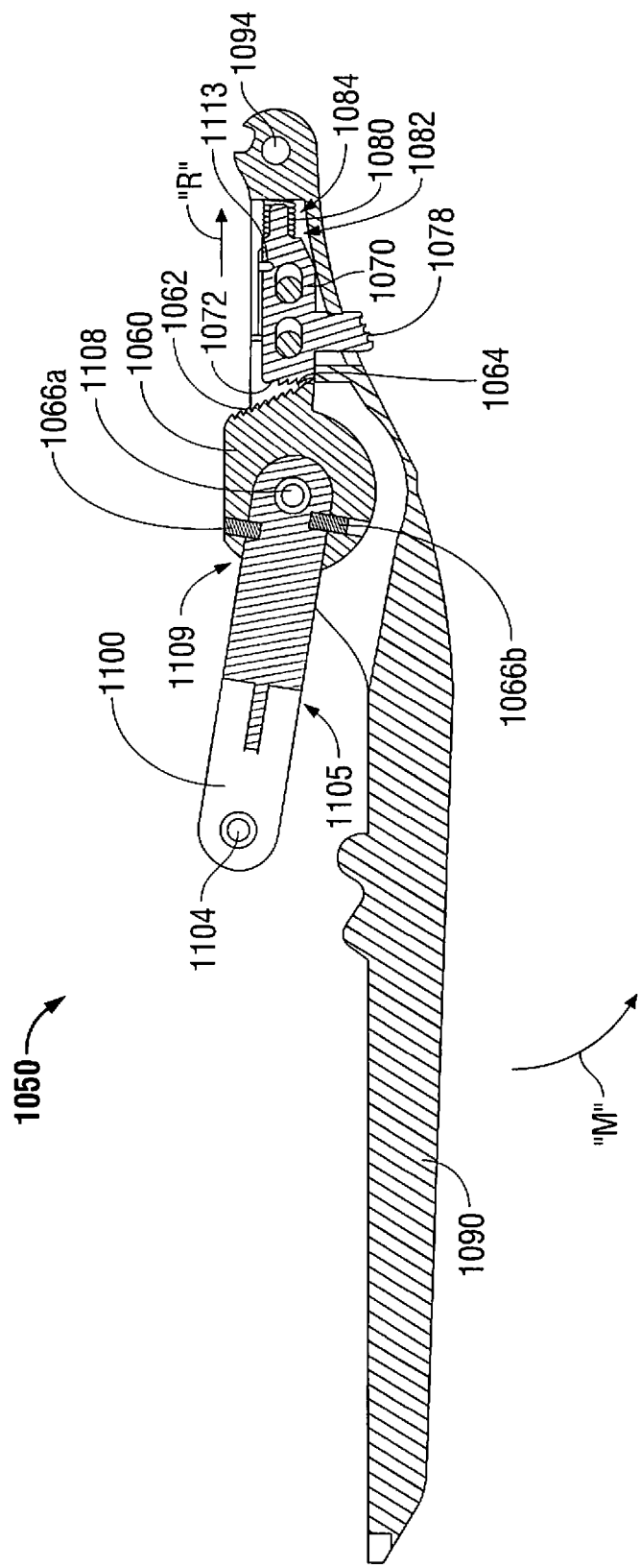
FIG. 105 is a longitudinal cross-sectional view of the ratchet mechanism of FIGS. 100-102 illustrated in its second approximated position.
Figure 106:
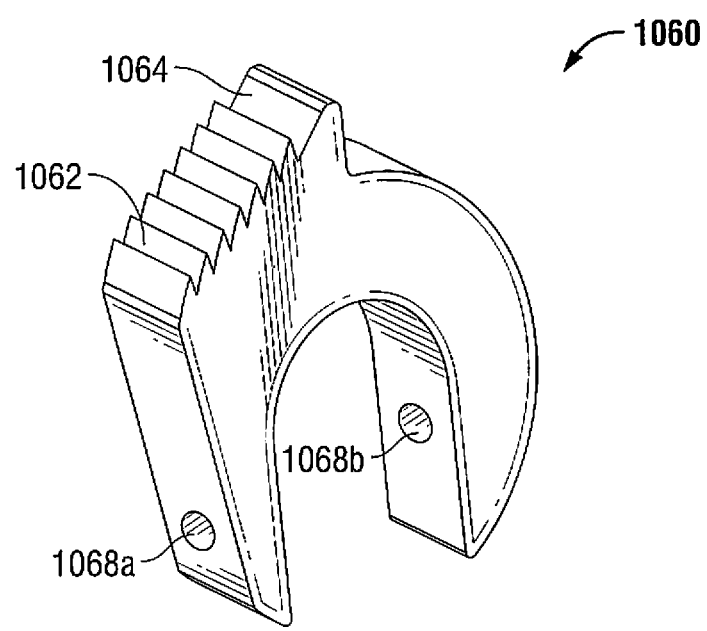
FIG. 106 is a perspective view of a rack of the ratchet mechanism of FIGS. 100-102 in accordance with an embodiment of the present disclosure.
Figure 107:
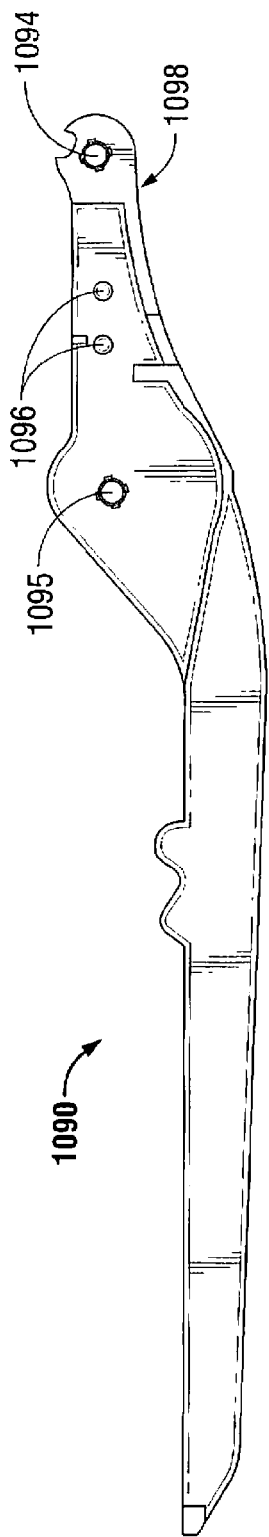
FIG. 107 is a longitudinal cross-sectional view of a trigger insert of the ratchet mechanism of FIGS. 100-102 in accordance with an embodiment of the present disclosure.
Figure 108:
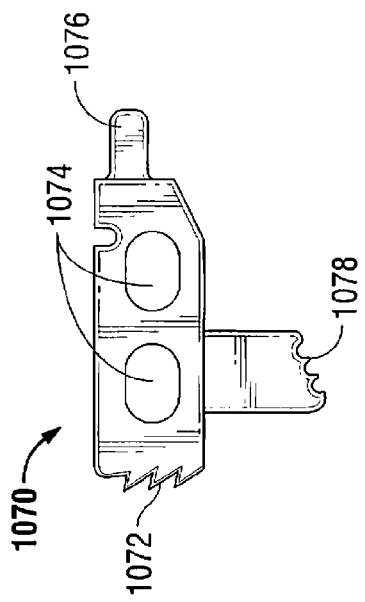
FIG. 108 is a side view of a pawl of the ratchet mechanism of FIGS. 100-102 in accordance with an embodiment of the present disclosure.

When movable handle 1040 has reached a predetermined position, illustratively the full firing stroke position, cam surface 1064 of rack 1060 engages pawl 1070 and translates pawl 1070 distally in the direction of arrow "R" (FIG. 105). When pawl 1070 is in its distal location (FIG. 105), movable handle 1040 is able to return to its first open position (either automatically, manually or spring-assisted), as rack teeth 1062 and pawl teeth 1072 are not engaged with one another.

Figure 102:
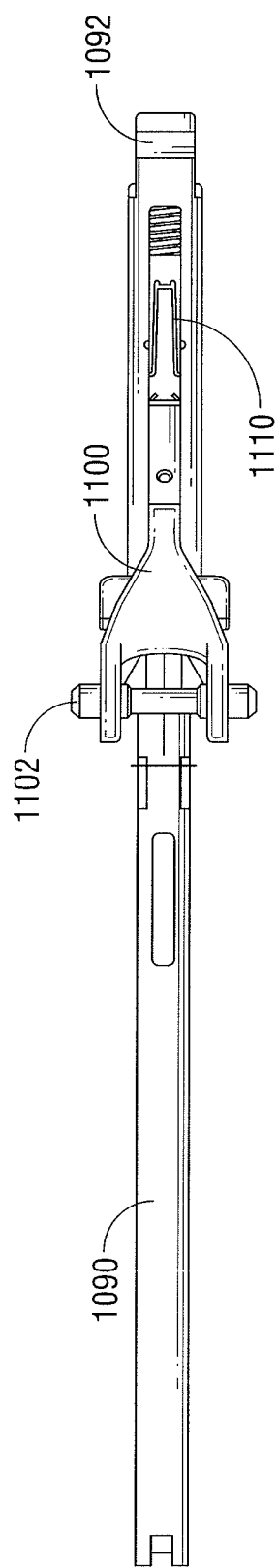
FIG. 102 is a top view of the ratchet mechanism of FIGS. 100-101.
Figure 102A:
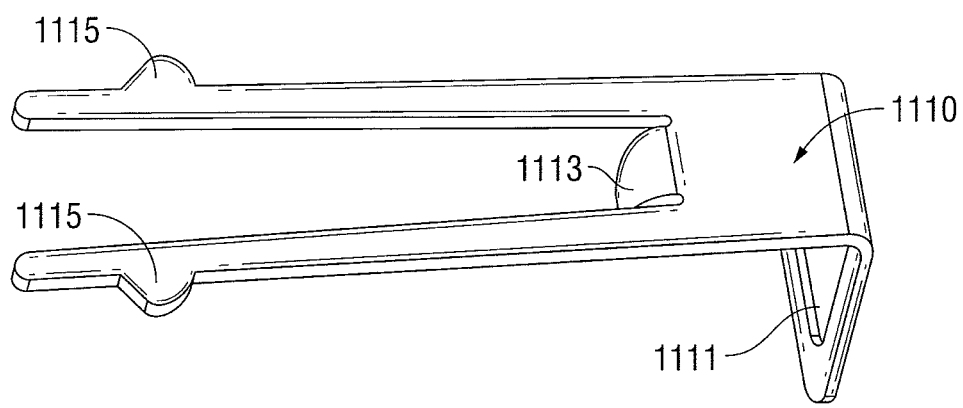
FIG. 102A is an enlarged view of the clip for the ratchet mechanism.
Figure 103:
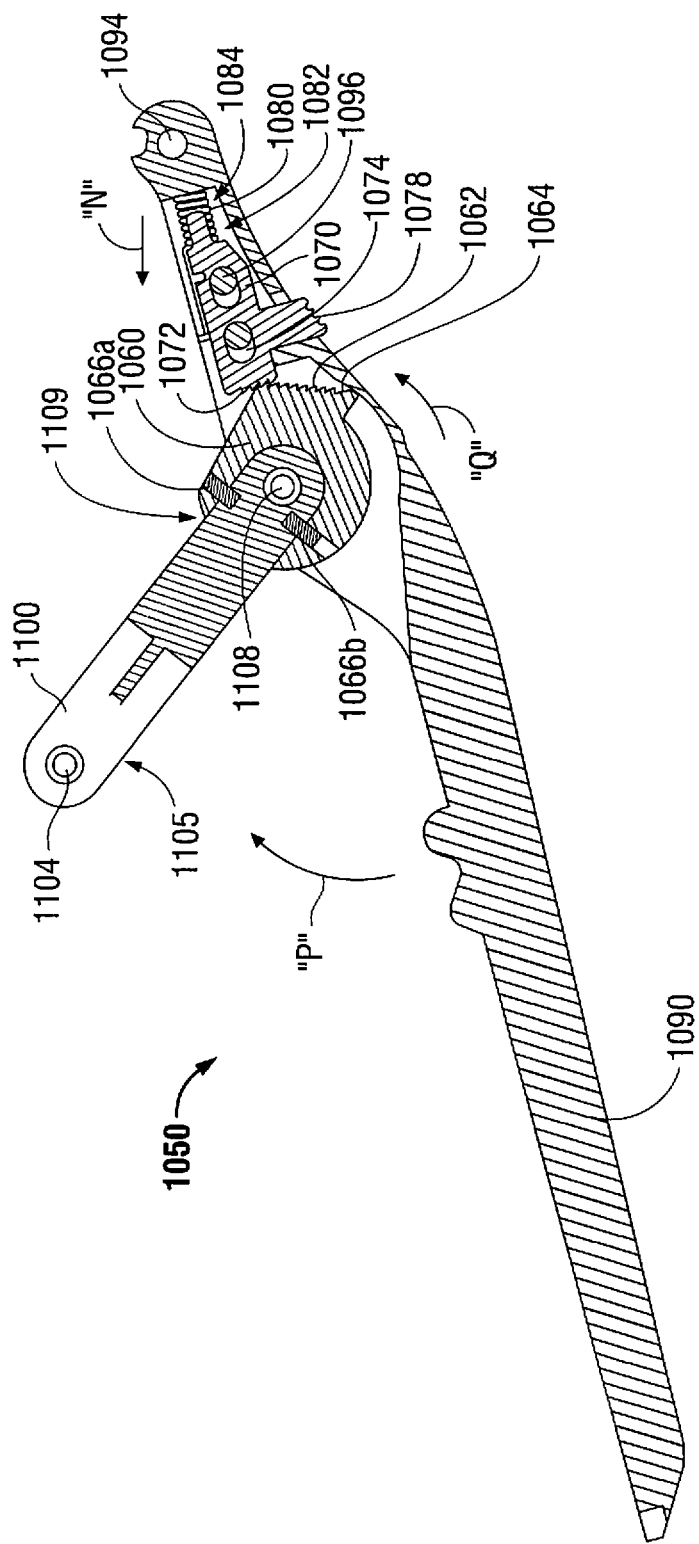
FIG. 103 is a longitudinal cross-sectional view of the ratchet mechanism of FIGS. 100-102 illustrated in its first open position.

Clip or latch 1110 is disposed in mechanical cooperation with spring 1080 and/or pawl 1070 and maintains pawl 1070 in a distal position after firing of the fasteners. More specifically, the bent down tab 1113 (FIGS. 102A and 105) of latch 1110 engages a notch on pawl 1070. Opening 1111 receives the spring hub 1076 of pawl 1070 and is spring biased proximally by spring 1080. When the handle 1040 is in the open position, the latch 1110 is biased proximally and the detents 115 are out of engagement with slots in the trigger insert 1090. When the movable handle 1040 is moved through the firing stroke to its second approximated (closed) position, pawl 1070 is moved distally as described above to the disengaged position. As pawl 1070 is moved distally, latch 1110 is moved distally due to the engagement of tab 1113 with pawl 1070. When the pawl 1070 is in its distal position, the detents 1115 on the latch 1110 engage notches on the trigger insert 1090. This retains the latch 1110 and therefore the pawl 1070 in the distal position, allowing the handle 1040 to move back to the open position with the rack teeth 1062 bypassing the pawl teeth 1072 due to the distal position of pawl 1070. The override 1078 can be used to disengage the latch 1110 to reset the rack 1060 and pawl 1070 to engagement.

It is envisioned in one embodiment that cam surface 1064 is configured to contact pawl 1070 when movable handle 1040 is between about 0.01 inches and about 0.05 inches (e.g., about 0.03 inches) from its second approximated position. Further, ratchet mechanism 1050 may be configured such that cam surface 1064 contacts pawl 1070 after staples have been fired from surgical stapling device 1000 or after a knife (e.g., 188, as described above with respect to another embodiment) has been translated to sever tissue, for example. In such instances, ratchet mechanism 1050 would help ensure that a surgical function would be completed prior to a user moving movable handle 1040 towards its first open position.

In the illustrated embodiments, pawl 1070 also includes an override 1078. Override 1078 is configured to allow a user to disengage rack teeth 1062 and pawl teeth 1072 from each other. Here, actuation of override 1078 prior to movable handle 1040 reaching the predetermined position allows movable handle 1040 to be moved towards its first open position, e.g., to reset ratchet mechanism 1050. To use override 1078 for disengaging rack teeth 1062 and pawl teeth 1072 from one another, an operator may translate override 1078 distally. Translation of override 1078 distally moves pawl 1070 distally against the bias of spring 1080 and correspondingly disengages pawl teeth 1072 from rack teeth 1062, thus allowing movable handle 1040 to move towards its first open position prior to movable handle 1040 reaching the predetermined position.

It is envisioned that instrument accessories may be used to assist in performing particular steps of the above described procedures. For example, an anal dilator may be inserted into the anus prior to performing the above-described method steps to provide easier access to the surgical site. An obturator may be used to assist in placement of the dilator. Also, an expandable introducer may be provided to reduce the trauma that results from insertion of the stapling device into the anus. Further, any combination of the components discussed above including the stapling device, anvil assembly, insertion handle, speculum anal dilator, and/or an obturator may be included in a kit to perform a hemorrhoidal treatment procedure.

It is noted that by providing a surgical stapler having a removable anvil assembly, visibility at the surgical site is greatly improved. This is especially important during placement of the purse string suture and cinching of the purse string suture about the anvil center rod.

It will be understood that various modifications may be made to the embodiments disclosed herein. Therefore, the above description should not be construed as limiting, but merely as exemplifications of disclosed embodiments. Those skilled in the art will envision other modifications within the scope and spirit of the claims appended hereto.

The invention claimed is:

1. A surgical stapling device comprising:
 a housing;
 an elongated portion extending distally from the housing;
 an end effector, at least a portion of the end effector being disposed in mechanical cooperation with a distal portion of the elongated portion;
 a exactly one pivotable handle disposed in mechanical cooperation with the housing, the pivotable handle being movable between a first open position and a second approximated position for effecting a function of the end effector; and
 a ratchet mechanism disposed in mechanical cooperation with the pivotable handle, the ratchet mechanism configured to releasably retain the position of the pivotable handle and to substantially prevent the pivotable handle from moving towards its first open position until the pivotable handle reaches the second position for effecting the function of the end effector, the ratchet mechanism including:
   a rack having rack teeth and a cam surface, the rack being disposed in mechanical cooperation with the housing;
   a link disposed in mechanical engagement with the rack and being pivotably coupled to the housing;
   a pawl having pawl teeth and being disposed in mechanical cooperation with the pivotable handle, the rack teeth and the pawl teeth being configured for engagement with each other; and
   a spring disposed in mechanical cooperation with the pivotable handle and being configured to bias at least one of the pawl and the rack towards the other such that the pawl teeth and the rack teeth are in engagement with one another,
   wherein the cam surface is configured to disengage the pawl teeth and the rack teeth upon the cam surface contacting the pawl for facilitating movement of the pivotable handle towards its first open position.

2. The surgical stapling device of claim 1, wherein the end effector is configured for ejection of staples therefrom upon movement of the pivotable handle from its first open position towards its second approximated position, and wherein the ratchet mechanism is configured to substantially prevent the pivotable handle from moving towards its first open position until at least one staple has been ejected from the end effector.

3. The surgical stapling device of claim 2, wherein the cam surface of the rack moves the pawl away from the rack after at least one staple has been ejected from the end effector.

4. The surgical stapling device of claim 1, further including a knife, the knife configured for distal translation upon movement of the pivotable handle from its first open position towards its second approximated position, and wherein the ratchet mechanism is configured to substantially prevent the pivotable handle from moving towards its first open position until the knife has been distally translated.

5. The surgical stapling device of claim 4, wherein the cam surface of the rack moves the pawl away from the rack after the knife has been distally translated.

6. The surgical stapling device of claim 1, wherein the spring is a compression spring and wherein the spring is configured to bias the pawl teeth into engagement with the rack teeth.

7. The surgical stapling device of claim 1, further including an override disposed in mechanical cooperation with the pawl and being accessible to a user of the assembled surgical stapling device, the override configured to allow a user to disengage the pawl teeth from the rack teeth before the pivotable handle reaches the second position, wherein disengagement of the pawl teeth from the rack teeth allows the pivotable handle to be moved towards its first open position.

8. The surgical stapling device of claim 1, wherein the rack is pivotably coupled to the pivotable handle.

9. The surgical stapling device of claim 1, further including a clip disposed in mechanical cooperation with the ratchet mechanism, the clip configured to releasably maintain the pawl teeth and the rack teeth in a disengaged position.

10. The surgical stapling device of claim 9, wherein the clip is automatically disengaged when the pivotable handle reaches its first open position.

11. The surgical stapling device of claim 1, wherein the end effector includes an anvil assembly and a shell assembly, the anvil assembly including an anvil head and an anvil center rod, the shell assembly supporting a plurality of staples, the anvil assembly being movable in relation to the shell assembly between spaced and approximated positions, and an actuator independent of the pivotable handle for moving the anvil assembly relative to the shell assembly.

12. A surgical stapling device comprising:
 a housing;
 an elongated portion extending distally from the housing;
 an end effector disposed adjacent a distal portion of the elongated portion and including an anvil assembly and a shell assembly, the anvil assembly including an anvil head and an anvil center rod having a proximal end and a distal end, the anvil head being supported on the distal end of the anvil center rod, the shell assembly supporting a plurality of staples, the anvil assembly being movable in relation to the shell assembly between spaced and approximated positions;
 exactly one pivotable handle disposed in mechanical cooperation with the housing, the pivotable handle being movable between a first open position and a second approximated position for effecting a function of the end effector;
 a ratchet mechanism disposed in mechanical cooperation with the pivotable handle, the ratchet mechanism configured to substantially prevent the pivotable handle from moving towards its first open position until the pivotable handle reaches the second position for effecting the function of the end effector, the ratchet mechanism including a pawl having a plurality of teeth, the pawl being capable of being physically contacted by a user when the surgical stapling device is fully assembled; and an approximation mechanism including an anvil retainer for supporting the anvil assembly, the anvil retainer including an annular shoulder configured to engage the anvil center rod to fasten the anvil center rod to the anvil retainer.

13. A surgical stapling device comprising:

a housing;

an elongated portion extending distally from the housing;

an end effector disposed adjacent a distal portion of the elongated portion and including an anvil assembly and a shell assembly, the anvil assembly including an anvil head and an anvil center rod having a proximal end and a distal end, the anvil head being supported on the anvil center rod, the shell assembly supporting a plurality of staples, the anvil assembly being movable in relation to the shell assembly between spaced and approximated positions;

exactly one pivotable handle disposed in mechanical cooperation with the housing, the pivotable handle being pivotable between a first position and a second position for effecting firing of the staples; and a ratchet mechanism disposed in mechanical cooperation with the pivotable handle, the ratchet mechanism configured to substantially prevent the pivotable handle from moving towards its first position until the pivotable handle reaches the second position and the staples have been fired, the ratchet mechanism including a rack and a link, the rack having rack teeth and a cam surface and being disposed in mechanical cooperation with the housing, the link being disposed in mechanical engagement with the rack and being pivotably coupled to the housing.

14. The surgical stapling device of claim 13, wherein the ratchet mechanism includes a pawl, at least one of the rack and the pawl being biased into engagement with the other of the rack and the pawl.

15. The surgical stapling device of claim 14, wherein after movement of the pivotable handle to fire the staples the pawl and the rack automatically disengage.

16. The surgical stapling device of claim 15, wherein the pawl is retained in a distal position upon movement of the pivotable handle to the second position to fire the staples.

17. The surgical stapling device of claim 13, further comprising an actuator independent of movement of the pivotable handle, the actuator moving the anvil assembly in relation to the shell assembly.

18. The surgical stapling device of claim 13, wherein teeth of the ratchet mechanism are pivotally movable with respect to the pivotable handle.

19. The surgical stapling device of claim 14, wherein a portion of the pawl is able to be physically contacted by a user after the surgical stapling device has been assembled.

20. The surgical stapling device of claim 1, wherein the rack is secured to the link.

21. The surgical stapling device of claim 1, wherein the rack and the link are free from movement with respect to each other.

22. The surgical stapling device of claim 12, wherein the ratchet mechanism includes a rack and a link, the rack having rack teeth and a cam surface and being disposed in mechanical cooperation with the housing, the link being disposed in mechanical engagement with the rack and being pivotably coupled to the housing.

23. The surgical stapling device of claim 1, wherein the rack is movable with respect to the pivotable handle.

24. The surgical stapling device of claim 1, wherein the rack and the link are mechanically engaged by pins.

25. The surgical stapling device of claim 7, wherein the override is included on the pawl.

* * * * *